United States Patent

Dehnert et al.

[11] 3,998,802
[45] Dec. 21, 1976

[54] AZO DYE WITH A 3-CYANO-OR 3-CARBAMOYL-4-METHYL-2,6-DIAMINO-PYRIDINE COUPLING COMPONENT

[75] Inventors: Johannes Dehnert; Gunther Lamm, both of Ludwigshafen, Germany

[73] Assignee: BASF Aktiengesellschaft, Ludwigshafen (Rhine), Germany

[22] Filed: Jan. 24, 1974

[21] Appl. No.: 435,306

Related U.S. Application Data

[63] Continuation-in-part of Ser. No. 209,431, Dec. 17, 1971, abandoned.

[30] Foreign Application Priority Data

Dec. 19, 1970 Germany .................. 2062717
Nov. 15, 1971 Germany .................. 2156545

[52] U.S. Cl. .................. 260/156; 260/206; 260/281 R; 260/294.9; 260/295 CA; 260/295 AM; 260/302 A; 260/304 A; 260/308 R; 260/310 C; 260/326 R; 260/465 G; 260/556 B; 260/578

[51] Int. Cl.² .................. C09B 29/36; C09B 31/14; D06P 3/24; D06P 3/52

[58] Field of Search .................. 260/156

[56] References Cited

UNITED STATES PATENTS

| | | | |
|---|---|---|---|
| 1,680,108 | 8/1928 | Ostromislensky | 260/156 |
| 1,802,062 | 4/1931 | Ostromislensky | 260/156 |
| 1,990,923 | 2/1935 | Tisza et al. | 260/156 |
| 2,029,315 | 2/1936 | Engelmann | 260/156 |
| 2,068,353 | 1/1936 | Schneiderwirth | 260/156 |
| 2,135,293 | 11/1938 | Renshaw et al. | 260/156 |
| 2,148,705 | 2/1939 | Mietsch et al. | 260/156 X |
| 2,857,372 | 10/1958 | Straley et al. | 260/146 |
| 3,357,968 | 12/1967 | Wilbert et al. | 260/156 |

FOREIGN PATENTS OR APPLICATIONS 270,987  12/1950  Switzerland .................. 260/156

*Primary Examiner*—Floyd D. Higel
*Attorney, Agent, or Firm*—Johnston, Keil, Thompson & Shurtleff

[57] ABSTRACT

Azo dyes of the formula

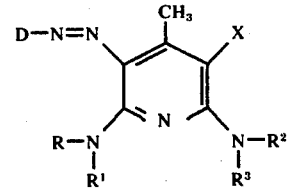

wherein D is the diazo component, the R substituents represent hydrogen or various organic radicals and X is cyano or carbamoyl. The R members are hydrogen, an alkyl or other aliphatic group as well as other selected groups including heterocyclic rings formed by $R + R^1$ and $R^2 + R^3$ with the nitrogen atom. The dyes are eminently suitable for dyeing polyamides, cellulose esters, acrylonitrile polymers and particularly polyesters brilliant yellow to blue shades of excellent fastness properties to dry-heat pleating and setting and also to light.

16 Claims, No Drawings

AZO DYE WITH A 3-CYANO- OR 3-CARBAMOYL-4-METHYL-2,6-DIAMINO-PYRIDINE COUPLING COMPONENT

This application is a continuation-in-part of U.S. application Ser. No. 209,431 filed on Dec. 17, 1971, now abandoned.

The invention relates to dyes of the general formula:

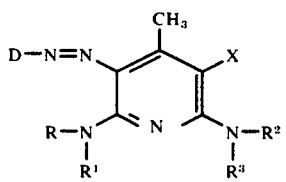

in which

D denotes the radical of a diazo component of the benzene, naphthalene, diphenyl, azobenzene, benzothiazole, thiophene, benzoisothiazole, thiazole, thiadiazole, triazole, benzotriazole, indazole, pyrazole or anthraquinone series;

X denotes cyano or carbamoyl;

R denotes hydrogen; alkyl of one to eight carbon atoms, alkyl bearing as substituents hydroxy, alkoxy of one to eight carbon atoms, carboxy, carbalkoxy of two to six carbon atoms, acyloxy of one to ten carbon atoms, or alkylamino of a total of up to eight carbon atoms, the alkyl if desired being interrupted by oxygen; phenyl; phenyl bearing chlorine, methyl, ethyl, β-hydroxyethyl, methoxy or ethoxy as substituents; cyclohexyl; benzyl; phenylethyl or omega-N-pyrrolidonylalkyl of two or three carbon atoms in the alkyl radical;

$R^1$ denotes hydrogen, alkyl of one to eight carbon atoms or alkyl bearing hydroxy, alkoxy of one to eight carbon atoms or alkylamino of a total of up to eight carbon atoms as substituents;

R and $R^1$ together with the nitrogen denote the radical of pyrrolidine, piperidine, morpholine, piperazine or N-methylpiperazine, and independently of one another $R^2$ has the same meanings as R, $R^3$ has the same meanings as $R^1$ and $R^2$ and $R^3$ have the same meanings as $R + R^1$.

The following are examples of subsituents for the radical D of the diazo components:

in the benzene series: chlorine, bromine, nitro, cyano, trifluoromethyl, methylsulfonyl, ethylsulfonyl, phenylsulfonyl, p-(β-hydroxyethylphenyl)-sulfonyl, carbomethoxy, carboethoxy, carbobutoxy, carbo-β-methoxyethoxy, carbo-β-ethylhexoxy, carbopropoxy, carbo-β-hydroxyethoxy, unsubstituted carbamoyl or sulfonamido, N-monosubstituted or N-disubstituted carbamoyl or sulfonamido, methyl, ethyl, methoxy and ethoxy;

Examples of N-substituents for the carboxamides or sulfonamides are methyl, ethyl, propyl, butyl, β-ethylhexyl, cyclohexyl, benzyl, phenylethyl, β-hydroxyethyl, β-hydroxypropyl, β-methoxyethyl, and γ-methoxypropyl as well as pyrrolidide, piperidide and morpholide.

in the azobenzene series: chlorine, bromine, nitro, cyano, carbalkoxy, methyl, ethyl, methoxy, ethoxy, hydroxy, acetylamino, formyl, β-hydroxyethoxy and ethoxycarbonylamino;

in the heterocyclic series: chlorine, bromine, nitro, cyano, methyl, ethyl, phenyl, methoxy, ethoxy, methylmercapto, β-carbomethoxyethylmercapto, β-carboethoxyethylmercapto, carbomethoxy, carboethoxy, methylsulfonyl and ethylsulfonyl.

In addition to the radicals already mentioned individually, R, $R^1$, $R^2$ and $R^3$ may denote for example:

methyl, ethyl, propyl, butyl, hexyl, β-ethylhexyl, β-hydroxyethyl, β-hydroxypropyl, γ-hydroxypropyl, ω-hydroxyhexyl, β-methoxyethyl, γ-methoxypropyl, β-ethoxyethyl, γ-ethoxypropyl, γ-isopropoxypropyl, γ-butoxypropyl, β-aminoethyl, γ-dimethylaminopropyl, γ-dibutylaminopropyl and ω-aminohexyl and also the radicals of the formulae:

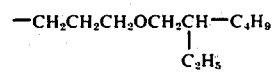

$-CH_2=CH-CH_2$, $-(CH_2)_3O(CH_2)_4OH$, $-(CH_2)_3OC_2H_4OCH_3$, $-(CH_2)_3OC_2H_4OC_6H_5$, $-CH_2-CHOHC_6H_5$,

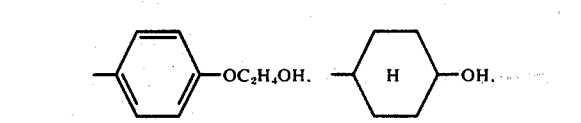

$CH_2COOH$, $C_2H_4COOH$, $-(CH_2)_3COOH$ and $-(CH_2)_5COOH$.

Examples of acyloxyalkyl radicals are:
$-CH_2-CH_2-O-acyl$, $-CH_2-CH_2-CH_2-O-acyl$,

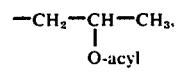

$-CH_2-CH_2-CH_2-CH_2-O-acyl$, $-CH_2-CH_2-CH_2-CH_2-CH_2-O-acyl$, $-CH_2-CH_2-O-CH_2-CH_2-O-acyl$,

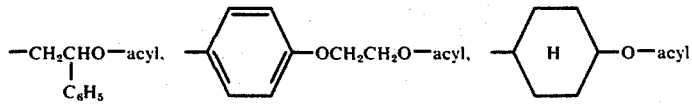

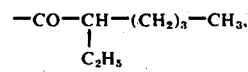

and $-CH_2-CH_2-CH_2-O-CH_2-CH_2-CH_2-CH_2-O-acyl$.

Examples of acyl radicals are the following:
$-CO-H$, $-CO-CH_3$, $-CO-CH_2-CH_3$, $-CO-CH(CH_3)_2$,

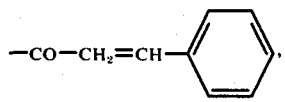

—CO—CH₂—CO—CH₃,   —CO—CH₂—Cl,
—CO—CH₂—CH₂—Cl, —CO—=CH₂, —CO—CH=λ
CH—CH₃,

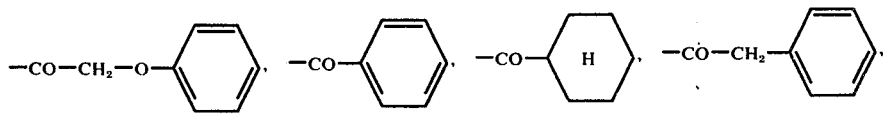

—CO—CH=CH—COOH,   —CO—CH₂—CH-
₂—COOH, —CO—CH₂—CH₂—COO—C₂H₅,

—CO—O—CH₃, —CO—O—C₂H₅, —CO—O—CH-
₂—CH₂—O—CH₃, —CO—N—(CH₃)₂,

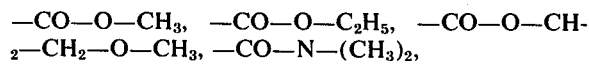

—CO—CH₂—O—CH₃, —CO—CH₂—S—CH₃,

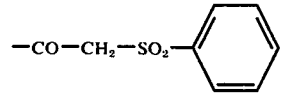

and —CO—CH₂—SO₂—CH₃.

The following are examples of carbalkoxyalkyl groups:
—CH₂—COO—Y,
—CH₂—CH₂—COO—Y,
—CH₂—CH₂—CH₂—COO—Y,
—CH₂—CH₂—CH₂—CH₂—CH₂—COO—Y and
—CH₂—CH₂—O—CO—CH₂—CH₂—COO—Y,
where Y denotes alkyl, cycloalkyl, aralkyl, hydroxyalkyl, alkoxyalkyl or aroxyalkyl. Specific examples of Y are methyl, ethyl, propyl, butyl, cyclohexyl, benzyl, hydroxyethyl, hydroxybutyl, hydroxyhexyl, methoxyethyl, methoxypropyl, ethoxypropyl, phenoxyethyl and hydroxyethoxyethyl.

Dyes of formula (I) with acyloxyalkyl groups in which the alkyl radical is preferably of the formula —CH₂—CH₂—,

—CH₂—CH—CH₃,
        |

(CH₂)₃ or —CH₂—CH₂—O—CH₂—CH₂— are of particular industrial significance. Preferred acyl radicals are: formyl, acetyl, acetoacetyl, phenoxyacetyl and phenylacetyl. Dyes having two formyl groups have special significance The radical D may be derived for example from the following amines:

aniline, o-toluidine, m-toluidine p-toluidine, o-nitroaniline, m-nitroaniline, p-nitroaniline, o-cyanoaniline, m-cyanoaniline, p-cyanoaniline, 2,4-dicyanoaniline, p-chloroaniline, 3,4-dichloroaniline, 2,5dichloroaniline, 2,4,5-trichloraniline, 2,4,6-trichloroaniline o-bromoaniline, m-bromoaniline, p-bromoaniline, 2,4,6-tribromoaniline, 2-chloro-4-nitroaniline, 2-bromo-4-nitroaniline, 2-cyano-4-nitroaniline, 1-amino-4-methyl-2-nitrobenzene, 1-amino-4-methoxy-2-nitrobenzene, 1-amino-4-chloro-2-nitrobenzene, 2-cyano-4-nitro-6-bromoaniline, 2-cyano-4-nitro-6-chloroaniline, 1-amino-2-methyl-4-nitrobenzene, 1-amino-2-trifluoromethyl-4-chlorobenzene, 1-amino-2-methoxy-4-nitrobenzene, N-benzoyl-p-phenylenediamine, N-acetyl-p-phenylenediamine, N-phenylsulfonyl-p-phenylenediamine, N-phenylsulfone-m-phenylenediamine, 4-aminoacetophenone, 4-aminobenzophenone, 2-aminobenzophenone, 4-methylsulfonylaniline, 2-aminodiphenylsulfone, methyl 2-aminobenzoate, methyl 3-aminobenzoate, methyl 4-aminobenzoate and the corresponding ethyl, propyl, butyl, isobutyl, β-ethylhexyl, cyclohexyl, benzyl, phenyl, β-methoxyethyl, β-ethoxyethyl, β-butoxyethyl, methyldiglycol, ethyldiglycol, methyltriglycol, ethyltriglycol, β-hydroxyethyl, β-acetoxyethyl, β-(β'-hydroxyethoxy)-ethyl, β-hydroxypropyl, γ-hydroxypropyl, δ-hydroxybutyl, and ω-hydroxyhexyl esters of 4-aminobenzoic acid, the methyl, isobutyl, methyldiglycol, β-methoxyethyl, β-butoxyethyl, methyldiglycol, β-acetoxyethyl or butyl ester of 4-nitroanthranilic acid, the dimethyl, diethyl, dipropyl or dibutyl ester of 3-aminophthalic acid, 4-aminophthalic acid, 5-aminophthalic acid or terephthalic acid, the imide, methylimide, propylamide, n-butylamide, isobutylamide, cyclohexylamide, isooctylamide, methoxypropylamide, ethoxypropylamide or anilide of 3-aminobenzoic acid or 4-aminobenzoic acid, the dimethylamide, diethylamide, pyrrolidide, morpholide or N-methyl-N-β-hydroxyethylamide of 2-aminobenzoic acid, 3-aminobenzoic acid or 4-aminobenzoic acid, the diamide or bis-γ-methoxypropylamide of 5-aminoisophthalic acid, the bis-diethylamide of aminoterephthalic acid, the imide, β-hydroxyethylimide, γ-hydroxypropylimide, phenylimide or tolylimide of 3-aminophthalic acid or 4-aminophthalic acid, the β-hydroxyethylimide of 3-amino-6-nitrophthalic acid, the dimethylamide, diethylamide, pyrrolidide, morpholide, or N-methylanilide of 2-aminobenzosulfonic acid, 3-aminobenzosulfonic acid or 4-aminobenzosulfonic acid, the 2'-aminophenyl ester, 3'-aminophenyl ester or 4'-aminophenyl ester of methylsulfonic acid, the 2'-aminophenyl, 3'-aminophenyl or 4'-aminophenyl ester of ethylsulfonic acid, the 2'-aminophenyl, 3'-aminophenyl or 4'-aminophenyl ester of butylsulfonic acid, the 2'-aminophenyl, 3'-aminophenyl or 4'-aminophenyl ester of benzenesulfonic acid, 2,4-dinitro-6-bromoaniline, 2,4-dinitro-6- chloroaniline, 1-amino-2,6-dibromobenzene-4-methylsulfone, 2-chloro-5aminobenzonitrile, 1-aminobenzene-4-methylsulfone, 2-amino-4-chlorobenzonitrile, 1-amino-2,6-dichlorobenzene-4-methylsulfone, the methyl, or methoxyethyl ester of 1-amino-2,4-dinitrobenzene-6-carboxylic acid, the 1,8-methoxyethylimide or 1,8-methoxypropylimide of 4-aminonaphthalic acid, 1-amino-4-nitrobenzene-2-methylsulfone, 1-amino-4-nitro-2,6-dicyanobenzene, 2,4-dinitroaniline, 2-amino-6,7-dichlorobenzothiazole, 2-amino-5,6-dichlorobenzothiazole, 1-amino-2-nitrobenzene-4-sulfonic acid n-butylamide, the β-methoxyethylamide of 1-amino-2-nitrobenzene-4-sulfonic acid, 1-aminoanthraquinone, 1-amino-4-chloroanthraquinone, 1-aminonaphthalene, 2-aminonaphthalene, 1-amino-2-ethoxynaphthalene, 4-aminonaphthalic acid butylimide, the propyl ester of 3,5-dichloroanthranilic acid, the β-methoxymethyl ester of 3,5-dibromoanthranilic acid, 5-aminochromanone, 2-aminodiphenyl, 3-aminodiphenylene oxide, 4-aminodiphenylene oxide, 2-amino-3,5-dinitrobenzonitrile, 1-amino-2,4-dinitrobenzene-6-methylsulfone, 2-amino-6-nitrobenzothiazole, 2-amino-6-methylsulfonylbenzothiazle, 2-amino-6-ethylsulfonylbenzothiazole, 2-amino-3-cyano-4-methyl- 5-carbomethoxy-thiophene, 2-amino-3-cyano-4-methyl- 5-carboethoxy-thiophene or 2-amino-5-nitrothiophene.

Examples of suitable compounds which can be formed into diazo components of the aminoazobenzene series are:

4-aminoazobenzene, 2',3-dimethyl-4-aminoazobenzene, 3',2-dimethyl-4-aminoazobenzene, 2,5-dimethyl-4-aminoazobenzene, 2-methyl-5-methoxy-4-aminoazobenzene 4'-chloro-2-methyl-5-methoxy-4-aminoazobenzene, 2-methyl-4',5-dimethoxy-4-aminoazobenzene, 4'-hydroxy-4-aminoazobenzene, 4'-hydroxy-3'-methyl-4-aminoazobenzene, 2'-hydroxy-5'-methyl-4-aminoazobenzene, 4'-hydroxy-2-methoxy-4-aminoazobenzene, 4'-hydroxy-2-chloro-4-aminoazobenzene, 4'-hydroxy-2,5-dimethoxy-4-aminoazobenzene, 4-hydroxy-2,6-dichloro-4'-aminoazobenzene, 2,5-dimethoxy-4-aminoazobenzene, 4'-chloro-2,5-dimethoxy-4-aminoazobenzene, 4'-nitro-2,5-dimethoxy-4-aminoazobenzene, 4'-nitro-4-aminoazobenzene, 4'-nitro-2-methyl-5-methoxy-4-aminoazobenzene, 4'-chloro-2-methyl-4-aminoazobenzene, 4'-chloro-2,5-dimethyl-4-aminoazobenzene, benzenazo-4-amino-3-ethyoxynaphthalene and benzeneazo-4-aminonaphthalene or the compounds having the formulae:

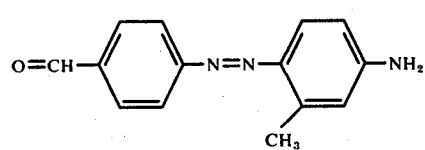 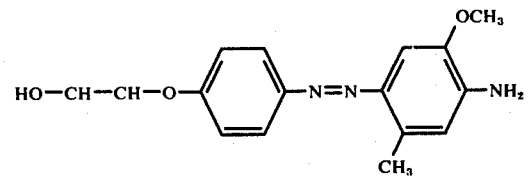

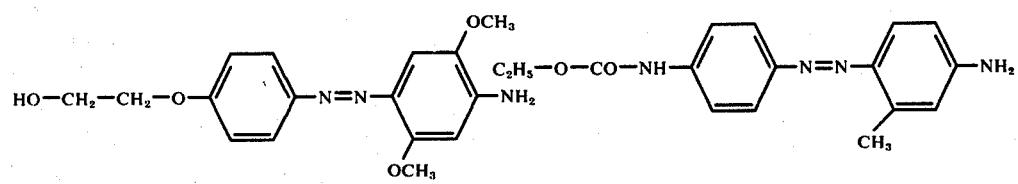

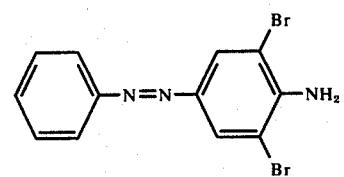 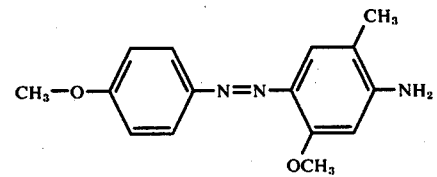

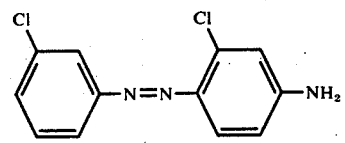 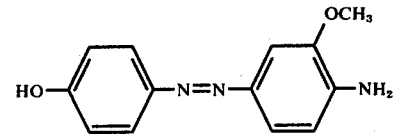

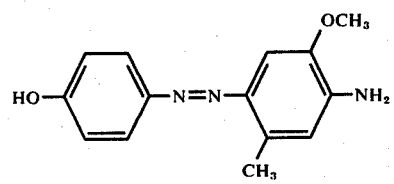 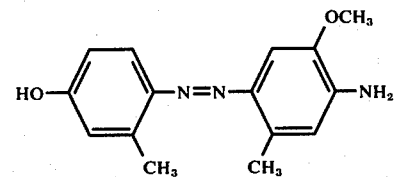

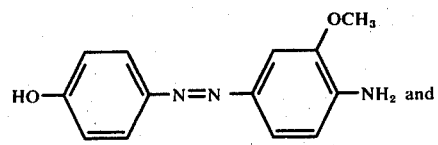 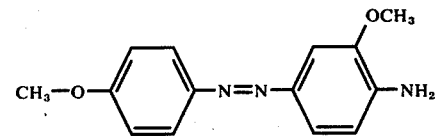

For the production of dyes of the formula (I), a diazo compound of an amine of the general formula (II):

$$D-NH_2 \qquad (II)$$

may be reacted with a coupling component of the general formula (III):

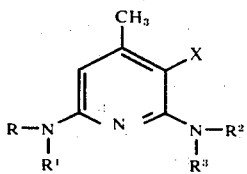

D, R, R[1], R[2], R[3] and X having the meanings given above.

Diazotization of the amines may be carried out as usual. Coupling is also carried out as usual in aqueous medium, with or without adding solvents, in a weakly to strongly acid reaction.

Dyes having acyloxy groups may also be obtained by acylating (introducing acyl into) the hydroxyl groups present in the dye after diazotiazation and coupling. For this purpose the free acids, anhydrides, chlorides or esters on which the acyl radicals are based are suitable and the reactions are conventionally carried out in the presence of an inert diluent or solvent such as monochlorobenzene, dichlorobenzene, trichlorobenzene, tetrahydrofuran, dioxane, dimethylformamide, N-methylpyrrolidone or pyridine.

When free acids are used for the esterification it may be advantageous to add an inorganic or organic acid as a catalyst, for example HCl gas or toluenesulfonic acid. The water formed may be removed from the reaction mixture, for example by evaporation.

When acid anhydrides or chlorides are used for esterification, the corresponding acid may serve as solvent in special cases. Thus for example reactions with acetic anhydride may be carried out in glacial acetic acid as solvent.

When acid chlorides are used as the esterification agent it is advantageous to add acid-binding agents, for exampe sodium carbonate, sodium acetate, magnesium oxide or pyridine to the reaction mixture.

In addition to the said esterification agents, special reference may be made to diketene and isocyanates such as methyl or phenyl isocyanate.

Naturally it is also possible to introduce the carbalkoxy group by subsequent esterification of the dyes containing carboxyl groups by a conventional method.

Production of the coupling components of the formula (II) may be carried out by reaction of 2,6-dichloro-3-cyano-4-methylpyridine or 2,6-dichloro-4-methylpyridine-(3)-carboxamide with an amine of the general formula (IV):

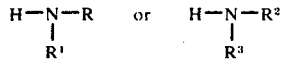

Primary or secondary amines may be used. It is possible by suitable choice of the reaction conditions to substitute the chlorine atoms of the 2,6-dichloro-3-cyano-4-methylpyridine in stages so that monosubstitution and disubstitution products can be isolated. Reaction conditions which exert influence on the exchange of chlorine atoms include temperature, amine component, molar ratio of the reactants and the diluent or solvent. It is probable that in the first stage of the reaction it is mainly 2-amino-3-cyano-4-methyl-6-chloropyridines that are obtained and these, with or without isolation, may be reacted with the same or different amine radicals. The cyano group may then be converted into the carbamoyl group by a conventional method.

When 2,6-dichloro-3-cyano-4-methylpyridine is reacted with a mixture of different amines with complete exchange of the chlorine atoms, mixtures of coupling components are obtained. When two amines are used, for example a mixture of four coupling components is otained, whereas with a mixture of three amines a mixture of nine coupling components is obtained.

The dye mixtures which can be prepared from these may have substantially better affinity for synthetic fibers than a single dye of the mixture, provided suitable amines are chosen.

When ammonia or volatile amines such as methylamine or ethylamine are chosen as amine components for the production of 2,6-diamino-3-cyano-4-methylpyridine derivatives, it is recommended that solutions of these amines or of ammonia in a solvent which is inert under reaction conditions should be used. Inert solvents for reaction temperatures of up to about 150° C include for example alcohols such as methanol, ethanol and β-methoxyethanol. If the components are allowed to react at higher temperatures, examples of suitable solvents are dimethylformamide, N-methylpyrrolidone, glycol and a glycol ether such as ethylene glycol dimethyl ether.

The liquefied amine itself may be used at superatmospheric pressure and the reaction period prolonged.

Exces amine or conventionally used acid-binding agents such as tertiary amines, magnesium oxide, alkoxides or alkalies may be used to bind the HCl liberated in the reaction.

Examples of amines of the formula (IV) are: ammonia, allylamine, methylamine, ethylamine, n-propylamine, isopropylamine, n-butylamine, isobutylamine, tert-butylamine, isoamylamine, n-hexylamine, isohexylamine, n-octylamine, isooctylamine, 2-ethylbutylamine, 2-ethylhexylamine, cyclohexylamine, β-hydroxyethylamine, β-hydroxypropylamine, γ-hydroxypropylamine, ω-hydroxyhexylamine, β-methoxyethylamine, β-ethoxyethylamine, β-butoxyethylamine, γ-(β'-ethylhexoxy)-propylamine, β-(β'-hydroxyethoxy)-ethylamine, γ-ethoxypropylamine, γ-methoxypropylamine, γ-isopropoxypropylamine, γ-amino-α-N-methylaminopropane, γ-amino-α-N-dimethylaminopropane, α-amino-β-diethylaminoethane, β-amino-β-ethyl-α,γ-propanediol, β-amino-β-methylpropanol, N-ethyl-N-(β-hydroxyethyl)-amine, diethanolamine, dimethylamine, diethylamine, dipropylamine, N-methyl-N-(β-hydroxy)-ethylamine, morpholine, piperidine, piperazine, N-methylpiperazine, pyrrolidine, thiomorpholine-S-dioxide, β-aminoethylthiomorpholine-S-dioxide, N-(γ-aminopropyl)-pyrrolidone, aniline, o-toluidine, m-toluidine, p-toluidine, o-methoxyaniline, m-methoxyaniline, p-methoxyaniline, o-chloroaniline, m-chloroaniline, p-chloroaniline, p-cyanoaniline, m-cyanoaniline, p-cyanoaniline, o-ethoxyaniline, m-ethoxyaniline, p-ethoxyaniline, o-ethylaniline, m-ethylaniline, p-ethylaniline, the methylamide of p-aminobenzoic acid, p-aminobenzoic acid β-methoxyethylamide, 1-amino-4-(β-hydroxyethyl)-benzene, 1-amino-4-(β-hydroxyethoxy)-benzene, N-β-hydroxyethylaniline, N-methylaniline, benzylamine, β-phenylethylamine, 1,3-diaminopropane, 1,2-diaminoethane, 1,2-diaminopropane, 1,6-diaminohexane and 1,4-diaminobutane.

Dyes and dye mixtures of the general formula (Ia):

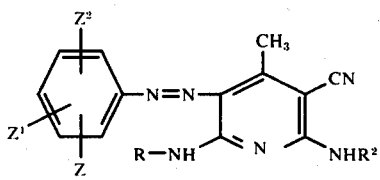

(Ia)

in which

Z² denotes hydrogen, nitro, cyano, chloro, bromo, carbomethoxy, carboethoxy, methylsulfonyl, ethylsulfonyl, methyl or methoxy, Z denotes hydrogen, nitro, chloro, bromo, cyano, methyl, methoxy, carbomethoxy, carboethoxy, methylsulfonyl or ethylsulfonyl and Z¹ denotes hydrogen, chloro, bromo, cyano, methyl, methoxy, carbomethoxy, carboethoxy phenylazo, p-nitrophenylazo, p-hydroxyphenylazo, p-methoxyphenylazo, p-chlorophenylazo or methylphenylazo and R and R² have the meanings given above except hydrogen are of particular industrial interest.

Preferred radicals R and R² are ω-hydroxyhexyl, γ-hydroxypropyl and the radicals having the formulae:
—(CH₂)₂—O(CH₂)₂OH,   —(CH₂)₃O(CH₂)₄OH,
—CH₂CHOHC₆H₅, —(CH₂)₃O(CH₂)₂OC₆H₅,

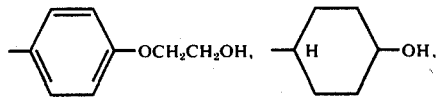

(CH₂)₃N(CH₃)₂, —(CH₂)₃N(C₄H₉)₂, CH₂CH₂OCHO, —CH₂CH₂CH₂OCHO, —CH₂CH₂OCOCH₃, —CH₂CH₂OCOCH₂OC₆H₅, —CH₂CH₂CH₂OCOCH₂OC₆H₅, —CH₂CH₂OCH₂CH₂OCHO, —CH₂CH₂OCH₂CH₂OCOCH₂OC₆H₅, —CH₂CH₂OCOCH₂C₆H₅ and —CH₂CH₂OCH₂CH₂OCOCH₂C₆H₅.

Preferred dyes not having ester groups in the coupling components are those in which the sum of the carbon atoms of the radicals R and R² amounts to from about 7 to 14, the presence of ether and preferably hydroxy groups being advantageous.

Preferred dyes having ester groups are those having a total of from about 6 to 16 carbon atoms in the radicals R and R².

Moreover the corresponding dyes which contain, as diazo components, a benzoisothiazole or benzothiazole which may bear nitro, chloro, bromo or cyano as a substituent, or a thiadiazole bearing as a substituent an unsubstituted or substituted alkylmercapto radical, or a substituted thiophene are particularly valuable.

The following are examples of particularly valuable diazo components:
1-amino-4-nitrobenzene,
1-amino-3-chloro-4-nitrobenzene,
1-amino-2-bromo-4-nitrobenzene,
2-amino-5-nitrobenzonitrile,
2-amino-5-chlorobenzonitrile,
3-chloro-4-aminobenzonitrile,
2-chloro-4-aminobenzonitrile,
2-aminobenzonitrile,
2,5-dichloro-4-aminobenzonitrile,
1-amino-2,4-dicyanobenzene,
1-amino-2,4-dicyano-6-chlorobenzene,
2-chloro-4-amino-5-nitrobenzonitrile,
1-amino-2,5-dichloro-4-nitrobenzene,
1-amino-2,6-dichloro-4-nitrobenzene,
1-amino-2,6-dibromo-4-nitrobenzene,
1-amino-2-bromo-4-nitro-6-chlorobenzene,
1-amino-2,4-dinitrobenzene,
1-amino-2,4-dinitro-6-chlorobenzene,
1-amino-2,4-dinitro-6-bromobenzene,
1-amino-4-nitrobenzene-2-methylsulfone,
1-amino-4-nitrobenzene-2-ethylsulfone,
4-aminophenylmethylsulfone,
1-amino-2-chlorobenzene-4-methylsulfone,
1-amino-2,6-dichlorobenzene-4-methylsulfone,
1-amino-2,6-dibromobenzene-4-methylsulfone,
4-aminobenzoic acid esters,
1-amino-4-nitro-2-carboxylic acid esters,
1-amino-2-bromo-4-nitro-6-carboxylic acid esters,
1-amino-2,4-dichloro-6-carboxylic acid esters,
1-amino-2,4-dibromo-6-carboxylic acid esters,
4-aminoazobenzene, 2',3-dimethyl-4-aminobenzene,
4'-hydroxy-2'-methyl-4-aminoazobenzene,
1-amino-2,4-dinitrobenzene-6-carboxylic acid methyl
or methoxy ester, 3,5-dibromo-4-aminoazobenzene,
3',2-dimethyl-4-aminoazobenzene,
2,5-dimethyl-4-aminoazobenzene,
2-methyl-5-methoxy-4-aminoazobenzene,
4'-chloro-2-methyl-5-methoxy-4-aminoazobenzene,
4'-nitro-2,5-dimethoxy-4-aminoazobenzene,
4'-nitro-2-methyl-5-methoxy-4-aminoazobenzene, and
4'-chloro-2-methyl-5-methoxy-4-aminoazobenzene.

The following are particularly valuable heterocyclic diazo components:
2-amino-5-nitrothiazole,
2-amino-4-methyl-5-nitrothiazole,
2-amino-5-phenylthiadiazole-1,3,4,
3-phenyl-5-aminothiadiazole-1,2,4,
3-methylmercapto-5-aminothiadiazole-1,2,4,
3-β-carbomethoxyethylmercapto-5-aminothiadiazole-1,2,4,
3-amino-5-nitro-2,1-benzoisothiazole,
3-amino-5-nitro-7-chloro-2,1-benzoisothiazole,
3-amino-5-nitro-7-bromo-2,1-benzoisothiazole,
3-amino-7-nitrobenzoisothiazole,
4-amino-5-bromobenzoisothiazole,
4-amino-5-bromo-7-nitrobenzoisothiazole,
4-amino-5-cyano-7-nitrobenzoisothiazole,
2-amino-6-nitrobenzothiazole,
2-amino-3-cyano-4-methyl-5-carbomethoxythiophene and
2-amino-3-cyano-4-methyl-5-carboethoxythiophene.

The new dyes are yellow to green blue and are suitable for dyeing acrylonitrile polymer textile material and particularly textile material of synthetic polyamides and cellulose esters, such as secondary cellulose acetate or triacetate, or synthetic linear polyesters such as polyethylene glycol terephthalate or polymers of analogous chemical constitution. Dyeings of unusual brilliance and good color strength are obtained therewith which are distinguished by good fastness properties, particularly fastness to dry-heat pleating and setting and to light.

The following Examples illustrate the invention. Parts and percentages in the following Examples are by weight unless otherwise stated.

PRODUCTION OF COUPLING COMPONENTS

EXAMPLE 1

54 parts of 2,6-dichloro-3-cyano-4-methylpyridine is introduced at from 20° to 30° C into a mixture of 90 parts of β-methoxyethylamine and 70 parts of methanol. The mixture is stirred for three hours at 40° C and then 1000 parts of ice-water is added. After acidification with hydrochloric acid to pH 4 to 5, the precipitate which has been deposited is suction filtered and washed with water. 50 parts of the product has 120 parts of β-hydroxyethylamine added to it. The mixture is then stirred for three to four hours at 160° to 170° C. The mixture is then allowed to cool to 120° C, poured while stirring on to 500 parts of ice and 500 parts of water and acidified with hydrochloric acid to pH 5 to 6. About 50 parts of a dark green oil is obtained which slowly solidifies. The melting point of the crude product is 108° to 111° C.

The probable formula is:

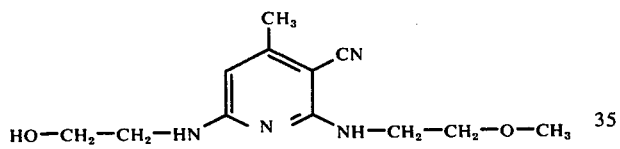

The product contains a minor amount of a coupling component of the probable formula:

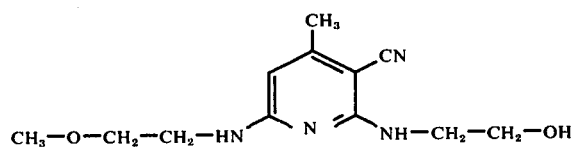

EXAMPLE 2

187 parts of 2,6-dichloro-3-cyano-4-methylpyridine is gradually added at 20° to 30° C to a mixture of 250 parts by volume of β-hydroxyethylamine and 200 parts by volume of methanol. The mixture is stirred for four to five hours at 40° C and then added with good stirring to 3000 parts of ice-water. The whole is acidified with hydrochloric acid to pH 6 to 4. The deposited precipitate is filtered off, washed with water and dried. 202 parts of a colorless powder is obtained.

100 parts of this powder is boiled under reflux with 300 parts by volume of β-methoxyethylamine for twelve hours. Excess amine is then distilled off, and the residue is stirred into 1500 parts of ice-water and adjusted to pH 6 to 7 with hydrochloric acid. The deposited precipitate is filtered off, washed with water and dried. About 100 to 110 parts of a brownish to colorless powder is obtained of the probable formula:

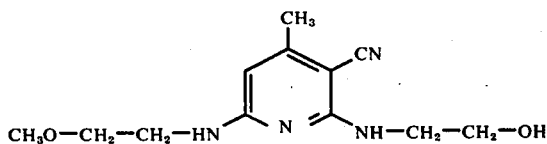

It melts at 78° to 81° C. The product may contain a minor amount of the coupling component of the probable formula:

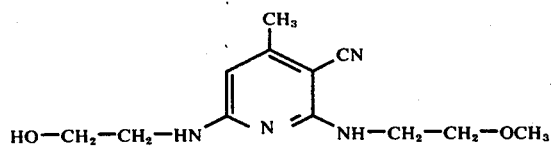

EXAMPLE 3

220 parts by volume of β-hydroxyethylamine is added to 93 parts of 2,6-dichloro-3-cyano-4-methylpyridine and cautiously heated to 165° to 170° C. The whole is stirred for two to three hours at this temperature, allowed to cool to 120° C, added to 700 parts of ice-water, and the pH is adjusted to 7 to 6. After filtration by suction and drying, 97 parts of a colorless powder is obtained of the formula:

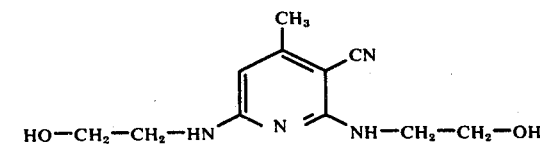

m.p. 156° C.

EXAMPLE 4

54 parts of 2,6-dichloro-3-cyano-4-methylpyridine is gradually added at 15° to 35° C while cooling to a mixture of 80 parts of diethylamine and 130 parts by volume of methanol. The mixture is stirred for four hours at 35° C and then poured into 1000 parts of water. After acidification with hydrochloric acid to pH 6, the product is suction filtered and washed with water. After recrystallization from methanol, 50 parts of a colorless powder is obtained of the probable formula:

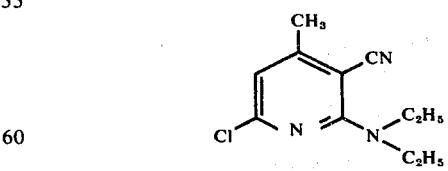

The melting point is 88° to 90° C.

EXAMPLE 5

120 parts by volume of β-hydroxyethylamine is added to 54 parts of the product of the formula:

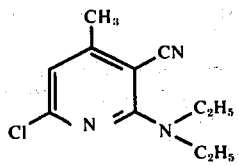

and stirred for two to three hours at 165° C. The whole is then allowed to cool to 110° C and 1000 parts of water and hydrochloric acid is added to set up a pH of 6 to 7. After cooling to room temperature, the oily product obtained is separated from the aqueous phase by a conventional method. It has the probable formula:

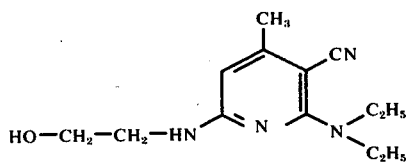

The product gradually solidifies and melts at 106° to 108° C.

EXAMPLE 6

A mixture of 120 parts by volume of 3-methoxypropylamine and 120 parts by volume of n-hexylamine is added to 100 parts of the product of the formula:

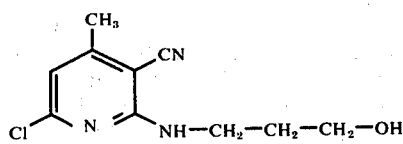

m.p. 118° to 120° C.

The mixture is heated under reflux for 12 hours. Excess amine is then distilled off and the residue has added to it 1500 parts of water and hydrochloric acid to set up a pH of 6 to 7. The oil which separates is isolated from the aqueous phase as usual. The yield is about 190 to 220 parts of a dark oil which consists of the coupling components:

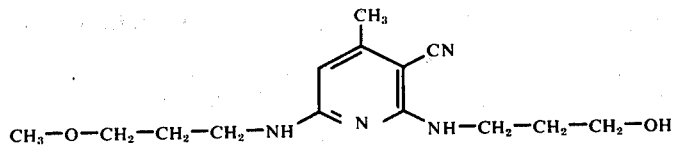

and

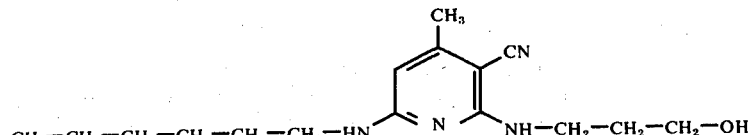

EXAMPLE 7

A mixture of 50 parts of β-methoxyethylamine, 50 parts of β-hydroxyethylamine and 25 parts of n-butylamine is allowed to flow at 60° to 100° C into a mixture of 108 parts of 2,6-dichloro-3-cyano-4-methylpyridine and 130 parts of N-methylpyrrolidone. The mixture is then stirred for 10 hours under reflux after which the excess amine is distilled off. The residue has added to it 2000 parts of water and hydrochloric acid up to a pH of 6. The oil which separates is isolated. The yield is about 100 to 115 parts of a mixture of amines having the formula:

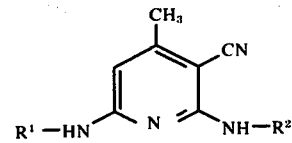

in which $R^1$ and $R^2$ denote the radicals:
—$CH_2$—$CH_2OH$, —$CH_2$—$CH_2$—O—$CH_3$ or —$CH_2$—$CH_2$—$CH_2$—$CH_3$ and $R^1$ and $R^2$ may be identical or different.

EXAMPLE 8

54 parts of 2,6-dichloro-3-cyano-4-methylpyridine is gradually added at 35° to 40° C while cooling to a mixture of 30 parts of β-hydroxyethylamine and 30 parts of β-methoxyethylamine in 100 parts of N-methylpyrrolidone. The whole is stirred for 4 to 5 hours at 40° C, 40 parts of n-hexylamine is then added and the mixture is heated for another ten to twelve hours under reflux. Excess amine is then distilled off and 1000 parts of water is added to the residue. After acidification with hydrochloric acid to pH 6 to 5, about 54 parts of a dark oil is obtained which is isolated as usual from the aqueous phase. The product has the formula:

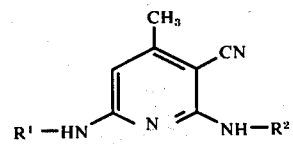

in which $R^1$ and $R^2$ denote the radical —$CH_2$—$CH_2$—OH, —$CH_2$—$CH_2$—O—$CH_3$ or —$CH_2$—$CH_2$—$CH_2$—$CH_2$—$CH_3$ and $R^1$ and $R^2$ may be identical or different.

EXAMPLE 9

130 parts of 90% sulfuric acid is added to 50 parts of the product described in Example 8 and stirred for 5 to 6 hours at 80° to 100° C. The whole is then allowed to cool, poured while stirring onto 800 parts of ice and neutralized with 50% caustic soda solution. The mixture is extracted with ethyl acetate and the extractant is distilled off. 48 parts of a dark oil is obtained having the formula:

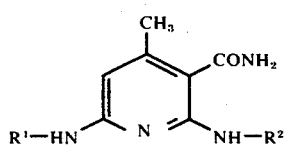

in which R¹ and R² have the meanings given in Example 8.

EXAMPLE 10

250 parts of 90% sulfuric acid is added to 100 parts of 2,6-dichloro-3-cyano-4-methylpyridine and is stirred for 4 to 8 hours at 70° to 100° C, then allowed to cool and the mixture is poured onto 1000 parts of ice while stirring, filtered off and wased with water. About 80 to 90 parts of a colorless powder is obtained having the formula:

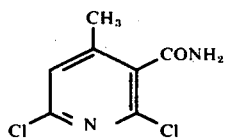

which melts at 178° C.
IR spectrum:

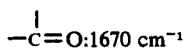

PRODUCTION OF DYES

EXAMPLE 11

25 parts of the product described in Example 10 is heated with 100 parts of β-hydroxyethylamine for 4 hours at 160° to 165° C, allowed to cool, 3000 parts of water is added, the whole acidified with hydrochloric acid to pH 3 to 4, cooled to 0° C and 21.2 parts of a solution of 4-aminoazobenzene which has been diazotized in the usual way is added to the mixture which is then adjusted to pH 1 to 2 with sodium acetate solution. After the coupling is over, the deposited dye is washed with water and dried. About 42 parts of a red brown powder is obtained having the formula:

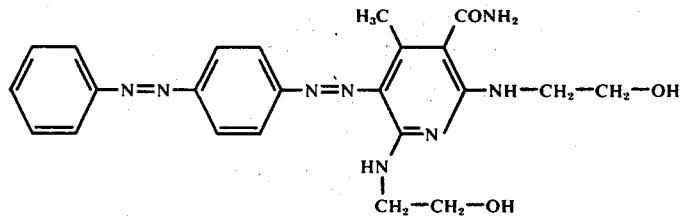

which dissolves in dimethylformamide with a violet color and dyes cellulose esters red shades, polycaprolactam and polyethylene terephthalate cloth full red brown shades with very good fastness properties.

EXAMPLE 12

8.3 parts of the β-methoxyethyl ester of p-aminobenzoic acid is stirred with 100 parts of water and 12 parts of 30% hydrochloric acid. 100 parts of ice and 16 parts by volume of 23% sodium nitrite solution are then added and the whole is stirred for 2 hours at 0° to 5° C. The diazonium salt solution obtained is added gradually at 0° C to a solution of 12.3 parts of 2,6-di-(β-hydroxyethyl)-amino-3-cyano-4-methylpyridine in 350 parts of water and 12 parts by volume of 30% hydrochloric acid. During coupling the pH of the coupling mixture is kept at 0 to 2 by dripping in sodium acetate solution or 50% caustic soda solution. After coupling is over, the deposited dye of the formula:

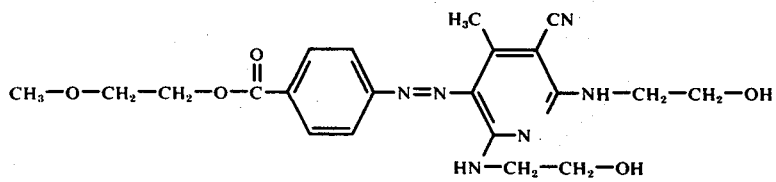

is filtered off, washed with water and dried. A yellow powder is obtained which dissolves in dimethylformamide with an orange yellow color and dyes polycaprolactam and polyethylene terephthalate cloth yellow shades.

Using the diazo components and coupling components of the following Table, other dyes which have similar properties are obtained by methods analogous to the said method:

PCL = polycaprolactam; PETP = polyethylene terephthalate.

| Ex. | Diazo component | Coupling component | acetate | PCL | PETP |
|---|---|---|---|---|---|
| 13 | C₂H₅OC(O)–C₆H₄–NH₂ (4-amino, ethyl ester) | 4-methyl-3-cyano-2,6-bis(2-hydroxyethylamino)pyridine | yellow | yellow | yellow |
| 14 | C₆H₁₃(n)OC(O)–C₆H₄–NH₂ | " | yellow | yellow | yellow |
| 15 | C₈H₁₇(n)OC(O)–C₆H₄–NH₂ | " | yellow | yellow | yellow |
| 16 | C₆H₁₃(n)OC(O)–C₆H₃(NO₂)–NH₂ | " | — | yellowish red | yellowish red |
| 17 | CH₃–O–CH₂CH₂–NHC(O)–C₆H₄–NH₂ | " | — | yellow | yellow |
| 18 | C₆H₅–OC(O)–C₆H₄–NH₂ | " | — | reddish yellow | reddish yellow |
| 19 | C₂H₅O–C(O)–C₆H₃(Br)–NH₂ | " | reddish yellow | reddish yellow | reddish yellow |
| 20 | 2-NH₂–C₆H₄–COOCH₂–CH₂–O–CH₃ | " | yellow | yellow | yellow |
| 21 | O₂N–C₆H₃(OCH₃)–NH₂ | " | — | yellowish red | yellowish red |
| 22 | CH₃–O–CH₂CH₂–NHC(O)–C₆H₄–NH₂ | 4-methyl-3-cyano-2,6-bis(n-butylamino)pyridine | — | — | yellow |
| 23 | O₂N–C₆H₃(Cl)–NH₂ | 4-methyl-3-cyano-2,6-bis(2-methoxyethylamino)pyridine | yellow | yellowish red | yellowish red |
| 24 | " | 4-methyl-3-carbamoyl-2,6-bis(2-methoxyethylamino)pyridine | red | red | red |
| 25 | O₂N–C₆H₄–NH₂ | 4-methyl-3-carbamoyl-2-(2-methoxyethylamino)-6-(2-hydroxyethylamino)pyridine | — | red | red |

EXAMPLE 26

12.1 parts of 2-amino-3-bromo-5-nitrobenzonitrile is introduced at 0° to 5° while stirring into a mixture of 15 parts of nitrosylsulfuric acid (with a content of 13.1% of dinitrogen trioxide) and 35 parts of concentrated sulfuric acid. The whole is stirred for 4 hours at 0° to 5° C and the diazonium salt mixture is then added gradually to a solution, cooled to 0° C, of 12.3 parts of the coupling component described in Example 5 in 300 parts of water and 12 parts by volume of 30% hydrochloric acid. The pH of the coupling mixture is held at 0 to 1.5 by adding caustic soda solution or sodium acetate. After coupling is over, the deposited precipitate is filtered off, wased with water and dried. A dark red powder of the formula:

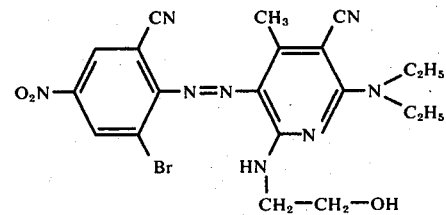

is obtained which dissolves in dimethylformamide with a violet color and dyes polyethylene terephthalate and polycaprolactam cloth ruby red shades.

By using equivalent amounts of the diazo components and coupling components set out in the following Table and following the procedure described in the foregoing Example, dyes having similar fastness properties are obtained.

Column 1 gives the number of the Example
Column 2 gives the diazo component
Column 3 gives the coupling component
Columns 4, 5 and 6 give the shades of dyeings on cellulose acetate, polycaprolactam and polyethylene terephthalate, respectively.

| 1 | 2 | 3 | 4 | 5 | 6 |
|---|---|---|---|---|---|
| 27 | 2-amino-5-chlorobenzonitrile (Cl, CN, NH₂ benzene) | pyridine coupler: CH₃, CN, N(R²)(R³), HN—R¹; R¹ = C₂H₅OH; R², R³ = C₂H₅ | yellow | yellow | yellow |
| 28 | 2,4,6-trichloroaniline (Cl, Cl, Cl, NH₂ benzene) | " | yellow | yellow | yellow |
| 29 | 2-amino-5-nitrobenzonitrile (O₂N, NH₂, CN benzene) | R¹ = CH₂CH₂OCH₃; R² = CH₃; R³ = CH₂CH₂OH | bluish red | — | — |
| 30 | 2-amino-5-nitro-methylsulfonyl (O₂N, SO₂CH₃, NH₂) | " | bluish red | — | — |
| 31 | (O₂N, NH₂, S, N thiazole) | R¹ = CH₂CH₂OCH₃; R² = C₂H₅; R³ = CH₂CH₂OH | blue | blue | — |
| 32 | 2-amino-4-nitrobenzonitrile (O₂N, CN, NH₂) | R¹ = CH₂CH₂OH; R², R³ = C₂H₅ | — | red | red |
| 33 | " | R¹ = CH₂CH₂OH; R² = CH₂CH₂CH₂OCH₃; R³ = H | red | red | red |
| 34 | (O₂N, CN, NH₂) | x = —CN; R¹ = CH₂CH₂CH₂OCH₃; R = CH₂CH₂OH; R³ = H | — | red | red |

-continued

| 1 | 2 | 3 | 4 | 5 | 6 |
|---|---|---|---|---|---|
| 35 | 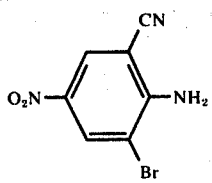 (2-amino-3-bromo-5-nitrobenzonitrile) | $R^1 = CH_2CH_2CH_2OCH_3$<br>$R^2 = CH_2CH_2OH$<br>$R^3 = H$ | red | bluish red | bluish red |
| 36 | " | $R^1 = CH_2CH_2OH$<br>$R^2 = C_6H_{13}(n)$<br>$R^3 = H$ | — | " | " |
| 37 | " | $R^1 = C_6H_{13}(n)$<br>$R^2 = CH_2CH_2OH$<br>$R^3 = H$ | — | " | " |
| 38 | 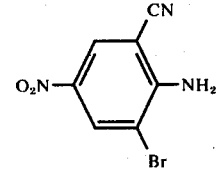 | $R^1 = CH_2CH_2OH$<br>$R^2 = $ –C$_6$H$_4$–CH$_3$ (p-tolyl)<br>$R^3 = H$ | — | bluish red | bluish red |
| 39 | " | 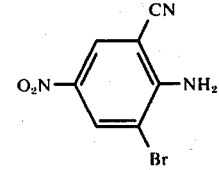 pyridine with CH$_3$, CN, NHR$^2$, HN–R$^1$<br>$R^1, R^2 = $ –C$_6$H$_4$–CH$_3$, –CH$_2$CH$_2$OH | — | " | " |
| 40 | " | $R^1, R^2 = $ –CH$_2$CH$_2$OH, –C$_6$H$_4$–OCH$_3$ | — | " | " |
| 41 | 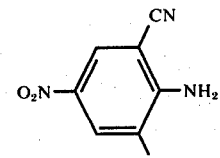 | pyridine with CH$_3$, CN, NHR$^2$, HN–R$^1$<br>$R^1, R^2 = $ –CH$_2$CH$_2$CH$_2$OCH$_3$, –C$_6$H$_4$–CH$_2$CH$_2$OH | — | " | " |
| 42 | " | $R^1, R^2 = $ –C$_6$H$_4$–CH$_2$CH$_2$OH, –CH$_2$CH$_2$OH | bluish red | " | " |
| 43 | 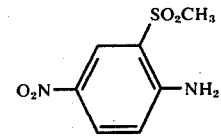 | $R^1, R^2 = $ –CH$_2$CH(CH$_3$)–OH, –CH$_2$CH$_2$CH$_2$OCH$_3$ | — | red | red |
| 44 | " | $R^1, R^2 = $ –CH$_2$CH$_2$OCH$_3$, –CH$_2$–CH$_2$–OH | — | red | red |
| 45 | 2-amino-5-nitro-SO$_2$CH$_3$-benzene | $R^1, R^2 = $ –CH$_2$CH$_2$CH$_2$OCH$_3$, –CH$_2$–CH$_2$–OH | — | red | red |

-continued
| 1 | 2 | 3 | 4 | 5 | 6 |
|---|---|---|---|---|---|
| 46 | 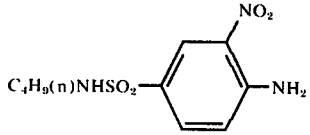 | R¹, R² = —CH₂CH₂OH | — | yellow-ish red | yellow-ish red |
| 47 | 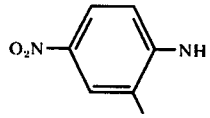 | R¹, R² = —CH₂CH₂OCH₃<br>—CH₂—CH₂—OH | — | red | red |
| 48 | 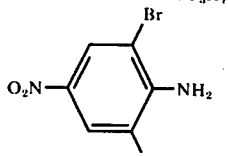 | " | — | red | red |
| 49 | 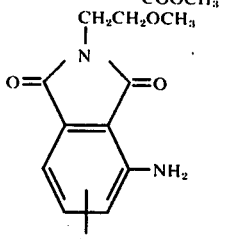 | R¹, R² = —CH₂CH₂OCH₃<br>—CH₂—CH₂—OH | — | yellow-ish red | yellow-ish red |
| 50 | 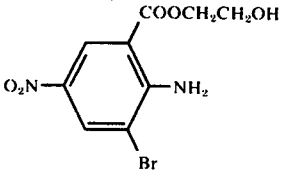 | 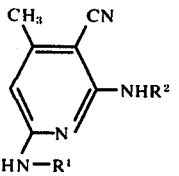<br>R¹ = CH₂CH₂CH₂OCH₃<br>R² = H | — | red | red |
| 51 | 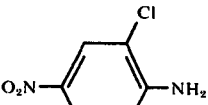 | R¹, R² = —CH₂CH₂OH,<br>—CH₂CH₂CH₂OCH₃ | — | yellow-ish red | yellow-ish red |
| 52 | 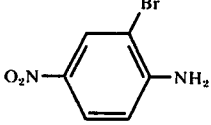 | " | — | " | " |
| 53 | 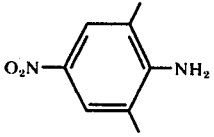 | " | — | red brown | red brown |
| 54 | 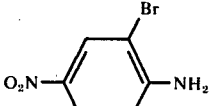 | " | — | " | " |
| 55 | 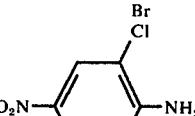 | " | — | " | " |
| 56 | 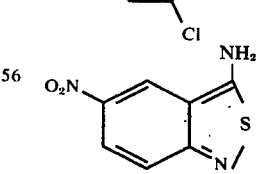 | " | — | blue violet | blue violet |

-continued

| 1 | 2 | 3 | 4 | 5 | 6 |
|---|---|---|---|---|---|
| 57 | '' | $R^1, R^2 = C_6H_{13}(n)$, $-CH_2CH_2OCH_3$ | — | '' | '' |
| 58 | '' | $R^1, R^2 = C_6H_{13}(n)$, $-CH_2-CH_2-OH$ | — | '' | '' |
| 59 | [structure: Br, $O_2N$, $NH_2$, benzisothiazole] | [pyridine structure with $CH_3$, CN, $NHR^2$, $HN-R^1$] | violet | violet | violet |
| 60 | [anthraquinone with $NH_2$] | $R^1, R^2 = -CH_2CH_2OCH_3$, $-CH_2CH_2OCH_2CH_2OH$ | — | red brown | red brown |
| 61 | [structure: $O_2N$, CN, $NH_2$, Br] | $R^1, R^2 = CH_2-CH=CH_2$ | — | — | red |
| 62 | '' | $R^1, R^2 = -CH_2-CH=CH_2$, $-CH_2-CH_2-OH$ | — | red | red |
| 63 | [structure: $O_2N$, CN, $NH_2$, Br] | [pyridine with $CH_3$, CN, morpholino, $HN-CH_2-CH_2-OH$] | bluish red | bluish red | bluish red |
| 64 | [structure: $O_2N$, CN, $NH_2$ pyridine] | '' | red | red | red |
| 65 | [structure: $O_2N$, $NH_2$, benzisothiazole] | '' | — | blue | blue |
| 66 | [structure: $O_2N$, CN, $NH_2$, Br] | [pyridine with $CH_3$, CN, pyrrolidino, $HN-CH_2-CH_2-OH$] | — | red | red |
| 67 | '' | [pyridine with $CH_3$, CN, N-methylpiperazino, $HN-CH_2-CH_2-OH$] | — | — | ruby |
| 68 | '' | [pyridine with $CH_3$, CN, $NH-CH_2CH_2N$-pyrrolidinone, $HN-CH_2-CH_2-OH$] | — | bluish red | bluish red |
| 69 | '' | [pyridine with $CH_3$, CN, $NH-CH_2-CH_2-OH$, $HN-CH_2CH_2O-CH_2CH_2CH_3$] | — | '' | '' |

EXAMPLE 70

11.5 parts of the compound of the formula:

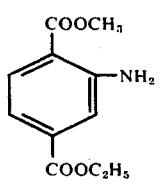

is stirred with 13 parts by volume of 30% hydrochloric acid and 200 parts of water. The mixture is then cooled to 0° to 5° C, 16 parts by volume of 23% sodium nitrite solution is dripped in and the whole is stirred for two hours at 0° C. After 1 part of sulfamic acid has been added, the diazonium salt mixture is allowed to flow gradually into a solution, cooled to 0° C, of 13.5 parts of the coupling component mixture described in Example 7 in 300 parts of water and 12 parts by volume of 30% hydrochloric acid. Then 10 to 50% caustic soda solution is added until the pH is 1.5. After coupling is over, the precipitated dye mixture of the formula:

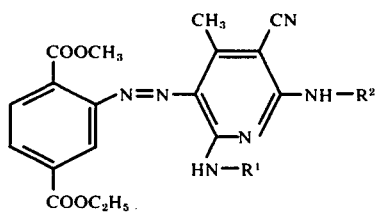

in which $R^1$ and $R^2$ have the meanings given in Example 7 is isolated. It dissolves in dimethylformamide to give an orange color and dyes polyethylene terephthalate cloth full golden yellow shades.

EXAMPLE 71

13.1 parts of 2,4-dinitro-6-bromoaniline is slowly introduced at 0° C into a mixture of 63 parts of 85% sulfuric acid and 16 parts of nitrosylsulfuric acid (with a content of 13.1% of dinitrogen trioxide). After stirring for four to five hours at 0° C, the diazonium salt mixture is gradually added to a solution, cooled to 0° C, of 13.5 parts of the coupling component mixture described in Example 7 and 1 part of sulfamic acid in 300 parts of water and 13 parts by volume of 30% hydrochloric acid. The whole is stirred for ten minutes and then sodium acetate and ice are added so that the pH of the coupling mixture rises to 1 and the temperature does not exceed 3° C. AFter coupling is over, the deposited dye mixture is suction filtered, washed with water and dried. A dark red powder is obtained which has the formula:

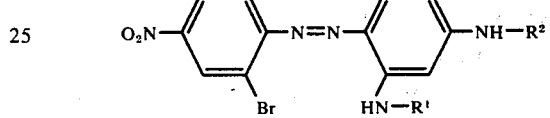

in which $R^1$ and $R^2$ have the meanings given in Example 7. The dye mixture dissolves in dimethylformamide with a red violet color and dyes polyethylene terephthalate cloth red shades.

Other dyes are obtained in an analogous way with the diazo components and coupling components set out in the following Table.

| 1 | 2 | 3 | 4 | 5 | 6 |
|---|---|---|---|---|---|
| 72 | ![NO2, NH2 benzene] | Example 7 | — | orange | orange |
| 73 | ![NO2, CH3, NH2 benzene] | " | — | " | " |
| 74 | ![NO3, CH3O, NH2 benzene] | " | — | " | " |
| 75 | ![NO2, O2N, NH2 benzene] | " | — | red | red |
| 76 | ![Br, O2N, NH2, NO2 benzene] | " | — | bluish red | bluish red |

-continued
| 1 | 2 | 3 | 4 | 5 | 6 |
|---|---|---|---|---|---|
| 77 | 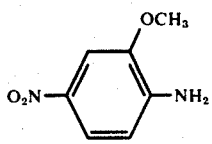 | " | — | yellowish red | yellowish red |
| 78 | 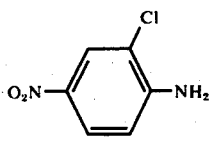 | " | — | " | " |
| 79 | 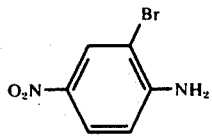 | " | — | " | " |
| 80 | 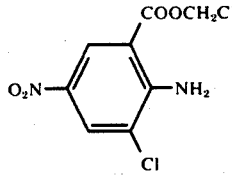 | " | — | red | red |
| 81 | 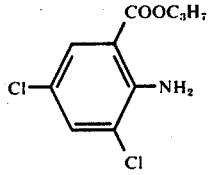 | " | — | orange | orange |
| 82 | 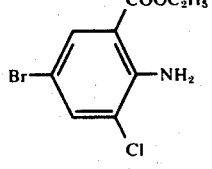 | " | — | " | " |
| 83 | 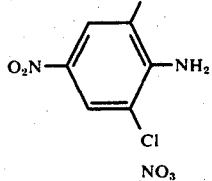 | " | — | bluish red | bluish red |
| 84 | 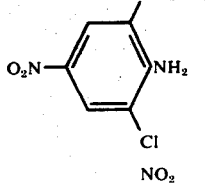 | " | — | red | red |
| 85 | 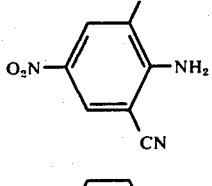 | " | — | bluish red | bluish red |
| 86 | 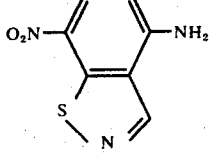 | " | — | red | red |

| 1 | 2 | 3 | 4 | 5 | 6 |
|---|---|---|---|---|---|
| 87 | 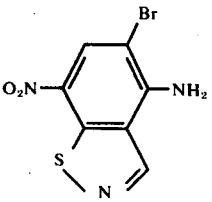 | " | — | violet | violet |
| 88 | 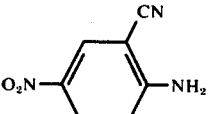 | " | — | red | red |
| 89 | 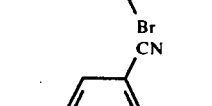 | " | — | yellowish red | yellowish red |
| 90 | 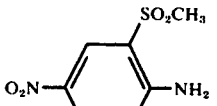 | " | — | red | red |
| 91 | 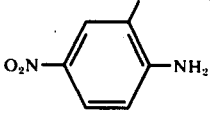 | " | — | red | red |
| 92 | 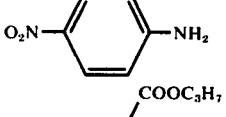 | " | — | " | " |
| 93 | 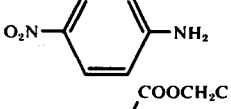 | " | — | " | " |
| 94 | 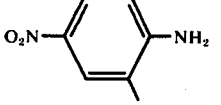 | " | — | " | " |
| 95 | 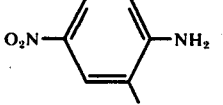 | " | — | red brown | red brown |
| 96 | 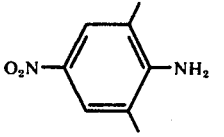 | " | — | " | " |
| 97 | 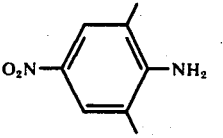 | " | — | " | " |

| 1 | 2 | 3 | 4 | 5 | 6 |
|---|---|---|---|---|---|
| 98 | 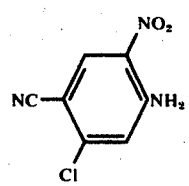 | " | — | red | red |
| 99 | 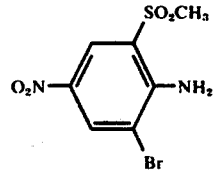 | Example 7 " | — | " | " |
| 100 | 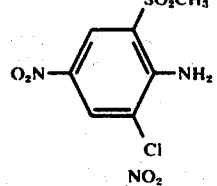 | " | — | " | " |
| 101 | 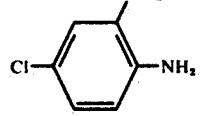 | " | — | orange | orange |
| 102 | 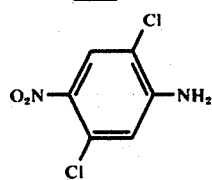 | " | — | " | " |
| 103 | 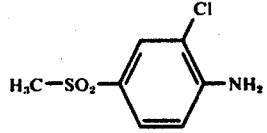 | " | — | reddish yellow | reddish yellow |
| 104 | 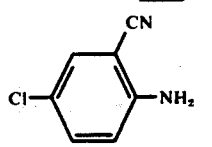 | " | reddish yellow | " | " |
| 105 | 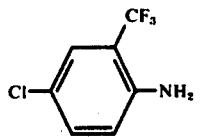 | " | " | " | " |
| 106 | 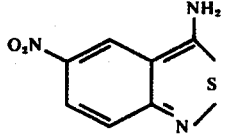 | " | reddish blue | reddish blue | |
| 107 | 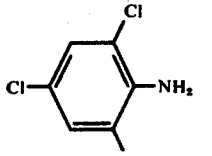 | " | — | reddish yellow | reddish yellow |
| 108 | 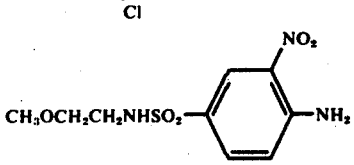 | " | — | yellowish red | yellowish red |

-continued

| 1 | 2 | 3 | 4 | 5 | 6 |
|---|---|---|---|---|---|
| 109 | C₂H₅OCH₂CH₂OOC-C₆H₃(NO₂)-NH₂ (ethoxyethyl 4-amino-3-nitrobenzoate) | " | — | yellowish red | yellowish red |
| 110 | ethyl 2-aminobenzothiazole-6-carboxylate | " | — | orange | orange |
| 111 | diethyl 2-amino-5-nitroterephthalate | " | — | red | red |
| 112 | 2-amino-5-phenyl-1,3,4-thiadiazole | " | — | reddish yellow | reddish yellow |
| 113 | 2-amino-5-nitrothiazole | Example 7 " | red violet | red violet | red violet |
| 114 | 2-amino-4-methyl-5-nitrothiazole | " | violet | violet | violet |
| 115 | CH₃OC(O)-CH₂CH₂-S-C(=N-)... (methoxycarbonylethylthio-thiadiazole derivative) | " | orange | orange | orange |
| 116 | 4-amino-7-nitrobenzotriazole | " | — | red | red |
| 117 | 4-amino-6-nitro-7-bromo-benzisothiazole (with CH₃) | " | — | blue violet | blue violet |
| 118 | ethyl 4-amino-3,5-dibromobenzoate | " | — | orange | orange |
| 119 | 2-amino-3-methyl-5-nitro-6-chloro... | " | — | red brown | red brown |
| 120 | 2-amino-4-nitro-... SO₂C₂H₄CO₂CH₃ | " | — | red | red |

-continued
| 1 | 2 | 3 | 4 | 5 | 6 |
|---|---|---|---|---|---|
| 121 | 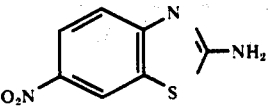 | " | — | orange red | orange red |
| 122 | 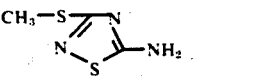 | " | — | orange | orange |
| 123 | 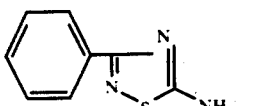 | " | — | " | " |
| 124 | 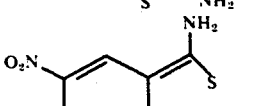 | Example 8 | | blue violet | blue violet |
| 125 | 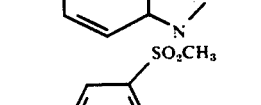 | " | | red | red |
| 126 | 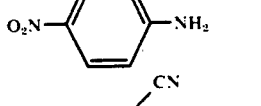 | " | | bluish red | bluish red |
| 127 | 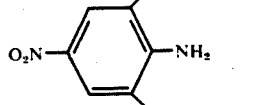 | " | | red | red |
| 128 | 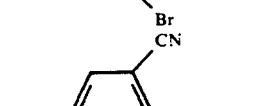 | " | | red | red |
| 129 | 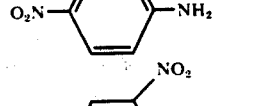 | " | | violet | violet |
| 130 | 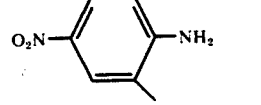 | " | | red | red |
| 131 | 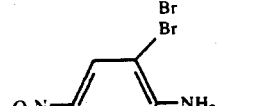 | " | | red | red |
| 132 | 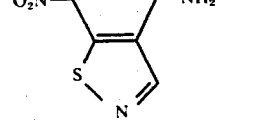 | " | | yellow | yellow |

| 1 | 2 | 3 | 4 | 5 | 6 |
|---|---|---|---|---|---|
| 133 | aniline (C6H5-NH2) | Example 7 | — | yellow | yellow |
| 134 | 4-methylaniline (CH3-C6H4-NH2) | " | — | yellow | yellow |
| 135 | 4-chloroaniline (Cl-C6H4-NH2) | " | — | " | " |
| 136 | N-(2-hydroxyethyl)-3-aminophthalimide | " | — | " | " |
| 137 | N-(2-hydroxyethyl)-4-aminophthalimide | " | — | " | " |
| 138 | 4-acetamidoaniline (CH3-CO-NH-C6H4-NH2) | " | — | yellow | yellow |
| 139 | aminocoumarin derivative | Example 8 | — | " | " |
| 140 | 4-chloroaniline (Cl-C6H4-NH2) | " | — | " | " |
| 141 | diethyl 2-aminoterephthalate | " | — | " | " |
| 142 | dimethyl 2-aminoterephthalate | " | — | " | " |
| 143 | 3-amino-5-nitro-1H-indazole | " | — | " | " |

| 1 | 2 | 3 | 4 | 5 | 6 |
|---|---|---|---|---|---|
| 144 | CH₃OCH₂CH₂—N attached to phthalimide-like bicyclic system with NH₂; CONH₂, CH₃ on pyridine with 2-NHR², 6-NHR¹ (analogous to Ex. 8) R¹,R² = —CH₂CH₂OH, —CH₂CH₂CH₂OCH₃, —C₆H₁₃(n) | " | — | " | " |
| 145 | 4-amino-5-bromo-7-nitrobenzisothiazole | " | — | blue | blue |
| 146 | 3-amino-5-nitro-2,1-benzisothiazole | " | blue | " | " |
| 147 | 2-amino-3-bromo-5-nitrobenzonitrile | " | violet | violet | violet |
| 148 | 2-amino-3-cyano-5-nitro | " | — | bluish red | bluish red |
| 149 | 2-amino-3-methylsulfonyl-5-nitro | " | — | " | " |
| 150 | 2-amino-3-bromo-5-nitro-(Br) | " | — | " | " |
| 151 | 2-amino-3-bromo-5-nitro (NO₂) | " | violet | violet | violet |
| 152 | 2-amino-3-nitro-5-nitro | " | — | bluish red | bluish red |

-continued

| 1 | 2 | 3 | 4 | 5 | 6 |
|---|---|---|---|---|---|
| 153 | 4-nitroaniline (O₂N–C₆H₃(NH₂)) | " | — | red | red |
| 154 | 2-chloro-4-nitroaniline | " | — | " | " |
| 155 | butyl 2-amino-5-nitrobenzoate (COOC₄H₉, NH₂, O₂N) | " | — | bluish red | bluish red |
| 156 | butyl 2-amino-3-bromo-5-nitrobenzoate (COOC₄H₉, NH₂, Br, O₂N) | " | — | " | " |
| 157 | 2,6-dichloro-4-nitroaniline | " | — | " | " |
| 158 | 2-amino-5-nitrothiazole-thiazole derivative | " | blue violet | blue violet | blue violet |
| 159 | CH₃OC(O)–CH₂CH₂–S– thiazolylamine | " | red | red | red |
| 160 | 3-phenyl-1,2,4-thiadiazol-5-amine | " | yellowish red | yellowish red | yellowish red |
| 161 | 2-amino-5-chlorobenzonitrile | " | orange | orange red | orange red |
| 162 | 2-amino-3-chloro-5-(methylsulfonyl)aniline (CH₃SO₂, NH₂, Cl) | " | orange | yellowish red | yellowish red |
| 163 | dimethyl 2-amino-5-nitroterephthalate (COOCH₃, NH₂, O₂N, COOCH₃) | " | bluish red | bluish red | bluish red |
| 164 | 5-amino-2-cyano-4-chloro-nitrobenzene (NO₂, NH₂, N≡C, Cl) | " | " | " | " |

-continued

| 1 | 2 | 3 | 4 | 5 | 6 |
|---|---|---|---|---|---|
| 165 | 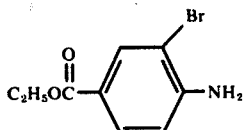 | " | red | red | red |
| 166 | 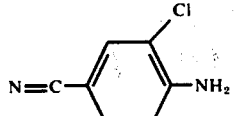 | " | orange | orange | orange |
| 167 | 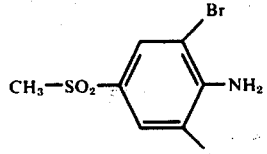 | " | — | red | red |
| 168 | 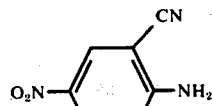 | R¹, R² = $-\!\!\!\!$⟨benzene⟩$-$CH₂CH₂OH<br>—CH₂CH₂CH₂OCH₃ | — | bluish red | bluish red |
| 169a | 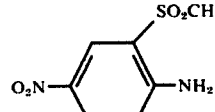 | R¹, R² = $-\!\!\!\!$⟨benzene⟩$-$CH₃<br>—CH₂CH₂CH₂OH | — | violet | violet |
| 169b | 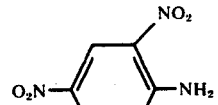 | R¹, R² = —CH₂CHCH₃,<br>            OH<br>—CH₂CH₂OH | — | reddish blue | reddish blue |
| 170 | 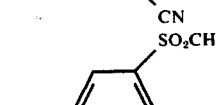 | R¹, R² = $-\!\!\!\!$⟨benzene⟩$-$OCH₃<br>—CH₂CH₂CH₂OCH₃ | — | violet | violet |
| 171 | 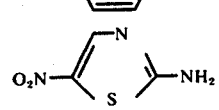 | " | blue violet | blue violet | blue violet |
| 172 | 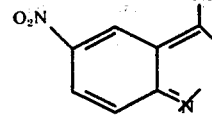 | R¹, R² = ⟨cyclohexyl⟩H<br>—CH₂CH₂OH | — | blue | blue |
| 173 | 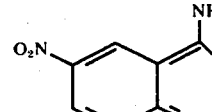 | R¹, R² = —CH₂CHCH₂CH₂CH₂CH₃<br>           CH₂—CH₃<br>—CH₂CH₂OH | — | blue | blue |
| 174 | 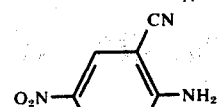 | " | — | violet | violet |
| 175 | " | R¹, R² = —CH₂CH₂OH | | violet | violet |
| 176 | 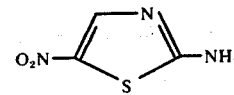 | R¹, R² = —C₆H₁₃(n)<br>—CH₂CH₂OCH₃ | | violet | violet |

| 1 | 2 | 3 | 4 | 5 | 6 |
|---|---|---|---|---|---|
| 177 | [structure: pyridine with CH3, CONH2, N-phenyl-CH2CH2OH, HOCH2CH2-NH substituents] | | | blue | blue |
| 178 | [structure: 2-amino-3-bromo-4,6-dinitrobenzene] NO2, NH2, Br, O2N | [pyridine structure with CH3, X1, X2, morpholino, HN—CH2CH2OH]; X1 = H, X2 = CN and X1 = CN, X2 = H | | bluish red | bluish red |
| 179 | [structure: 2-amino-3-cyano-5-nitrobenzene with Br] CN, NH2, O2N, Br | [pyridine structure with CH3, X1, X2, morpholino, HN—CH2CH2OH]; X1 = H, X2 = CONH2 and X1 = CONH2, X2 = H | | violet | violet |
| 180 | " | [pyridine with CH3, CN, NHR1, HN—R2]; R1, R2 = p-tolyl-CH2—, —CH2CH2OH | | bluish red | bluish red |
| 181 | " | [pyridine with CH3, CN, NH—R2, HN—R1]; R1, R2 = —CH2CH2—N(CH3)2, —CH2CH3 | red | red | red |
| 182 | " | R1, R2 = H; —CH2CH2N(C2H5)2 | | | |
| 183 | [structure: 2-amino-5-nitro-benzene with SO2CH3] SO2CH3, O2N, NH2 | [pyridine with CH3, CONH2, NH—R2, HN—R1]; R1, R2 = —CH2CH2N(C2H5)2, —CH2CH2CH2OCH3 | red | red | red |
| 184 | [structure: 2-amino-5-nitro-benzene with SO2CH3] SO2CH3, O2N, NH2 | [pyridine with CH3, CN, NH—R2, H—N—R1]; R1, R2 = —CH2CH2NH2, —CH2CH2OCH3 | yellowish red | yellowish red | yellowish red |

EXAMPLE 185

20 parts of the dye mixture (Example 57) having the formula:

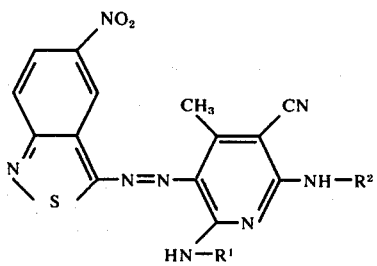

in which $R^1$ and $R^2$ denote the radicals $-CH_2-CH_2-O-CH_3$ and $-C_6H_{13}(n)$ is gradually added at 40° to 60° C with stirring to 100 parts of 85 to 90% sulfuric acid. Stirring is continued for 5 to 8 hours at 60° to 90° C. The whole is then allowed to cool and the solution is poured while stirring onto a mixture of 300 parts of ice and 250 parts of ice-water; the deposited dye mixture is filtered off, washed with water until it is neutral and dried. From 15 to 18 parts of a black powder is obtained of the formula:

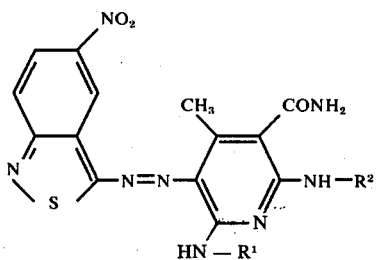

The powder dissolves in dimethylformamide with a blue color and dyes polycaprolactam and polyethylene terephthalate blue shades.

EXAMPLE 186

100 parts of polyethylene terephthalate is treated for ninety minutes at a temperature of 100° C in a dye liquor consisting of 3000 parts of water, 9 parts of finely divided o-phenylphenol and 0.3 part of the dye from Example 104. The fabric thus dye yellow is then washed with water followed by reductive cleaning for fifteen minutes in a liquor consisting of 3000 parts of water, 3 parts of sodium dithionite and 3 parts of 32% caustic soda solution, again washed with water and dried.

EXAMPLE 187

100 parts of a cloth of secondary cellulose acetate is dyed for 60 minutes at 80° C in a liquor consisting of 3000 parts of water, 1 part of the dye mixture from Example 113 and 3 parts of the reaction product of 1 mole of castor oil with 40 moles of ethylene oxide. A red violet dyeing is obtained.

EXAMPLE 188

100 parts of polyester fibers are dyed as usual with 1 part of the dye specified in Example 150 for one hour at 130° to 135° C in a pressure vessel. The material is then reductively purified in a liquor consisting of 3000 parts of water, 5 parts of sodium dithionite and 5 parts of 25% caustic soda solution for fifteen minutes at 80° to 85° C and then washed with water. A full red brown dyeing is obtained on the polyester fibers. The dyeing is distinguished by excellent fastness to light and good wet fastness.

EXAMPLE 189

100 parts of polyamide cloth is dyed for ninety minutes at 95° to 100° C in a liquor containing 1 part of the dye prepared according to Example 12 in finely divided form and 2 parts of sulfonated sperm oil alcohol in 2000 parts of water. The golden yellow dyeing obtained has good light and wet fastness properties.

EXAMPLE 190

20 parts of p-aminoazobenzene is stirred for several hours at room temperature with 120 parts of water and 0.2 part of the reaction product of oleylamine with about 12 moles of ethylene oxide, 40 parts by volume of 10N hydrochloric acid is added and the whole is made up to 800 parts by volume with ice and water and then at 15° C parts by volume of a 23% solution of sodium nitrite is added and the whole is stirred for two hours at the same temperature. Excess nitrous acid is destroyed in the usual way.

A solution of 25 parts of 2,6-di-β-hydroxyethylamino-3-cyano-4-methylpyridine in 500 parts of water and 25 parts by volume of 10N hydrochloric acid is allowed to flow into the resultant diazonium salt mixture at 10° C. 200 parts of a 55% solution of sodium acetate is then added gradually to the coupling mixture. After the coupling is over, the dye obtained is suction filtered, washed with water and dried at 80° C. A red powder is obtained which dissolves in dimethylformamide with a yellowish red color. Scarlet shades of good color strength and with excellent fastness properties are obtained on fibers of polyterephthalic acid glycol ester.

When equivalent amounts of the diazo components and coupling components set out in the following Table are used and the procedure of the above Example is followed, dyes having similar fastness properties are obtained.

| Ex. No | Diazo component | Coupling component | Shade of dyeing on Polyester | Polyamide |
|---|---|---|---|---|
| 191 | (structure shown) | (structure shown) | yellowish red | yellowish red |

| Ex. No | Diazo component | Coupling component | Shade of dyeing on Polyester | Polyamide |
|---|---|---|---|---|
| 192 | 4-CH₃-C₆H₄-N=N-(2-CH₃-4-NH₂-C₆H₃) | " | " | " |
| 193 | 4-Cl-C₆H₄-N=N-(2-CH₃-4-NH₂-C₆H₃) | " | red | red |
| 194 | C₆H₅-N=N-(2,5-di-CH₃-4-NH₂-C₆H₂) | " | red | red |
| 195 | 4-Cl-C₆H₄-N=N-(2,5-di-CH₃-4-NH₂-C₆H₂) | " | red | red |
| 196 | 4-O₂N-C₆H₄-N=N-(2-CH₃-4-NH₂-5-OCH₃-C₆H₂) | " | claret | claret |
| 197a | 4-O₂N-C₆H₄-N=N-C₆H₄-NH₂ | " | violet | violet |
| 197b | C₆H₅-N=N-(2-CH₃-4-NH₂-5-OCH₃-C₆H₂) | " | red | red |
| 198 | 4-O₂N-C₆H₄-N=N-(2-OCH₃-4-NH₂-5-OCH₃-C₆H₂) | " | violet | violet |
| 199 | C₆H₅-N=N-(3-OC₂H₅-4-NH₂-naphthyl) | " | currant | currant |

-continued
| Ex. No | Diazo component | Coupling component | Shade of dyeing on Polyester | Polyamide |
|---|---|---|---|---|
| 200 | 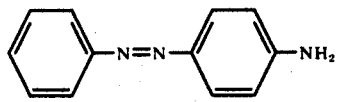 | 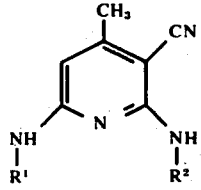 R¹ CH₂CH₂OCH₃ R² CH₂CH₂OH | yellowish red | yellowish red |
| 201 | 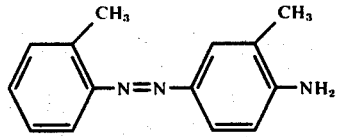 | " | " | " |
| 202 | 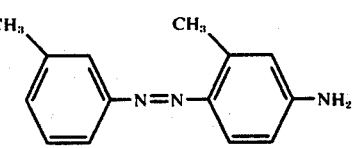 | " | " | " |
| 203 | 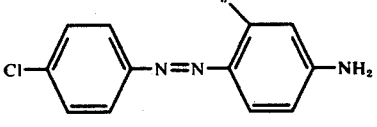 | " | red | red |
| 204 | 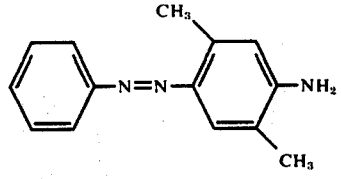 | " | red | red |
| 205 | 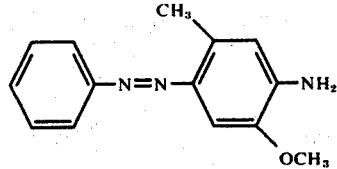 | " | red | red |
| 206 | 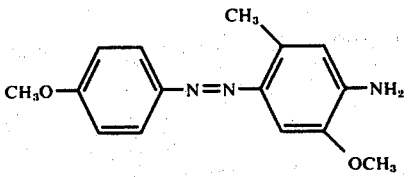 | " | red | red |
| 207 | 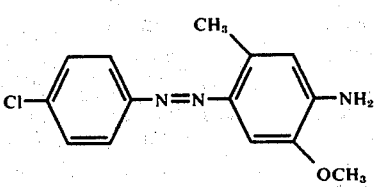 | " | red | red |
| 207a | 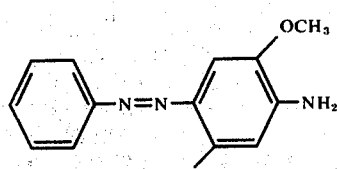 | " | claret | claret |

| Ex. No | Diazo component | Coupling component | Shade of dyeing on Polyester | Polyamide |
|---|---|---|---|---|
| 207b | [structure: CH₃(CH₃-CO)N-C₆H₄-N=N-C₆H₂(CH₃)(OCH₃)-NH₂] | " | red | red |

EXAMPLE 208

A mixture consisting of a solution of 23 parts of 4'-hydroxy-2'-methyl-4-aminoazobenzene in 500 parts by volume of a 1% caustic soda solution and 30 parts by volume of a 23% sodium nitrite solution is allowed to flow over one hour at 0° to 5° C into a mixture of 40 parts by volume of 10N hydrochloric acid, 400 parts of ice, 6 parts by volume of 23% sodium nitrite solution and 4 parts of the reaction product of oleylamine with about 12 moles of ethylene oxide. The whole is stirred for another two hours at 0° to 5° C and then the excess of nitrous acid is destroyed in the usual way.

A solution of 32 parts of 2,6-di-β-methoxyethylamino-3-cyano-4-methylpyridine in 400 parts of water and 12 parts by volume of a saturated sodium acetate solution is allowed to flow into the resultant mixture at 0° to 5° C. After coupling is over, the dye is isolated by suction filtration, washed with water and dried at 80° C. The red powder thus obtained dissolves in 80% acetone with a yellowish red color. Scarlet shades of a high level of fastness are obtained therewith on polyester or polyamide textile material.

When the compounds given in the following Examples are used instead of the said components, dyes having similar properties are obtained.

| Ex. No. | Diazo component | Coupling component | Shade of dyeing on polyester | polyamide |
|---|---|---|---|---|
| 209 | HO-C₆H₃(CH₃)-N=N-C₆H₄-NH₂ | [pyridine with CH₃, CN, and R₁-HN, NH-R₂ substituents]  R₁,R₂ = —(CH₂)₃—O—CH₃ | yellowish red | yellowish red |
| 210 | " | R₁,R₂ = —C₄H₉(n) | " | " |
| 211 | " | R₁,R₂ = —CH₂—CH₂—OH, —CH₂—CH₂—O—CH₃ | " | " |
| 212 | " | R₁,R₂ = —CH₂—CH₂—OCH₃, —CH₂—CH₂—OH | " | " |
| 213 | " | R₁,R₂ = [cyclohexyl-H] | " | " |
| 214 | " | R₁,R₂ = —CH₂—CH₂—OH, —CH₂-phenyl | " | " |
| 215 | " | R₁,R₂ = —CH₂—CH₂—OH, —(CH₂)₃—O—CH(CH₃)₂ | " | " |
| 215a | " | R₁,R₂ = —CH₂—CH₂—OH, —C₆H₄—CH₃ \| —CH₂—CH₂—OH | " | " |

EXAMPLE 216

32 parts of nitrosylsulfuric acid 40%) is added at 15° C to a solution of 35.5 parts of 3,5-dibromo-4-aminoazobenzene in 600 parts by volume of glacial acetic acid and the whole is stirred at the same temperature for another 2 hours. Excess nitrosylsulfuric acid is then destroyed in the usual way by adding urea.

A solution of 25 parts of 2,6-di-(β-hydroxyethylamino)-3-cyano-4-methylpyridine in 250 parts of glacial acetic acid is added to the diazo solution at 15° to 20° C. After coupling is over, such an amount of water is added to the reaction mixture that the dye crystallizes out. After suction filtration and washing with water, a brown powder is obtained which dissolves in dimethylformamide with a red color. Red dyeings with outstanding fastness properties are obtained on polyester fibers with the dye.

With the same diazo component and with equivalent amounts of the coupling components given in the following Table, dyes are obtained which give red shades having similar tinctorial properties.

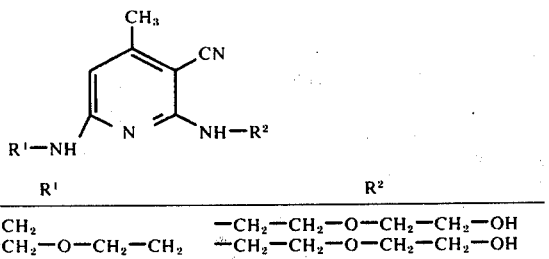

| | R¹ | R² |
|---|---|---|
| EXAMPLE 217 | HO—CH₂—CH₂ | —CH₂—CH₂—O—CH₂—CH₂—OH |
| EXAMPLE 218 | HO—CH₂—CH₂—O—CH₂—CH₂ | —CH₂—CH₂—O—CH₂—CH₂—OH |

EXAMPLE 219

A mixture of 56 parts of 2,6-dichloro-3-cyano-4-methylpyridine, 27 parts of β-hydroxyethylamine, 33 parts of β-methoxyethylamine and 33 parts of β-hydroxypropylamine is stirred for 2 hours at 150° C. The reaction mixture is poured into a mixture of 1000 parts of ice-water and 100 parts by volume of 10N hydrochloric acid. The pH is adjusted to 3.5 to 4 by adding 150 parts by volume of 55% sodium acetate solution and the aqueous phase is shaken up three times, each time with 500 parts by volume of ethyl acetate. The combined ester extracts are dried with anhydrous sodium sulfate and the ester is distilled off from the filtrate. 66 parts of a viscous oil remains.

A solution of 28 parts of this product in 300 parts by volume of dimethylformamide is allowed to flow slowly into the diazonium salt solution obtained from 20 parts of 4-aminoazobenzene according to Example 190 at 5° to 10° C. The pH is raised to 3 to 4 by gradually adding 300 parts by volume of 55% sodium acetate solution. The dye thus obtained is isolated by suction filtration, washed with water and dried at 80° C. It is obtained as a red powder which is soluble in 80% aqueous acetone with a yellowish red color and it dyes polyester and polyamide fibers scarlet shades having excellent fastness properties.

When the aminoazobenzenes set out in the following Table are used with the same coupling component, dyes having similar properties are obtained.

| EXAMPLE | Diazo component | Shade of dyeing on polyester | polyamide | acetate |
|---|---|---|---|---|
| 220 | CH₃–⟨⟩–N=N–⟨⟩(CH₃)–NH₂ | yellowish | yellowish | |
| 221 | CH₃–⟨⟩–N=N–⟨⟩(CH₃)–NH₂ (red, red) | yellowish | yellowish | |
| 222 | HO–⟨⟩(CH₃)–N=N–⟨⟩(CH₃)–NH₂ (red, red) | yellowish | yellowish | yellowish |
| 223 | HO–⟨⟩–N=N–⟨⟩–NH₂ (red, red) | yellowish | yellowish | |
| 224 | HO–⟨⟩(CH₃)–N=N–⟨⟩–NH₂ (red) | yellowish | yellowish | |
| 225 | CL–⟨⟩–N=N–⟨⟩(CH₃)–NH₂ (red, red) | red | red | red |

-continued

| EXAMPLE | Diazo component | Shade of dyeing on | | |
|---|---|---|---|---|
| | | polyester | polyamide | acetate |
| 226 | [phenyl-N=N-(2,5-dimethyl-4-amino)phenyl] | red | red | |
| 227 | [4-methyl-2-hydroxyphenyl-N=N-(4-amino)phenyl] | red | red | |
| 228 | [phenyl-N=N-(5-methyl-2-methoxy-4-amino)phenyl] | red | red | |
| 229 | [4-methoxyphenyl-N=N-(2-methyl-5-methoxy)phenyl] | red | red | |
| 230 | [phenyl-N=N-(2-methoxy-5-methoxy-4-amino)phenyl] | claret | claret | |

EXAMPLE 231

1000 parts by volume of a 2.5% aqueous solution of 2-hydroxyethyl-6-aminoethyl-3-cyano-4-methylpyridine is added at 5° to 10° C to the diazonium salt solution obtainable from 20 parts of 4-aminoazobenzene according to Example 190. Coupling is completed by adding 300 parts by volume of a saturated sodium acetate solution. The dye thus obtained is isolated by suction filtration, washed with water and dried. A yellow brown powder is obtained which dissolves in hot water with an orange color. Dyeings prepared therewith on acrylonitrile polymers are orange and have very good fastness properties.

When the derivatives of 4-aminoazobenzene set out in the following Table are used as diazo components instead of 4-aminoazobenzene, dyes having similar tinctorial properties are obtained.

| EXAMPLE | Diazo component | Shade of dyeing of acrylonitrile polymers |
|---|---|---|
| 232 | [2-methylphenyl-N=N-(2-methyl-4-amino)phenyl] | orange |
| 233 | [3-methylphenyl-N=N-(2-methyl-4-amino)phenyl] | orange |
| 234 | [phenyl-N=N-(2,5-dimethyl-4-amino)phenyl] | yellowish red |
| 235 | [4-chlorophenyl-N=N-(2-methyl-4-amino)phenyl] | yellowish red |

-continued

| EXAMPLE | Diazo component | Shade of dyeing of acrylonitrile polymers |
|---|---|---|
| 236 | [phenyl-N=N-(2-methyl-4-methoxy-5-amino)phenyl] | red |
| 237 | [phenyl-N=N-(2,5-dimethoxy-4-amino)phenyl] | claret |

| EX. | Diazo component | Coupling component | Shade of dyeing on polyamide | Shade of dyeing on polyester |
|---|---|---|---|---|
| 238 | [phenyl-N=N-(2-methyl-5-methoxy-4-amino)phenyl] | 4-methyl-3-cyano-2,6-bis(NHR)pyridine; $R^1, R^2 = CH_2-CH_2-O-CH_3$, $CH_2-CH_2-OH$ | red | red |
| 239 | $CH_3-CO-NH$-[phenyl-N=N-(2-methyl-5-methoxy-4-amino)phenyl] | 4-methyl-3-cyano-2,6-bis(NHR)pyridine; $R^1, R^2 = CH_2-CH_2-O-CH_3$, $CH_2-CH_2-OH$ | claret | claret |
| 240 | [phenyl-N=N-(4-amino)phenyl] | $R^1, R^2 = CH_2-CH_2-OH$, $CH_2-CH_2-O-CH_2-CH_2-OH$ | yellowish red | yellowish red |
| 241 | $O_2N$-[phenyl-N=N-(2-methyl-5-methoxy-4-amino)phenyl] | $R^1, R^2 = CH_2-CH_2-OH$, $CH_2-CH_2-O-CH_2-CH_2-OH$ | violet | violet |
| 242 | $Cl$-[phenyl-N=N-(2-methyl-4-amino)phenyl] | $R^1, R^2 = CH_2-CH_2-OH$, $CH_2-CH_2-O-CH_2-CH_2-OH$ | red | red |
| 243 | [phenyl-N=N-(2,6-dimethyl-4-amino)phenyl] | $R^1, R^2 = CH_2-CH_2-OH$, $CH_2-CH_2-O-CH_2-CH_2-OH$ | yellowish red | yellowish red |
| 244 | [phenyl-N=N-(4-amino)phenyl] | $R^1, R^2 = CH_2-CH_2-O-CH_2-CH_2-OH$ | yellowish red | yellowish red |
| 245 | [2-methylphenyl-N=N-(3-methyl-4-amino)phenyl] | $R^1, R^2 = N\begin{subarray}{l}CH_3\\CH_2-CH_2-OH\end{subarray}$ | yellowish red | yellowish red |
| 246 | [phenyl-N=N-(4-amino)phenyl] | 4-methyl-3-cyano-2,6-bis(NHR)pyridine; $R^1, R^2 = (CH_2)_3OCH_3$ | yellowish red | yellowish red |

| Ex. | Diazo component | Coupling component | Shade of dyeing on polyamide | Shade of dyeing on polyester |
|---|---|---|---|---|
| 247 | phenyl-N=N-(2,5-dimethoxy)-4-NH₂-phenyl | CH₃, CN-substituted pyridine with R¹HN and NHR²; R¹, R² = (CH₂)₃OCH₃ | claret | claret |
| 248 | H₂N—SO₂—C₆H₄—N=N—(2-CH₃, 5-OCH₃)-4-NH₂-phenyl | R¹, R² = n-C₃H₉ | red | red |
| 249 | phenyl-N=N-(2,5-dimethoxy)-4-NH₂-phenyl | R¹, R² = n-C₄H₉ | claret | claret |
| 250 | phenyl-N=N-(2,5-dimethoxy)-4-NH₂-phenyl | R¹, R² = (CH₂)₃—O—CH(CH₃)₂ ; CH₂—CH₂—OH | claret | claret |
| 251 | phenyl-N=N-C₆H₄-NH₂ | R¹, R² = (CH₂)₃—O—CH(CH₃)₂ ; CH₂—CH₂—OH | yellowish red | yellowish red |
| 252 | phenyl-N=N-C₆H₄-NH₂ | R¹, R² = cyclohexyl(H) ; —CH₂—CH₂—OH | yellowish red | yellowish red |
| 253 | phenyl-N=N-(2-CH₃, 5-OCH₃)-4-NH₂-phenyl | R¹, R² = cyclohexyl(H) ; —CH₂—CH₂—OH | yellowish red | yellowish red |
| 254 | phenyl-N=N-C₆H₄-NH₂ | CH₃, CN-substituted pyridine; R¹, R² = CH₂—CH(OH)—CH₃ | yellowish red | yellowish red |
| 255 | phenyl-N=N-(2,5-dimethyl)-4-NH₂-phenyl | CH₃, CN-substituted pyridine; R¹, R² = CH₂—CH(OH)—CH₃ | red | red |
| 256 | phenyl-N=N-(2,5-dimethyl)-4-NH₂-phenyl | CH₃, CN-substituted pyridine; R¹, R² = CH₂—CH(OH)—CH₃ | red | red |

| EX. | Diazo component | Coupling component | Shade of dyeing on polyamide | polyester |
|---|---|---|---|---|
| 257 | 4-Cl-C₆H₄-N=N-C₆H₃(CH₃)-NH₂ | 4-methyl-3-cyano-2,6-bis(NH-R)-pyridine; R¹, R² = CH₂-CH(OH)-CH₃ | red | red |
| 258 | C₆H₅-N=N-C₆H₂(OCH₃)(CH₃)-NH₂ | 4-methyl-3-cyano-2,6-bis(NH-R)-pyridine; R¹, R² = CH₂-CH(OH)-CH₃ | red | red |
| 259 | 4-CH₃O-C₆H₄-N=N-C₆H₂(OCH₃)(CH₃)-NH₂ | 4-methyl-3-cyano-2,6-bis(NH-R)-pyridine; R¹, R² = CH₂-CH(OH)-CH₃ | red | red |
| 260 | C₆H₅-N=N-C₆H₂(OCH₃)₂-NH₂ | 4-methyl-3-cyano-2,6-bis(NH-R)-pyridine; R¹, R² = CH₂-CH(OH)-CH₃ | claret | claret |
| 261 | C₆H₅-N=N-C₆H₄-NH₂ | 4-methyl-3-carboxamido-2,6-bis(NH-R)-pyridine; R¹, R² = CH₂-CH₂-OH, CH₂-CH(OH)-CH₃, CH₂-CH₂-OCH₃ | red brown | red brown |
| 262 | C₆H₅-N=N-C₆H₄-NH₂ | R¹, R² = CH₂-CH₂-OH | red brown | red brown |
| 263 | C₆H₅-N=N-C₆H₄-NH₂ | R¹, R² = CH₂-CH₂-OH, CH₂-CH₂-OCH₃ | red brown | red brown |
| 264 | O₂N-C₆H₄-N=N-C₆H₂(CH₃)(OCH₃)-NH₂ | R¹, R² = CH₂-CH₂-OH, CH₂-CH₂-OCH₃ | blue | blue |
| 265 | O₂N-C₆H₄-N=N-C₆H₂(CH₃)(OCH₃)-NH₂ | R¹, R² = CH₂-CH₂-OH | blue | blue |
| 266 | O₂N-C₆H₄-N=N-C₆H₂(OCH₃)₂-NH₂ | R¹, R² = CH₂-CH₂-OH | blue | blue |

-continued

| EX. | Diazo component | Coupling component | Shade of dyeing on polyamide | polyester |
|---|---|---|---|---|
| 267 | $O_2N-\bigcirc-N=N-\bigcirc(OCH_3)(OCH_3)-NH_2$ | $R^1, R^2 = CH_2-CH_2-OH$<br>$CH_2-CH-CH_3$<br>$\quad\quad\quad\mid$<br>$\quad\quad\quad OH$<br>$CH_2-CH_2-OCH_3$ | blue | blue |

Other dyes are obtained by the methods described in the Examples from the components in the following Table:

PCL = polycaprolactam; PETP = polyethylene terephthalate.

| EXAMPLE | Diazo component | Coupling component | Shade of dyeing on acetate | PCL | PETP |
|---|---|---|---|---|---|
| 268 | $O_2N-\bigcirc(CN)(Br)-NH_2$ | $CH_3-\bigcirc(CONH_2)(NH-R)-N=\,$, $H-N-R$<br>$R^1,R^2 = -CH_2-CH-CH_3$<br>$\quad\quad\quad\quad\mid$<br>$\quad\quad\quad\quad OH$ | red violet | violet | violet |
| 269 | " | $R^2 = -\bigcirc-O-CH_3$<br>$R^1 = -CH_2-CH_2-OH$ | — | reddish blue | reddish blue |
| 270 | $O_2N-\bigcirc(CN)-NH_2$ | $R^1,R^2 = -CH_2-CH_2-OH$<br>$-CH_2-CH-CH_3$<br>$\quad\quad\quad\mid$<br>$\quad\quad\quad OH$ | bluish red | bluish red | bluish red |
| 271 | " | $R^1,R^2 = -CH_2-CH-CH_3$<br>$\quad\quad\quad\mid$<br>$\quad\quad\quad OH$<br>$-CH_2-CH_2-CH_2-OCH_3$ | bluish red | bluish red | bluish red |
| 272 | $O_2N-\bigcirc(COOCH_3)-NH_2$ | " | bluish red | bluish red | bluish red |
| 273 | $O_2N-\bigcirc(NO_2)-NH_2$ | " | bluish red | bluish red | bluish red |
| 274 | $O_2N-\bigcirc(Cl)-NH_2$ | " | pure red | red | red |
| 275 | $O_2N-\bigcirc(Br)(Br)-NH_2$ | " | bluish red | bluish red | bluish red |

-continued

| EXAMPLE | Diazo component | Coupling component | Shade of dyeing on acetate | PCL | PETP |
|---|---|---|---|---|---|
| 276 | 2-amino-5-nitro-phenyl with SO$_2$CH$_3$ (O$_2$N—C$_6$H$_3$(SO$_2$CH$_3$)—NH$_2$) | " | bluish red | bluish red | bluish red |
| 277 | 2-amino-5-nitro-phenyl with two COOCH$_3$ groups | " | bluish red | bluish red | bluish red |
| 278 | 5-phenyl-1,3,4-thiadiazol-2-amine | R$^1$,R$^2$ = CH$_2$—CH$_2$—OH; CH$_2$—CH(OH)—CH$_3$ | red | red | red |
| 279 | 3-amino-5-nitro-2,1-benzisothiazole | R$^1$ = —CH$_2$—CH$_2$—CH$_2$—OCH$_3$; R$^2$ = —CH$_2$—CH$_2$—OH | blue | greenish blue | pure blue |
| 280 | " | R$^1$ = —C$_8$H$_{17}$(i); R$^2$ = —CH$_2$—CH(OH)—CH$_3$ | — | " | " |
| 281 | " R$^1$ = —CH$_2$—CH(OH)—CH$_3$ | R$^2$ = —CH$_2$—CH$_2$—OH | blue | greenish blue | |
| 282 | " | R$^1$ = —C$_6$H$_4$—CH$_3$ (p-tolyl); R$^2$ = —CH$_2$—CH$_2$—OH | — | green blue | green blue |
| 283 | " | R$^2$ = —C$_6$H$_4$—O—CH$_3$ | — | " | " |

R$^1$ = —CH$_2$—CH$_2$—OH

| 284 | 2-amino-5-nitro-benzonitrile | mixture: pyridine with CH$_3$, CN, NH—R$^2$, HN—R$^1$; R$^1$,R$^2$ = —CH$_2$—CH$_2$—OH, —CH$_2$—CH$_2$—CH$_2$—OCH$_3$, —CH$_2$—CH(OH)—CH$_3$ | yellowish red | yellowish red | yellowish red |
| 285 | 2-amino-3-bromo-5-nitro-benzonitrile | " | red | red | red |

-continued

| EXAMPLE | Diazo component | Coupling component | Shade of dyeing on acetate | PCL | PETP |
|---|---|---|---|---|---|
| 286 | 2-amino-1,4-dinitrobenzene (NO₂, NH₂, O₂N) | " | — | red | red |
| 287 | 2-amino-4-bromo-1,nitro... (NO₂, NH₂, Br, O₂N) | " | — | red | red |
| 288 | 2-amino-4-nitro-methylsulfonyl benzene (SO₂CH₃, NH₂, O₂N) | " | — | yellow-ish red | yellow-ish red |
| 289 | 3-amino-5-nitrobenzisothiazole | X = —CONH₂<br>R² = —C₆H₄—O—C₂H₄OH<br>R¹ = —CH₂—CH—CH₃<br>            \|<br>           OH | — | blue green | blue green |
| 290 | 3-amino-7-bromo-5-nitrobenzisothiazole | X = —CONH₂<br>R¹ = —CH₂—CH—CH₃<br>            \|<br>           OH<br>R² = —CH₂—CH₂—OH | — | greenish blue | greenish blue |
| 291 | 3-phenyl-5-amino-1,2,4-thiadiazole | X = —CONH₂<br>R¹ = —CH₂—CH₂—OH<br>R² = —CH₂—CH—CH₃<br>            \|<br>           OH | red | red | red |
| 292 | " | X = —CONH₂<br>R¹ = —CH₂—CH₂—CH₃<br>R² = —CH₂—CH₂—OH | — | red | red |
| 293 | " | X = —CONH₂<br>R¹ = —CH₂—CH—CH₃<br>R² = —CH₂—CH₂—OH | red | red | red |
| 294 | 2-amino-5-nitrothiazole<br>X = —CONH₂<br>R¹,R² = —CH₂—CH—CH₃<br>                    \|<br>                   OH<br>—CH₂—CH₂—CH₂—OCH₃ | | violet | violet | violet |
| 295 | 2-amino-5-nitro-benzonitrile (CN, NH₂, O₂N) | X = —CONH₂<br>R¹ = —CH₂—CH₂—OH<br>R² = —CH₂—CH₂—N(morpholine-SO₂) | — | red | red |

-continued

| EXAMPLE | Diazo component | Coupling component | Shade of dyeing on acetate | PCL | PETP |
|---|---|---|---|---|---|
| 296 | (structure: benzothiazole with CN, NH$_2$, O$_2$N substituents) | X = —CONH$_2$<br>R$^1$ = —CH$_2$—CH$_2$—OH<br>R$^2$ = —CH$_2$—CH—CH$_3$ | — | reddish blue | reddish blue |

EXAMPLE 297

64 parts of 2,6-dichloro-3-carboxamido-4-methyl-pyridine is stirred with 80 parts of n-butylamine for seven hours at 80° to 95° C. Then 60 parts of β-hydroxyethylamine is added and excess butylamine is distilled off. The residue is stirred for 5 to 7 hours at 150° to 170° C and allowed to cool. 100 parts of dimethylformamide and then a mixture of 900 parts of water and 80 parts by volume of 36% hydrochloric acid are added. After cooling to 0° C, 41 parts of a diazotized solution of 2-chloro-4-nitroaniline prepared in the usual way is added to this mixture and then sodium acetate solution is added until the pH is 2.5 After coupling is over, the deposited dye is suction filtered. It has the formula:

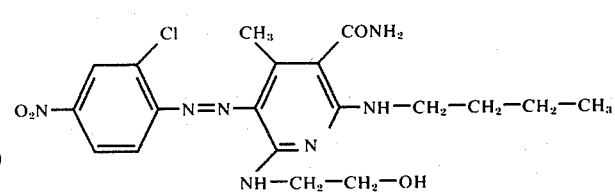

It is washed with water and dried. A red brown powder is obtained which dissolves in dimethylformamide with a bluish red color and dyes polyethylene terephthalate cloth and also acetate silk red shapes. The full dyeings have very good allround fastness properties.

| EXAMPLE | Diazo component | Coupling component | Shade of dyeing on PETP |
|---|---|---|---|
| 298 | (benzene with CN, NH$_2$, Br, O$_2$N) | X = CONH$_2$<br>R,R$^1$ = H<br>R$^2$ = CH$_2$—CH—CH$_3$<br>              \|<br>              OH<br>R$^3$ = H | red |
| 299 | " | X = —CONH$_2$<br>R = H<br>R$^1$ = CH$_2$—CH$_2$—OH<br>R$^2$ = —C$_4$H$_9$(n)<br>R$^3$ = H | bluish red |
| 300 | (benzene with CN, NH$_2$, O$_2$N) | X = —CONH$_2$<br>R = H<br>R$^1$ = CH$_2$—CH$_2$—OH<br>R$^2$ = —C$_4$H$_9$(n)<br>R$^3$ = H | red |
| 301 | (benzene with COOCH$_3$, NH$_2$, O$_2$N) | X = —CONH$_2$<br>R = H<br>R$^1$ = CH$_2$—CH$_2$—OH<br>R$^2$ = —C$_4$H$_9$(n)<br>R$^3$ = H | red |
| 302 | (benzene with Br, NH$_2$, O$_2$N) | " | red |
| 303 | (benzene with Cl, NH$_2$, Br, CH$_3$—SO$_2$—) | " | orange red |

EXAMPLE 304

150 parts of 2,6-dichloro-3-carboxamido-4-methyl-pyridine is stirred with 250 parts of 2-hydroxypropylamine for five hours at 80° to 95° C, then allowed to cool and 800 parts of ice-water is added. After acidification with hydrochloric acid to pH 6 to 4, the whole is stirred for another hour at 0° C and the precipitated product of the formula:

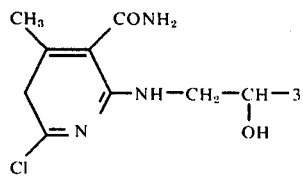

is suction filtered. It has a melting point of 140° C.

25 parts of this compound is heated with 50 parts of β-methoxyethylamine in an autoclave for five to seven hours at 150° to 170° C. The excess of amine is then distilled off and 150 parts of water and hydrochloric acid are added to the residue to set up a pH of 4. The mixture is then cooled to 0° C after which a solution of 16 parts of 2-amino-5-nitrobenzonitrile (diazotized as usual) is added. A pH of 2.5 is set up in the mixture with 50% sodium acetate solution and the precipitated dye of the formula

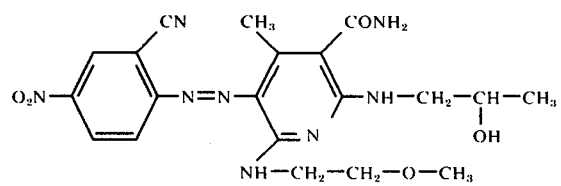

is isolated.

The red brown powder dissolves in dimethyl formamide with a bluish red color and dyes polyethylene terephthalate cloth bluish red shades. The dyeing has very good fastness to light, dry-heat pleating and setting, and washing.

EXAMPLE 305

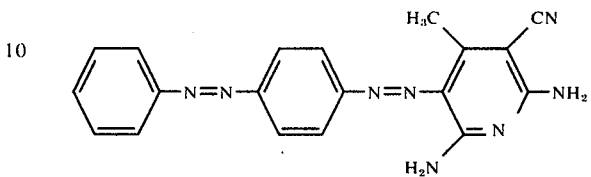

15 parts of 2,6-diamino-3-cyano-4-methylpyridine dissolved in a mixture of 15 parts by volume of 10N hydrochloric acid and 200 parts of water is introduced at 10° to 15° C into the diazo solution obtained according to Example 190. The whole is adjusted to pH 3 to 4 with 200 parts by volume of 55% sodium acetate solution to achieve a complete coupling. The isolated and dried dye, which is a brown yellow powder, dissolves in dimethylformamide with a reddish yellow color. Golden yellow dyeings having excellent fastness properties are obtained therewith on polyamide or polyester fibers.

The coupling component is obtained by reacting 94 parts of 2,6-dichloro-3-cyano-4-methylpyridine with 2000 parts by volume of 25% ammonia for five hours at 180° C in an autoclave. It has a melting point of 226° to 227° C.

The following dyes are obtained analogously to the foregoing Examples:

| EXAMPLE | Diazo component | Coupling component | Shade of dyeing on PETP |
|---|---|---|---|
| 306 | CH₃S-[thiadiazole]-NH₂ | 4-methyl-3-cyano-6-(NH-CH₂-CH(OH)-C₆H₅)-2-(HN-CH₂-CH₂-OH)-pyridine | orange |
| 307 | CH₃OC(O)-CH₂-CH₂-S-[thiadiazole]-NH₂ | 4-methyl-3-cyano-6-(NH-CH₂-CH₂-C₆H₅)-2-(HN-CH₂-CH₂-OH)-pyridine | orange |
| 308 | 4-nitro-2-chloroaniline | 4-methyl-3-cyano-6-(NH-CH₂-CH(OH)-CH₂-C₆H₅)-2-(HN-CH₂-CH₂-O-CH₂-CH₂-OH)-pyridine | yellowish red |
| 309 | 4-nitro-2-cyano-6-chloroaniline | 4-methyl-3-cyano-6-(NH-C₆H₄-CH₃)-2-(HN-CH₂-CH₂-OH)-pyridine | bluish red |

-continued
| EXAMPLE | Diazo component | Coupling component | Shade of dyeing on PETP |
|---|---|---|---|
| 310 | 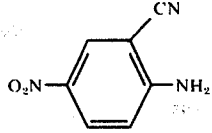 | 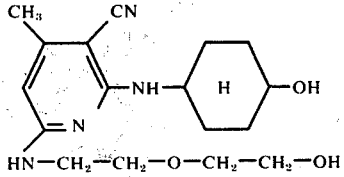 | red |
| 311 | 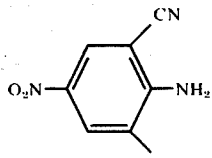 | 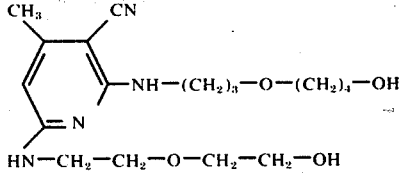 | bluish red |
| 312 | 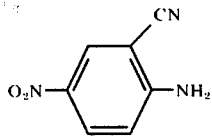 | 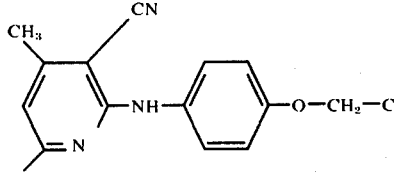 | bluish red |
| 313 | 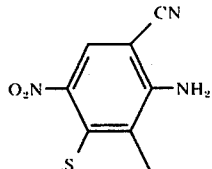 | 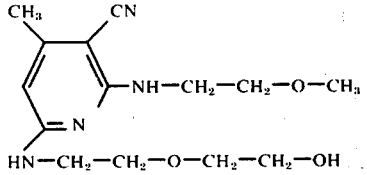 | violet |
| 314 | 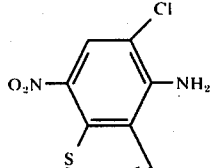 | '' | violet |
| 315 | 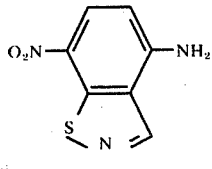 | '' | red violet |
| 316 | 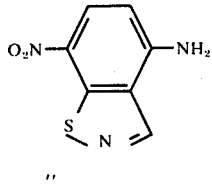 | '' | bluish red |
| 317 | '' | 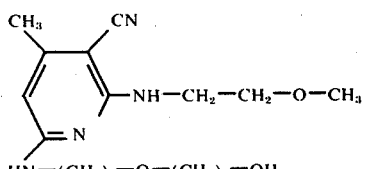 | bluish red |
| 318 | '' | 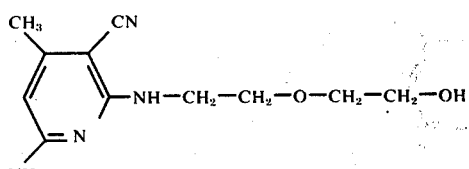 | red |

-continued

| EXAMPLE | Diazo component | Coupling component | Shade of dyeing on PETP |
|---|---|---|---|
| 319 | 4-amino-5-bromo-7-nitrobenzisothiazole | 4-methyl-3-cyano-6-[NH-(CH$_2$)$_3$-O-(CH$_2$)$_4$-OH]-2-[NH-CH$_2$-CH$_2$-CH$_2$-OH]-pyridine | violet |
| 320 | 4-nitroaniline | '' | orange |
| 321 | 2-amino-5-chlorobenzonitrile | '' | golden yellow |
| 322 | 2-chloro-4-nitroaniline | '' | yellowish red |
| 323 | 2-bromo-4-nitroaniline | '' | yellowish red |
| 324 | 2-amino-5-nitrobenzonitrile | '' | red |
| 325 | 2-amino-3-chloro-5-nitrobenzonitrile | '' | bluish red |
| 326 | 2-amino-5-nitro-(methylsulfonyl)benzene | '' | bluish red |
| 327 | 3-amino-5-nitrobenzisothiazole | '' | reddish blue |
| 328 | 3-amino-7-bromo-5-nitrobenzisothiazole | '' | blue |

-continued

| EXAMPLE | Diazo component | Coupling component | Shade of dyeing on PETP |
|---|---|---|---|
| 329 | 2-amino-1,5-dinitrobenzene (4-$O_2N$, 2-$NO_2$, 1-$NH_2$ benzene) | " | bluish red |
| 330 | 2-amino-3-bromo-1,5-dinitrobenzene (4-$O_2N$, 2-$NO_2$, 1-$NH_2$, 6-Br benzene) | " | bluish red |
| 331 | 3-amino-6-chloro-2-nitrobenzonitrile ($N{\equiv}C$-, 2-$NO_2$, 3-$NH_2$, 6-Cl benzene) | " | red |
| 332 | 2-amino-6-chloro-4-nitrobenzene (4-$O_2N$, 2-Cl, 1-$NH_2$ benzene) | 4-methyl-3-cyano-2-($NH{-}CH_2{-}CH_2{-}O{-}CH_3$)-6-($HN{-}(CH_2)_3{-}O{-}(CH_2)_4{-}OH$)-pyridine | yellowish red |
| 333 | 2-amino-5-nitrobenzonitrile | " | yellowish red |
| 335 | 2-amino-3-chloro-5-nitrobenzonitrile (CN, 4-$O_2N$, 2-$NH_2$, 6-Cl benzene) | " | bluish red |
| 336 | " | 4-methyl-3-cyano-2-($NH{-}CH_2{-}CH_2{-}O{-}CH_3$)-6-($HN{-}CH_2{-}CH_2{-}O{-}CH_2{-}CH_2{-}OH$)-pyridine | bluish red |
| 337 | 2-amino-6-nitrobenzothiazole (nitro-substituted aminobenzothiazole) | | red |
| 338 | 2-amino-3-bromo-5-nitrobenzonitrile (CN, 4-$O_2N$, 2-$NH_2$, 6-Br benzene) | " | bluish red |

-continued
| EXAMPLE | Diazo component | Coupling component | Shade of dyeing on PETP |
|---|---|---|---|
| 339 | 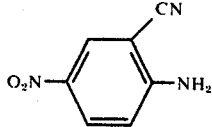 | 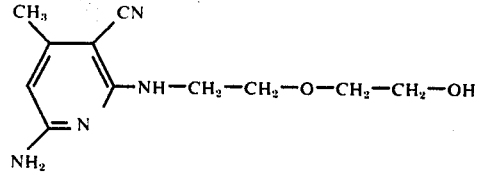 | yellowish red |
| 340 | 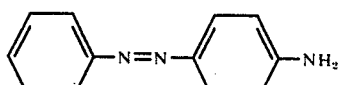 | '' | orange |
| 341 | 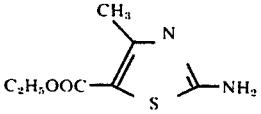 | 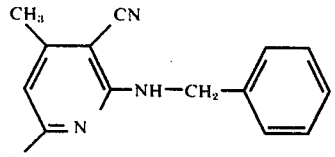 | yellowish red |
| 342 | 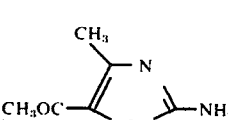 | 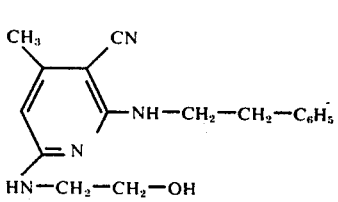 | red |
| 343 | 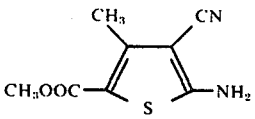 | '' | bluish red |
| 344 | 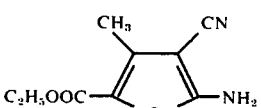 | 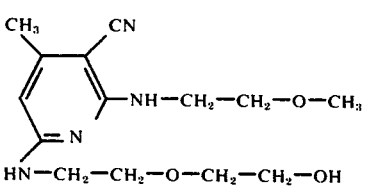 | bluish red |
| 345 | 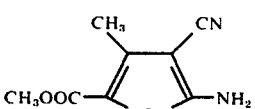 | '' | bluish red |
| 346 | 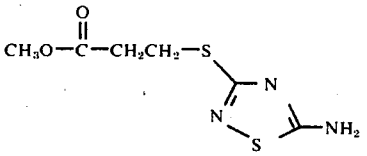 | 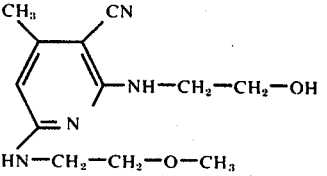 | orange (acetate: orange) |
| 347 | 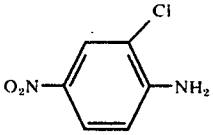 | 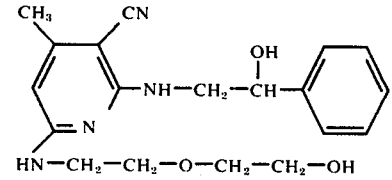 | yellowish red |
| 348 | 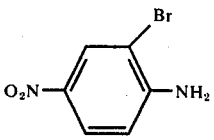 | '' | yellowish red |

-continued

| EXAMPLE | Diazo component | Coupling component | Shade of dyeing on PETP |
|---|---|---|---|
| 349 | 2-amino-3-chloro-5-nitrobenzonitrile (NO$_2$, CN, NH$_2$, Cl on benzene) | 3-cyano-4-methyl-6-(2-hydroxyethylamino)-2-(2-phenylethylamino)pyridine (CH$_3$, CN, NH—CH$_2$—CH$_2$—C$_6$H$_5$, HN—CH$_2$—CH$_2$—OH on pyridine) | bluish red |
| 350 | 2-aminobenzonitrile (CN, NH$_2$) | 3-cyano-4-methyl-2,6-bis(6-hydroxyhexylamino)pyridine (CH$_3$, CN, NH—(CH$_2$)$_6$—OH, NH—(CH$_2$)$_6$—OH) | yellow (polyamide: yellow) |
| 351 | 2-amino-3-bromo-5-nitroaniline (Br, NH$_2$, O$_2$N) | 3-cyano-4-methyl-2,6-bis[3-(4-hydroxybutoxy)propylamino]pyridine (CH$_3$, CN, NH—(CH$_2$)$_3$—O—(CH$_2$)$_4$—OH, NH—(CH$_2$)$_3$—O—(CH$_2$)$_4$—OH) | yellowish red |
| 352 | 2-aminobenzonitrile (CN, NH$_2$) | '' | yellow (polyamide: yellow) |
| 353 | 2-amino-5-chlorobenzonitrile (CN, NH$_2$, Cl) | 3-cyano-4-methyl-2,6-bis[3-(4-hydroxybutoxy)propylamino]pyridine (CH$_3$, CN, NH—(CH$_2$)$_3$—O—(CH$_2$)$_4$—OH, NH—(CH$_2$)$_3$—O—(CH$_2$)$_4$—OH) | yellow (polyamide: yellow) |
| 354 | 2-amino-3-nitro-5-nitrochlorobenzene (Cl, NH$_2$, O$_2$N, NO$_2$) | '' | yellowish red |
| 355 | 2-amino-3-nitro-5-nitrochlorobenzene (Cl, NH$_2$, O$_2$N, NO$_2$) | '' | |
| 356 | 2-amino-3-bromo-5-nitrobenzonitrile (CN, NH$_2$, O$_2$N, Br) | 3-cyano-4-methyl-2,6-bis(3-hydroxypropylamino)pyridine (CH$_3$, CN, NH—(CH$_2$)$_3$—OH, NH—(CH$_2$)$_3$—OH) | bluish red |
| 357 | 2-amino-5-chlorobenzonitrile (CN, NH$_2$, Cl) | 3-cyano-4-methyl-2,6-diaminopyridine (CH$_3$, CN, NH$_2$, NH$_2$) | yellow |

-continued

| EXAMPLE | Diazo component | Coupling component | Shade of dyeing on PETP |
|---|---|---|---|
| 358 | 4-nitroaniline | " | yellow orange |
| 359 | 4-nitroaniline | 4-methyl-3-cyano-2,6-bis[(6-hydroxyhexyl)amino]pyridine | orange |
| 360 | 2-methyl-4-nitroaniline | " | orange |
| 361 | 2-chloro-4-nitroaniline | " | yellowish red |
| 362 | 2-methoxy-4-nitroaniline | " | yellowish red |
| 363 | 2-bromo-4-nitroaniline | " | yellowish red |
| 364 | 2-amino-5-nitrobenzonitrile | " | red |
| 365 | 2,4-dinitroaniline | " | red |
| 366 | 2-amino-3-bromo-5-nitrobenzonitrile | " | bluish red |
| 367 | 2-amino-3-chloro-5-nitrobenzonitrile | " | bluish red |

| EXAMPLE | Diazo component | Coupling component | Shade of dyeing on PETP |
|---|---|---|---|
| 368 | 2-amino-3-cyano-1,5-dinitrobenzene (NO₂, NH₂, CN, O₂N substituents) | " | bluish red |
| 369 | 4-amino-6-nitro-benzisothiazole | " | bluish red |
| 370 | 5-bromo-4-amino-6-nitro-benzisothiazole | " | red violet |
| 371 | 5-cyano-4-amino-6-nitro-benzisothiazole | " | violet |
| 372 | 3-amino-6-nitro-benzisothiazole | " | blue violet |
| 373 | 2-amino-5-chloro-benzonitrile | " | yellow |
| 374 | 2-amino-5-nitro-benzenesulfonic acid diethylamide | " | red |
| 375 | 2-amino-6-nitro-benzothiazole | " | yellowish red |
| 376 | N-propyl-3-amino-phthalimide | 4-methyl-3-cyano-2,6-bis[(3-hydroxybutoxypropyl)amino]pyridine: CH₃, CN, NH—(CH₂)₃—O—(CH₂)₄—OH, NH—(CH₂)₃—O—(CH₂)₄—OH | yellow |

| EXAMPLE | Diazo component | Coupling component | Shade of dyeing on PETP |
|---|---|---|---|
| 377 | 4-nitroaniline | " | orange |
| 378 | 4-nitro-2-methylaniline | " | orange |
| 379 | 4-nitro-2-methoxyaniline | " | yellowish red |
| 380 | 2-amino-6-nitrobenzothiazole | " | yellowish red |
| 381 | 2-chloro-4-nitroaniline | " | yellowish red |
| 382 | 4-nitroaniline | " | red |
| 383 | 2-amino-5-nitrobenzenesulfonic acid diethylamide | " | red |
| 384 | 2,4-dinitroaniline | " | red |
| 385 | 6-chloro-2,4-dinitroaniline | " | red |
| 386 | 6-bromo-2,4-dinitroaniline | " | red |
| 387 | 2-amino-5-nitro-N,N-dimethylbenzamide | " | red |

-continued

| EXAMPLE | Diazo component | Coupling component | Shade of dyeing on PETP |
|---|---|---|---|
| 388 | 2-amino-5-nitro-3-chlorobenzonitrile | " | bluish red |
| 389 | 2-amino-5-nitro-3-bromobenzonitrile | " | bluish red |
| 390 | 3-amino-6-nitro-benzisothiazole derivative | " | bluish red |
| 391 | 4-amino-5-bromo-7-nitro-benzisothiazole | " | red violet |
| 392 | bicyclic nitro-amino-isothiazole derivative | " | blue violet |
| 393 | 3-amino-6-nitro-2,1-benzisothiazole | " | blue violet |
| 394 | 2-amino-3,5-dibromobenzonitrile | " | orange |
| 395 | 2-amino-5-nitrobenzenesulfonic acid diethylamide | 2-amino-6-(2-hydroxyethylamino)-4-methyl-5-cyanopyridine | red |
| 396 | 2-amino-5-nitro-3-bromobenzonitrile | 2-(2-hydroxyethylamino)-6-(2-methoxyethylamino)-4-methyl-5-cyanopyridine | bluish red |

EXAMPLE 397

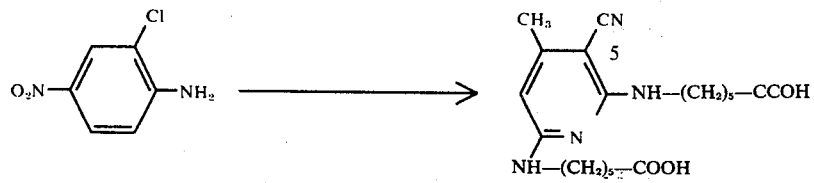

0.05 mole of a solution of the disodium salt of the above coupling component is allowed to flow gradually at 0° to 5° C into the diazonium salt solution obtained in the usual way from 15 parts of 2-chloro-4-nitro-1-aminobenzene. The coupling mixture is adjusted to pH 3 to 4 by adding 25 parts by volume of a saturated aqueous solution of sodium acetate. The dye obtained is suction filtered, washed with water and dried at 80°

It dyes polyester cloth yellowish red shades having good fastness to light and dry-heat pleating and setting.

The following dyes may be prepared in an analogous manner:

| EXAMPLE | Diazo component | Coupling component | Shade of dyeing on polyester |
|---|---|---|---|
| 398 | 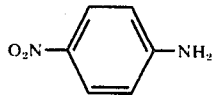 | 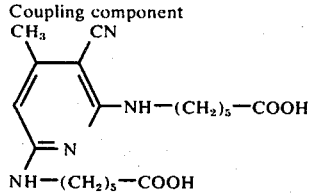 | orange |
| 399 | 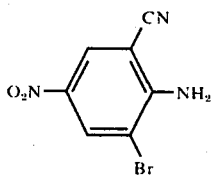 | 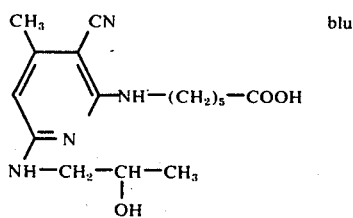 | bluish red |
| 400 | 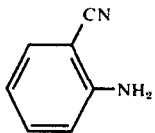 | 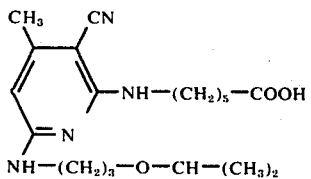 | yellow (polyamide: yellow) |
| 401 | 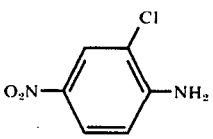 | " | yellowish red |
| 402 | 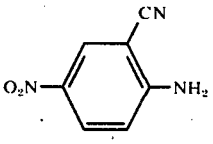 | " | red |
| 403 | 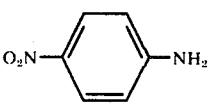 | " | orange |
| 404 | 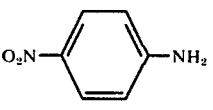 | 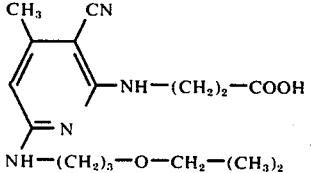 | orange |
| 405 | 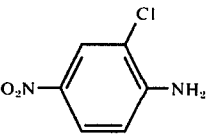 | " | yellowish red |

-continued
| EXAMPLE | Diazo component | Coupling component | Shade of dyeing on polyester |
|---|---|---|---|
| 406 | 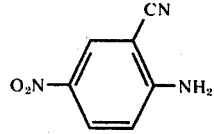 | " | red |
| 407 |  | | brilliant bluish red |
| 408 | 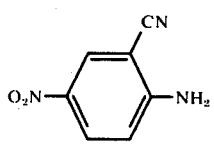 | 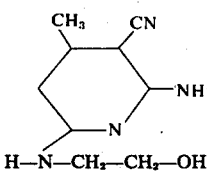 | red |
| 409 | 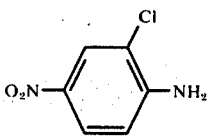 | " | yellowish red |
| 410 | 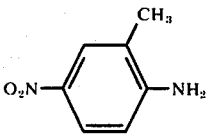 | " | yellowish red |
| 411 | 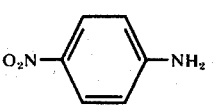 | " | orange |
| 412 | 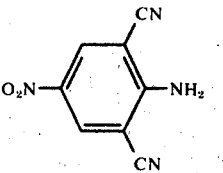 | " | orange |
| 413 | 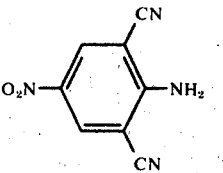 | " | bluish red |
| 414 | 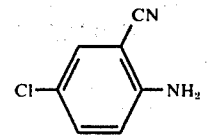 | " | reddish yellow |
| 415 | 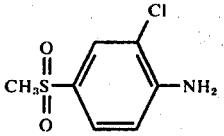 | " | reddish yellow |
| 416 | 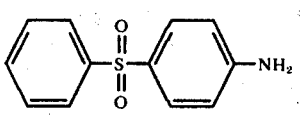 | | yellow |

-continued

| EXAMPLE | Diazo component | Coupling component | Shade of dyeing on polyester |
|---|---|---|---|
| 417 | 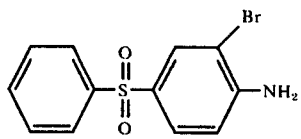 | " | orange |
| 418 | 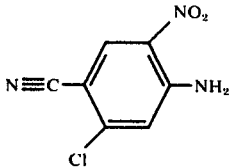 | " | red |
| 419 | 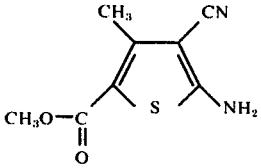 | " | red |
| 420 | 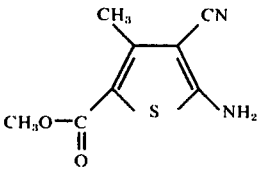 | 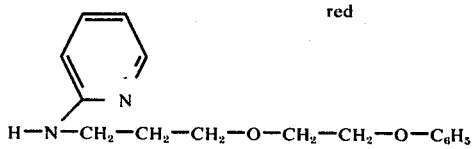 | red |
| 421 | 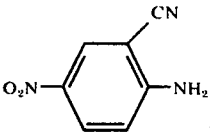 | " | red |

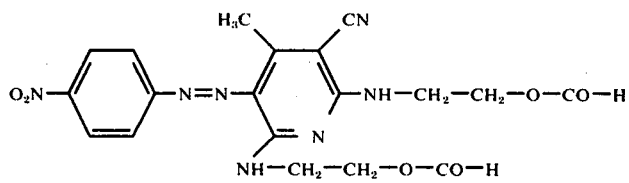

20 parts of the product obtained by coupling 4-nitro-1-amino-benzene onto 2,6-dihydroxyethylamino-3-cyano-4-methylpyridine is introduced as a dry powder into 250 parts of formic acid with stirring. The mixture is stirred for some hours at 80° C until complete esterification has been achieved as determined by thin-layer chromatography. The dye, which crystallizes out after cooling, is suction filtered, washed with cold methanol and dried at 80° C. A yellowish red powder is obtained which dissolves in acetone or dimethylformamide with an orange color. Orange dyeings with outstanding fastness properties are obtained on polyester articles. The following formic acid esters may be obtained with the same coupling component:

| EXAMPLE | Diazo component | Shade of dyeing on polyester |
|---|---|---|
| 423 | 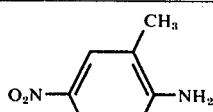 | orange |
| 424 | 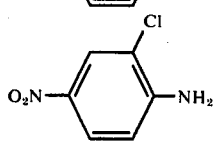 | yellowish red |

-continued

| EXAMPLE | Diazo component | Shade of dyeing on polyester |
|---|---|---|
| 425 | 2,6-dichloro-4-nitroaniline | yellowish red |
| 426 | 2-amino-3-cyano-5-nitrobenzene (2-cyano-4-nitroaniline) | red |
| 427 | 2-amino-3-nitro-5-nitrobenzene (2,4-dinitroaniline) | red |
| 428 | 2-amino-3-nitro-5-nitro-6-chlorobenzene | red |
| 429 | 2-amino-3-nitro-5-nitro-6-bromobenzene | red |
| 430 | 2-amino-3-cyano-5-nitro-6-chlorobenzene | bluish red |
| 431 | 2-amino-3-cyano-5-nitro-6-bromobenzene | bluish red |
| 432 | 2-amino-3-nitro-5-nitro-6-cyanobenzene | bluish red |
| 433 | 2-cyanoaniline | yellow |
| 434 | 2-cyano-4-chloroaniline | yellow |
| 435 | 2-methylsulfonyl-4-chloroaniline | yellow |

-continued

| EXAMPLE | Diazo component | Shade of dyeing on polyester |
|---|---|---|
| 436 | 4-Cl, 2-CF₃ aniline | yellow |
| 437 | phenyl-N=N-C₆H₄-NH₂ | orange |
| 438 | 2-CH₃-phenyl-N=N-(3-CH₃-4-NH₂-phenyl) | orange |
| 439 | 4-Cl-phenyl-N=N-(2-CH₃-4-NH₂-phenyl) | yellowish red |
| 440 | phenyl-N=N-(2,6-diBr-4-NH₂-phenyl) | yellowish red |
| 441 | 2,6-diBr-4-O₂N-aniline | yellowish red |
| 442 | 2-Br-4-O₂N-aniline | yellowish red |
| 443 | 5-O₂N-benzothiazole-2-NH₂ | yellowish red |
| 444 | 6-O₂N-benzothiazole-4-NH₂ | blue violet |
| 445 | 5-Br-7-O₂N-benzisothiazole-4-NH₂ | red violet |

EXAMPLE 446

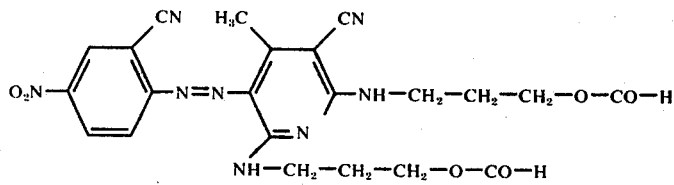

20 parts of the coupling product from 4-nitro-2-cyano-1-amino-benzene and 2,6-di-γ-hydroxy-propylamino-3-cyano-4-methylpyridine is esterified with formic acid as described in Example 422. A red dye is obtained which dyes polyesters is clear red shades which exhibit outstanding fastness to light and dry-heat pleating and setting.

When dyes having the same diaminopyridine derivative as coupling component are reacted in an analogous manner with formic acid, the following esters are obtained:

| EXAMPLE | Diazo component | Shade of dyeing on polyester |
|---|---|---|
| 447 | O₂N—⟨⟩—NH₂ | orange |
| 448 | O₂N—⟨CH₃⟩—NH₂ | orange |
| 449 | O₂N—⟨Cl⟩—NH₂ | yellowish red |
| 450 | O₂N—⟨Cl,Cl⟩—NH₂ | yellowish red |
| 451 | O₂N—⟨Br⟩—NH₂ | yellowish red |
| 452 | O₂N—⟨Br,Br⟩—NH₂ | yellowish red |
| 453 | O₂N—⟨SO₂—NH—C₄H₉⟩—NH₂ | red |
| 454 | O₂N—⟨COOC₂H₅⟩—NH₂ | red |
| 455 | O₂N—⟨NO₂⟩—NH₂ | red |
| 456 | O₂N—⟨NO₂⟩—NH₂ | red |
| 457 | O₂N—⟨Cl, NO₂⟩—NH₂ | red |
| 458 | O₂N—⟨Br, CN⟩—NH₂ | bluish red |
| 459 | O₂N—⟨Cl, CN⟩—NH₂ | bluish red |
| 460 | ⟨Br, CN⟩—NH₂ | yellow |
| 461 | Cl—⟨CN⟩—NH₂ | yellow |
| 462 | ⟨⟩—N=N—⟨⟩—NH₂ | orange |
| 463 | O₂N—benzothiazole—NH₂ | yellowish red |
| 464 | O₂N—isothiazole—NH₂ | bluish violet |
| 465 | O₂N—⟨⟩—NH₂ (with thiadiazole) | bluish red |

EXAMPLE 466

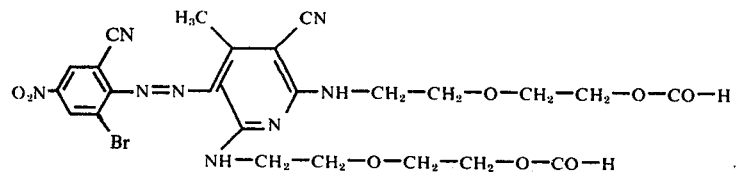

20 parts of the unesterified starting dye is stirred in 100 parts by volume of 98% formic acid for 4 hours at 60° C. The reaction product which crystallizes out at room temperature is isolated and dried. The dark red powder dissolves in dimethylformamide giving a claret color and gives ruby dyeings with outstanding fastness properties on polyesters.

When the following diazo components are used equivalent dyes are obtained:

| EXAMPLE | Diazo component | Shade |
|---|---|---|
| 467 | $O_2N$-C₆H₃(CN)-$NH_2$ | red |
| 468 | $O_2N$-C₆H₃(Cl)-$NH_2$ | yellowish red |
| 469 | $O_2N$-C₆H₄-$NH_2$ | orange |
| 470 | C₆H₅-N=N-C₆H₄-$NH_2$ | orange |
| 471 | $O_2N$-benzothiazole-$NH_2$ | yellowish red |
| 472 | $O_2N$-C₆H₂(CN)(Cl)-$NH_2$ | bluish red |

EXAMPLE 473

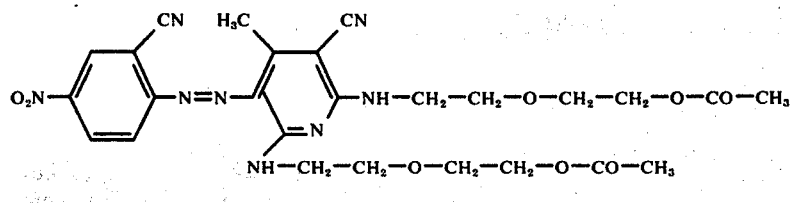

20 parts of the starting dye devoid of acetyl groups is dissolved in 100 parts by volume of glacial acetic acid at refluxing temperature. A mixture of 20 parts by volume of glacial acetic acid and 16 parts of acetic anhydride is then gradually introduced. After stirring for 5 hours at 115° C the whole is cooled and the dye is suction filtered and dried. It dyes polyester cloth clear red shades exhibiting excellent fastness properties.

Dyes having similar properties are obtained by the same process with the following diazo components:

| EXAMPLE | Diazo component | Shade |
|---|---|---|
| 474 | $O_2N$—⌬—$NH_2$ | orange |
| 475 | $O_2N$—⌬(Cl)—$NH_2$ | yellowish red |
| 476 | $O_2N$—benzothiazole—$NH_2$ | yellowish red |
| 477 | $O_2N$—⌬(CN)—$NH_2$ | bluish red |
| 478 | $O_2N$—⌬(CN, Br)—$NH_2$ | bluish red |

EXAMPLE 479

13 parts of the dried coupling product from diazotized 4-aminoazobenzene and 2,6-dihydroxyethylamino-3-cyano-4-methylpyridine are stirred in 150 parts by volume of acetic anhydride for one hour at 100° C. The reaction product which crystallizes out from the reaction solution upon cooling is suction filtered and washed with methanol. The compound which is obtained as a red powder after drying is soluble in dimethylformamide with a yellowish red color. Red orange shades having excellent fastness properties are obtained therewith on polyester fibers.

Dyes having similar tinctorial behavior are obtained with the diazo components set out in the following Table in an analogous way:

| EXAMPLE | Diazo component | Shade |
|---|---|---|
| 480 | $O_2N$—⌬—$NH_2$ | orange |
| 481 | $O_2N$—⌬($OCH_3$)—$NH_2$ | yellowish red |
| 482 | $O_2N$—⌬(Cl)—$NH_2$ | yellowish red |
| 483 | $O_2N$—⌬(C)—$NH_2$ | red |
| 484 | $O_2N$—⌬(CN, Cl)—$NH_2$ | bluish red |

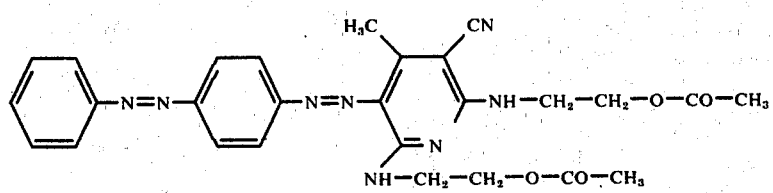

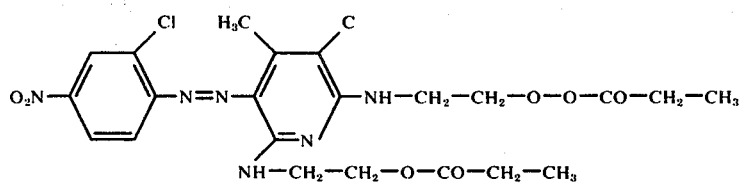

15 parts of propionic anhydride is added at 100° C to a mixture of 18 parts of the unesterified starting dye and 500 parts by volume of propionic acid and the reaction mixture is stirred at 115° C until complete reaction can be detected. The dye ester which crystallizes out after cooling is suction filtered, washed with methanol and dried. The red powder thus obtained dissolves in 80% acetone with a yellowish red color. Fast scarlet shades are obtained therewith on polyester cloth.

EXAMPLE 486

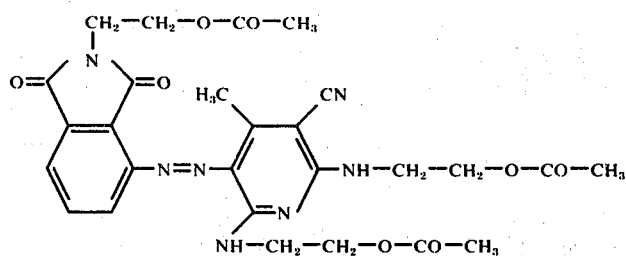

20 parts of acetic anhydride diluted with an equal amount of glacial acetic acid is added to a mixture of 200 parts by volume of glacial acetic acid and 20 parts of the dried coupling product of 3-aminophthalic acid-2-hydroxyethylimide and 2,6-di-β-hydroxyethylamio-3-cyano-4-methylpyridine. The reaction mixture is stirred at refluxing temperature until complete esterification has been achieved. The dye which crystallizes out on cooling and is isolated is an orange powder. It gives golden yellow dyeings with outstanding fastness properties on polyester cloth.

EXAMPLE 487

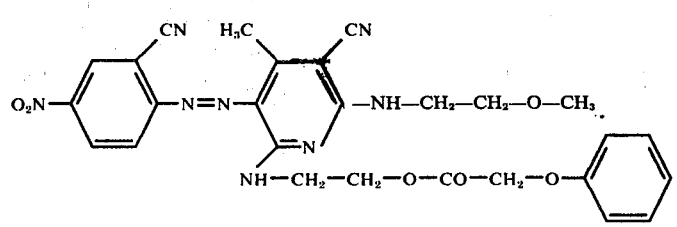

A mixture of 250 parts by volume of monochlorobenzene, 12.5 parts of phenoxyacetic acid, 2.5 parts of p-toluenesulfonic acid and 21 parts of the coupling product of 4-nitro-2-cyanoaniline and 2-(β-methoxyethylamino)-6-(-β-hydroxyethylamino)-3-cyano-4-methylpyridine is stirred for two hours at 100° C so that complete reaction is achieved. The reaction product crystallizes out on cooling and is dried. It is a red powder which dissolves in dimethylformamide with a red color. Fast clear red shades are obtained on polyester fibers preferably by the high temperature dyeing method at 130° C.

The following dye esters are obtained by this process with the same coupling component and the diazo components indicated:

| Ex. | Diazo component | Shade |
|---|---|---|
| 488 | O₂N—⟨⟩—NH₂ | orange |
| 489 |  | orange |
| 490 | O₂N—⟨CH₃⟩—NH₂ |  |
|  | O₂N—⟨OCH₃⟩—NH₂ | yellowish red |
| 491 |  | yellowish red |
| 492 | O₂N—⟨Cl⟩—NH₂ |  |
|  | O₂N—⟨COO—CH₂—CH₂—O—CH₃⟩—NH₂ | red |

-continued

| Ex. | Diazo component | Shade |
|---|---|---|
| 493 | 2,4-dinitroaniline | red |
| 494 | 2,4-dinitro-6-chloroaniline | red |
| 495 | 2-amino-3,5-dichloro... (O₂N, CN, Cl, NH₂) | bluish red |
| 496 | 2-amino-5-nitro-3-bromo-benzonitrile | bluish red |
| 497 | 2-aminobenzonitrile | yellow |
| 498 | 2-amino-5-chlorobenzonitrile | yellow |
| 499 | N-(3-methoxypropyl)phthalimide-amine | yellow |

EXAMPLE 500

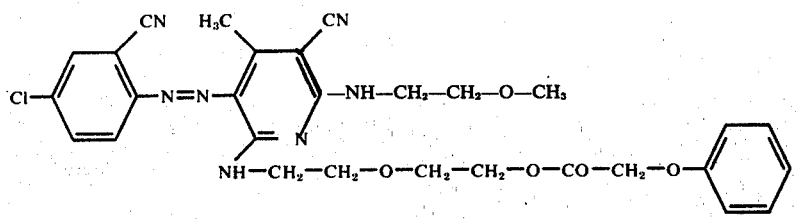

A mixture of 16 parts of the unesterified starting dye, 9 parts of phenoxyacetic acid, 2 parts of p-toluenesulfonic acid, 50 parts by volume of monochlorobenzene and 100 parts by volume of dichloroethane is gradually heated to 120° C while distilling off solvent and water of reaction and is stirred at this temperature until complete esterification has been achieved. This may be detected by thin-layer chromatography. Then 100 parts by volume of alcohol is added, the whole is kept for a short time at refluxing temperature and then the dye ester is isolated after cooling. After drying a yellow powder is obtained which dissolves in 80% acetone with a yellow color and gives yellow dyeings having excellent fastness properties on textile polyester material. Polyamide cloth is dyed fast yellow shades.

Dyes may be prepared with the following diazo components by the same process:

| Example | Diazo component | Shade |
|---|---|---|
| 501 | 2-aminobenzonitrile | yellow |
| 502 | 4-aminobenzonitrile | yellow |
| 503 | 2-amino-5-chloro-benzenesulfonyl methyl | yellow |
| 504 | 4-chloro-2-trifluoromethylaniline | yellow |
| 505 | 4-nitroaniline | orange |
| 506 | 2-methoxy-4-nitroaniline | |
| 507 | 2-chloro-4-nitroaniline | yellowish red |

-continued

| Example | Diazo component | Shade |
|---|---|---|
| 508 | [2,6-dichloro-4-nitroaniline structure] | yellowish red |
| 509 | [2-bromo-4-nitroaniline structure] | red |
| 510 | [2-nitro-4-nitroaniline structure] | red |
| 511 | [6-chloro-2-nitro-4-nitroaniline structure] | red |
| 512 | [2-(N,N-dimethylsulfamoyl)-4-nitroaniline structure] | red |
| 513 | [2-cyano-4-nitroaniline structure] | red |
| 514 | [2-cyano-6-nitro-aniline structure] | bluish red |
| 515 | [6-chloro-2-methyl-4-nitroaniline structure] | bluish red |
| 516 | [2-cyano-6-bromo-4-nitroaniline structure] | bluish red |

-continued

| Example | Diazo component | Shade |
|---|---|---|
| 517 | [nitro-benzothiazole amine structure] | bluish red |
| 518 | [bromo-nitro pyridine amine structure] | red violet |
| 519 | [nitro-isothiazole amine structure] | blue violet |
| 520 | [6-nitro-benzothiazol-2-amine structure] | yellowish red |

EXAMPLE 521

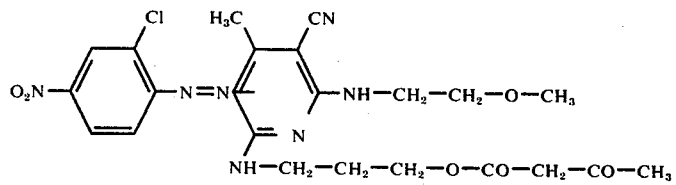

Diketene is dripped at 50° C into a mixture of 100 parts by volume of pyridine and 21 parts of the unesterified starting dye until the ester has been completely formed. To isolate the product, 100 parts of water is added at room temperature and the deposited dye is suction filtered, washed with methanol and dried. A red powder is obtained which dissolves in dimethylformamide with a yellowish red color and produces fast scarlet shades on polyester cloth.

EXAMPLE 522

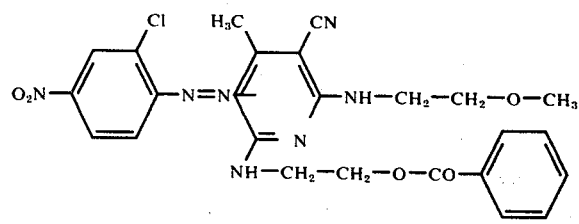

5 parts of benzoyl chloride is gradually added at 50° C to a mixture of 30 parts by volume of pyridine and 5 parts of unesterified starting dye. As soon as complete esterification has been achieved at 50° C the whole is allowed to cool and the reaction product is isolated by suction filtration, washing with alcohol and drying at 80° C. The red powder thus obtained produces scarlet shades having good fastness properties on polyester fibers.

EXAMPLE 523

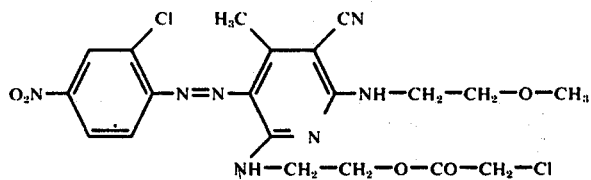

5 parts of chloroacetyl chloride is slowly added at 60° C to a mixture of 5 parts of the unesterified coupling product, 50 parts by volume of glacial acetic acid and 5 parts of hydrous sodium acetate. After esterification is over the reaction product is suction filtered cold, washed with methanol and dried. The red powder dyes polyester cloth fast scarlet shades.

EXAMPLE 524

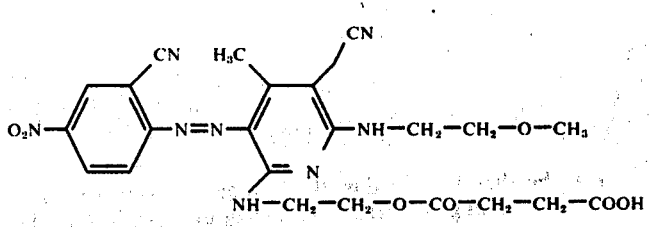

A mixture of 21 parts of the unesterified starting dye, 75 parts by volume of pyridine and 20 parts of succinic anhydride is stirred at 50° C until complete esterification has been achieved. The reaction product is cooled, suction filtered, washed with a little ethanol and dried at 80° C. The red powder thus obtained dissolves in dimethylformamide with a red color. Clear red shades having excellent fastness properties are obtained on polyester fibers.

EXAMPLE 525

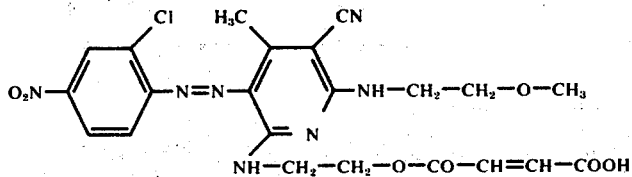

A mixture of 5 parts of starting dye and 5 parts of maleic anhydride is reacted in 30 parts of pyridine at 50° C until complete esterification has taken place. To isolate the dye, the reaction mixture has added to it a solution of 50 parts of water, 50 parts by volume of alcohol and 50 parts by volume of glacial acetic acid. The dye is suction filtered and dried. It is a red powder and gives scarlet dyeings having good fastness properties on polyester cloth.

EXAMPLE 526

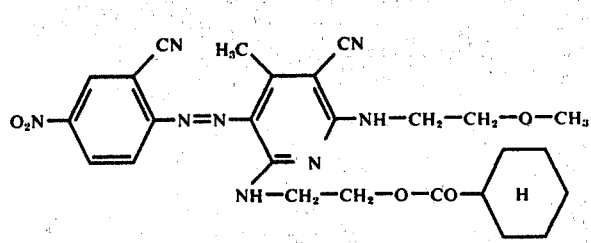

A mixture of 5 parts of starting dye, 3 parts of cyclohexanoic acid and 0.5 part of p-toluenesulfonic acid is stirred at 100° C until complete esterification has taken place. The dye isolated after cooling gives fast and clear red shades on polyester fibers.

EXAMPLE 527

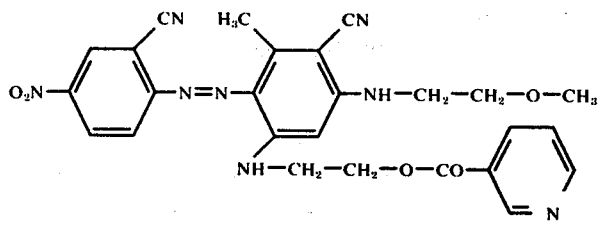

5 parts of the starting dye is reacted with 5 parts of nicotinic acid in 10 parts by volume of N-methylpyrrolidone as described in Example 500. A red reaction product is obtained which produces red shades having excellent fastness properties on polyester cloth.

EXAMPLE 528

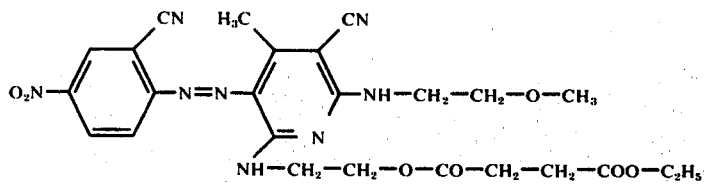

First 5 parts of starting dye and then 5 parts of succinic ethyl ester chloride are introduced into 15 parts of pyridine and the reaction mixture is then stirred at 50° C until the reaction is over. The dye is isolated cold and dried. It is then a red powder and gives fast and clear red shades on polyester yarn.

EXAMPLE 529

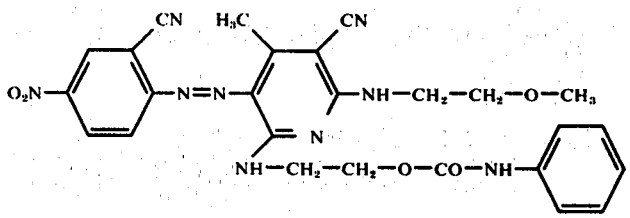

5 parts of phenyl isocyanate is gradually introduced at 100° C into a mixture of 5 parts pf starting dye and 50 parts of monochlorobenzene. After reaction has taken place the reaction product is suction filtered while hot, washed with alcohol and dried. Pure red shades having excellent fastness properties are obtained on polyester cloth with the red dye powder thus obtained.

EXAMPLE 530

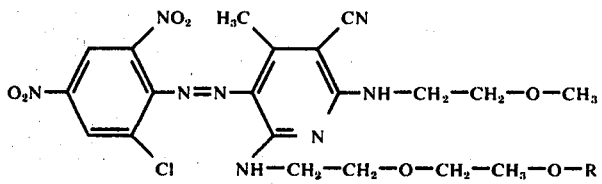

A mixture of 20 parts of starting dye (R = H), 8.5 parts of phenylacetic acid and 2 parts of p-toluenesulfonic acid is stirred at 100° C, then 100 parts of 1,2-dichloroethane is added and slowly distilled off again to remove water until a temperature of 120° C has been reached. The whole is kept at this temperature until starting dye can no longer be detected by thin-layer chromatography. After cooling to room temperature the dye ester

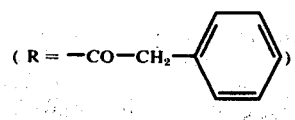

which has crystallized out is suction filtered, washed with a little alcohol and dried. The dark red powder may be dissolved in dimethylformamide with a deep red color and gives red shades having excellent fastness properties on polyester cloth.

EXAMPLE 531

4.7 parts of 2-cyano-1-aminobenzene is stirred with 100 parts of water and 10 parts by volume of 30% hydrochloric acid. Then 120 parts of ice and 12 parts by volume of 23% sodium nitrite solution is added. After stirring for two hours at 0° to 5° C any excess of nitrous acid present is destroyed as usual and the product is filtered. The diazonium solution thus obtained is added in portions to a solution, cooled to 0° to 5° C, of the coupling component of the formula:

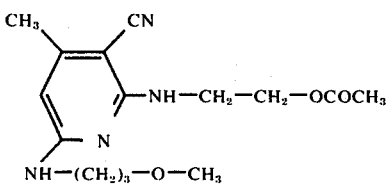

in 450 parts of water and 10 parts by volume of 30% hydrochloric acid. The mixture is stirred for one hour and then 50% sodium acetate solution is added until the pH of the coupling mixture is 3.

After coupling is over the dye of the formula:

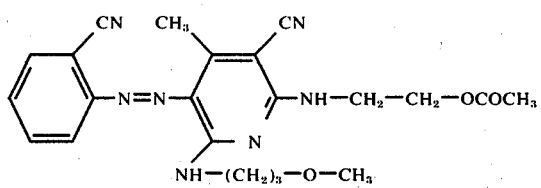

is suction filtered, washed with water until neutral and dried. A yellow powder is obtained which dyes polyethylene terephthalate cloth full yellow shades by the carrier and HT methods.

Fast yellow shades are obtained on polyamide fibers.

Production of the coupling component for Example 531

160 parts of the compound having the formula:

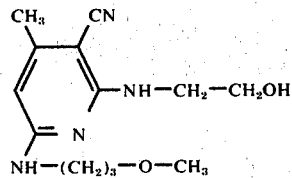

is heated for 3 hours under reflux with 500 parts by volume of glacial acetic acid and 65 parts by volume of acetic anhydride. After distilling off about 150 parts by volume of glacial acetic acid the whole is allowed to cool to 80° C and the mixture is stirred into 1500 parts of water. The deposited precipitate of the formula:

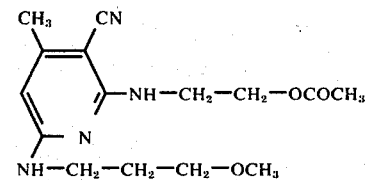

is filtered off, washed with water and dried. 150 parts of a colorless powder is obtained which melts at 78° to 80° C.

EXAMPLE 532

14 parts of the dye of the formula:

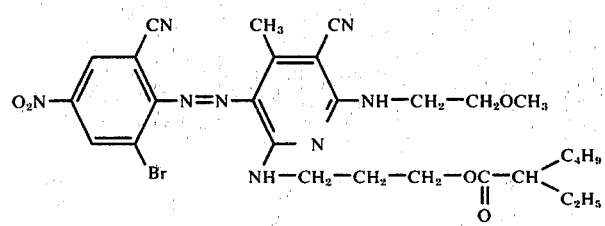

is suspended in 100 parts by volume of chlorobenzene. 6 parts of 2-ethylhexanoyl chloride and 4 parts of pyridine are added and the mixture is stirred for ten hours at 80° to 100° C. After cooling, 300 parts by volume of methanol, is added and the deposited dye of the formula

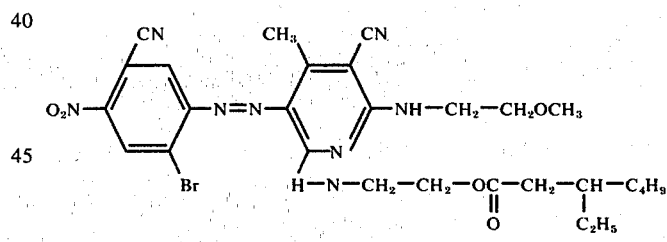

is suction filtered and washed first with methanol and then with water.

A dark red powder is obtained which dissolves in dimethylformamide with a bluish red color and dyes polyethylene terephthalate cloth dark red shades having very good light fastness.

The following dyes are obtained by the process described in the foregoing Examples:

| Example | Diazo + coupling components | Shade on polyester |
|---|---|---|
| 533 | ![structure](O₂N—⟨benzene with CN, Br⟩—N=N—⟨pyridine with CH₃, CN⟩—NH—CH₃, H—N—CH₂—CH₂—OCOC₂H₅) | bluish red |

-continued
| Example | Diazo + coupling components | Shade on polyester |
|---|---|---|
| 534 | 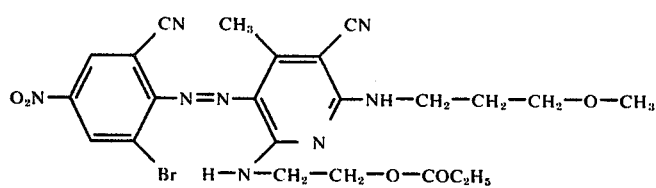 | " |
| 535 | 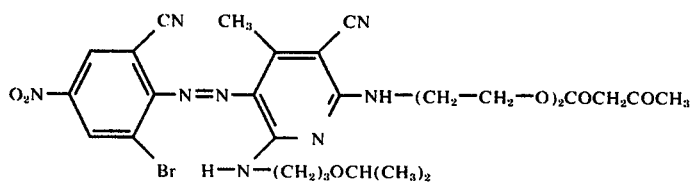 | " |
| 536 | 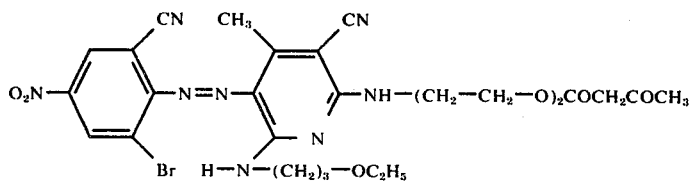 | " |
| 537 | 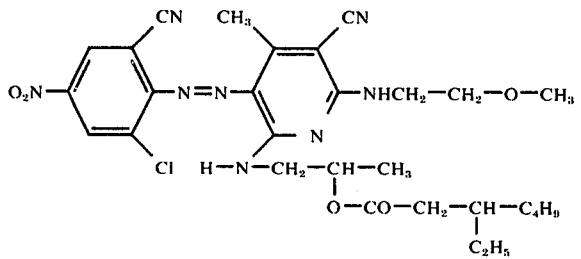 | " |
| 538 | 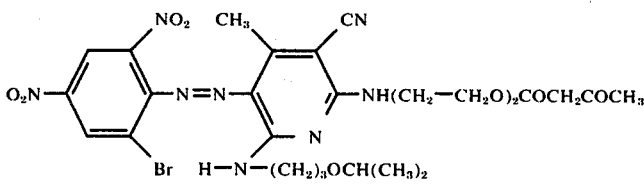 | red |
| 539 | 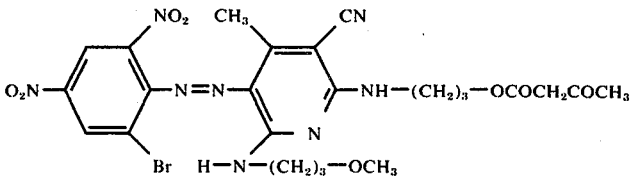 | red |
| 540 | 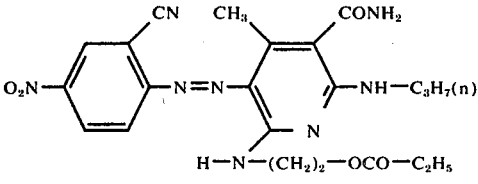 | red |
| 541 | 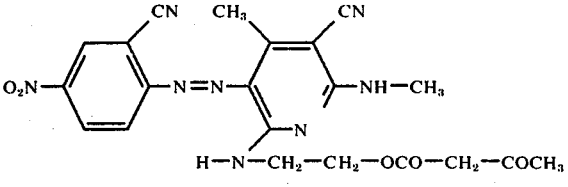 | red |
| 542 | 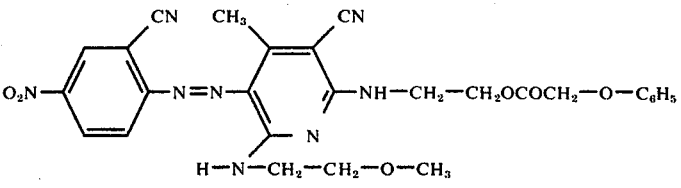 | red |

-continued
| Example | Diazo + coupling components | Shade on polyester |
|---|---|---|
| 543 | 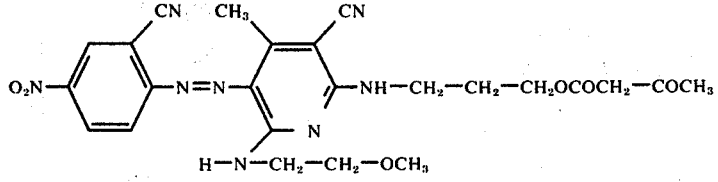 | red |
| 544 | 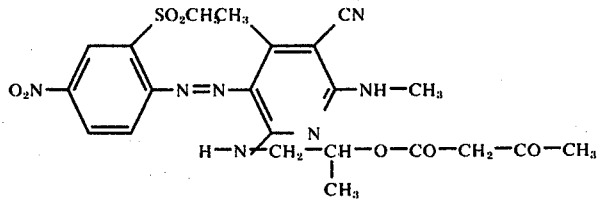 | red |
| 545 | 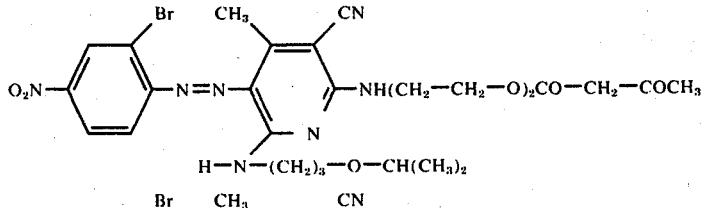 | yellowish red |
| 546 | 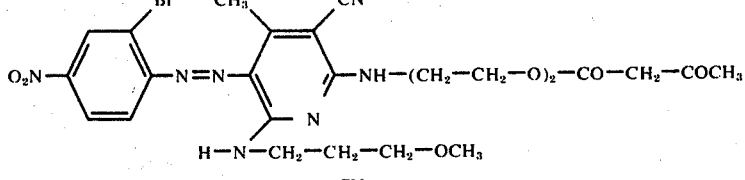 | yellowish red |
| 547 | 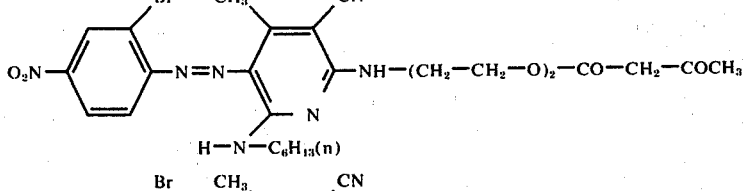 | yellowish red |
| 548 | 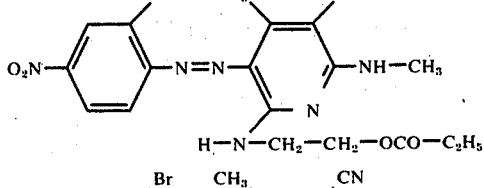 | yellowish red |
| 549 | 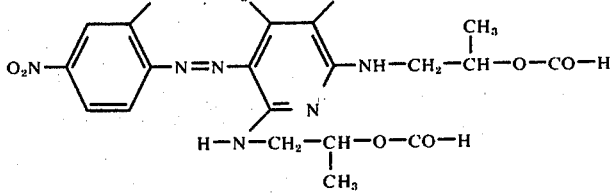 | yellowish red |
| 550 | 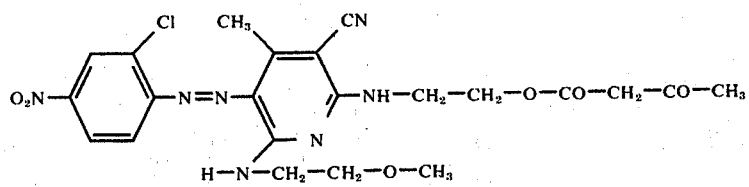 | yellowish red |
| 551 | 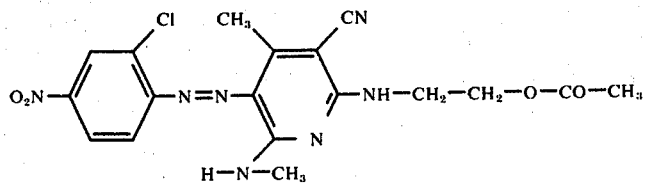 | yellowish red |

| Example | Diazo + coupling components | Shade on polyester |
|---|---|---|
| 552 | O₂N–C₆H₃(Cl)–N=N–C(=C(CH₃)–C(CN)=C–NH–C₆H₄–CH₃)–C(=N–)–NH–CH₂–CH₂–O–CO–CH₂–CO–CH₃ | red |
| 553 | O₂N–C₆H₃(Cl)–N=N–C(=C(CH₃)–C(CN)=C–NH–CH₂–CH₂–O–CO–CH₂–CO–CH₃)–C(=N–)–NH–CH₃ | yellowish red |
| 554 | O₂N–C₆H₃(Cl)–N=N–C(=C(CH₃)–C(CN)=C–NH–(CH₂)₃–O–CH₃)–C(=N–)–NH–CH₂–CH₂–O–CO–C₂H₅ | yellowish red |
| 555 | O₂N–C₆H₄–N=N–C(=C(CH₃)–C(CN)=C–NH–CH₂CH₂–O–CO–CH₃)–C(=N–)–N(CH₃)–CH₂–CH₂–O–CO–CH₃ | orange (acetate: golden yellow) |
| 556 | O₂N–C₆H₃(OCH₃)–N=N–C(=C(CH₃)–C(CN)=C–NH–CH₂–CH₂–O–CO–CH₂O–C₆H₅)–C(=N–)–NH–CH₂–CH₂–O–CH₃ | yellowish red |
| 557 | Cl–C₆H₃(CN)–N=N–C(=C(CH₃)–C(CN)=C–NH(CH₂–CH₂–O)₂CO–CH₂–CO–CH₃)–C(=N–)–NH–(CH₂)₃–O–C₂H₅ | reddish yellow (polyamide: reddish yellow) |
| 558 | O₂N–(benzisothiazole, Br)–N=N–C(=C(CH₃)–C(CN)=C–NH–CH₂–CH₂–O–CO–CH₂–CO–CH₃)–C(=N–)–NH–(CH₂)₃–O–CH₃ | violet |
| 559 | O₂N–C₆H₃(COOCH₃)–N=N–C(=C(CH₃)–C(CN)=C–NH(CH₂)₃–O–CO–CH₂–CO–CH₃)–C(=N–)–NH–CH₂–CH₂–OCH₃ | red |

EXAMPLE 560

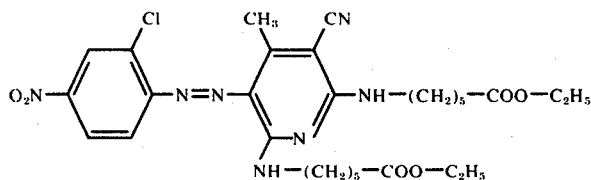

Into the diazonium salt solution obtained in the usual way from 17 parts of 2-chloro-4-nitroaniline there are introduced at 0° to 5° C 350 parts by volume of a 0.3 molar aqueous solution of:

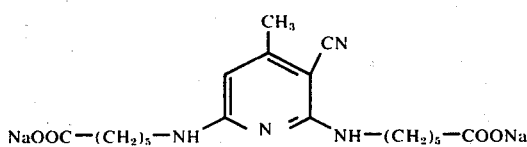

and then 200 parts by volume of a 50% sodium acetate solution. After coupling is over, the product is suction filtered, washed with water and dried. A mixture of 20 parts of the coupling product thus obtained, 500 parts by volume of ethanol and 1 part of p-toluenesulfonic acid is stirred at the boiling temperature while distilling off a mixture of alcohol and water until complete esterification has been achieved.

The reaction product is suction filtered cold, washed with alcohol and dried. The red powder thus obtained dissolves in 80% acetone with a yellowish red color. It dyes polyester cloth fast scarlet shades.

Dyes having similar properties are obtained after esterification when the following compounds are used as coupling components:

| Ex. | Coupling component | Shade |
|---|---|---|
| 561 | 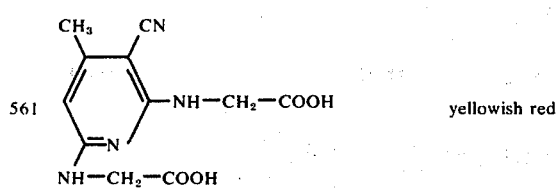 | yellowish red |
| 562 | | yellowish red |
| 563 | | yellowish red |

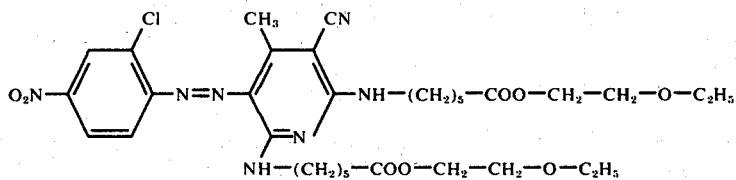

Example 564

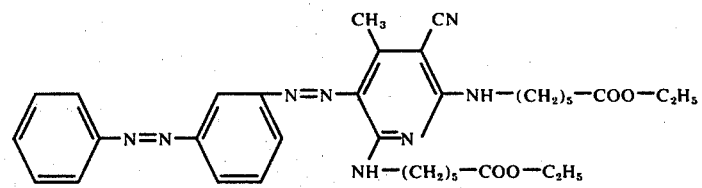

A mixture of 15 parts of the coupling product obtained according to Example 560, paragraph 1, 100 parts by volume of 2-ethoxyethanol and 3 parts of p-toluenesulfonic acid is stirred at 105° C until complete reaction has been achieved. The whole is cooled and the reaction product is suction filtered, washed with alcohol and dried. A red powder is obtained which when finely dispersed in the dye liquor gives clear scarlet dyeings of excellent fastness properties on polyesters.

EXAMPLE 565

20 parts of the unesterified starting dye obtained analogously to the first paragraph of Example 560 is esterified with ethanol as described in the first paragraph of Example 560. The isolated reaction product gives fast orange dyeings on polyester cloth.

EXAMPLE 566

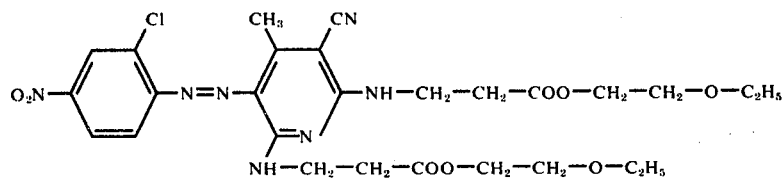
20 parts of the coupling product obtained as described in the first paragraph of Example 560 is reacted as described in Example 564 with 2-ethoxyethanol. After isolation and drying a red powder is obtained which gives fast scarlet dyeings on polyester threads and filaments.
The following dyes are obtained by the process according to the foregoing Examples:
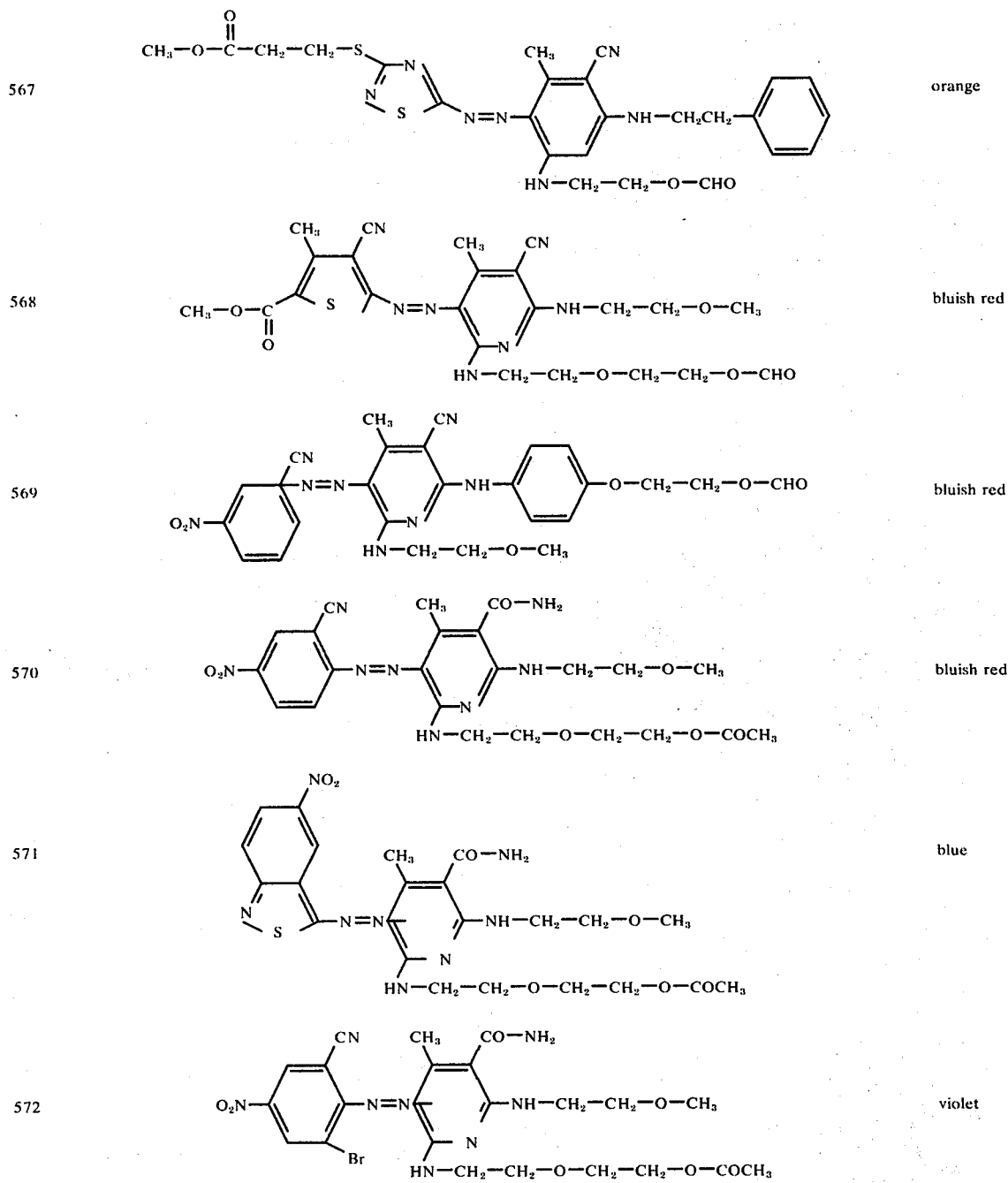

-continued
| | | |
|---|---|---|
| 573 | 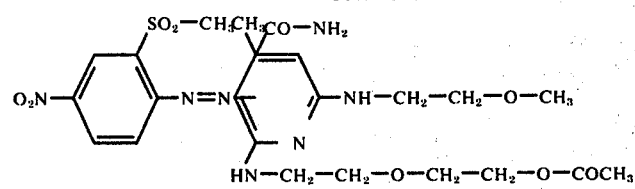 | ruby |
| 574 | 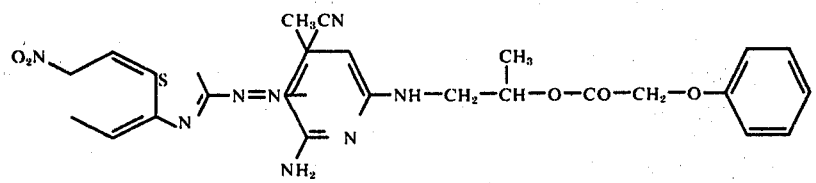 | yellowish red |
| 575 | 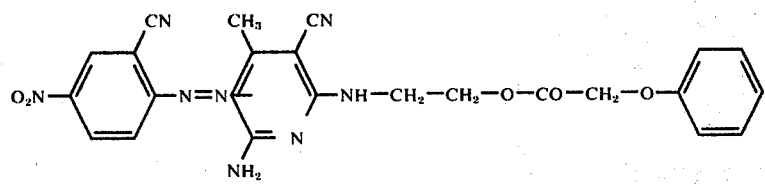 | yellowish red |
| 576 | 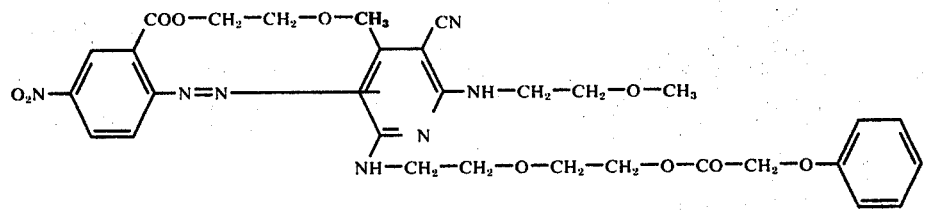 | red |
| 577 | 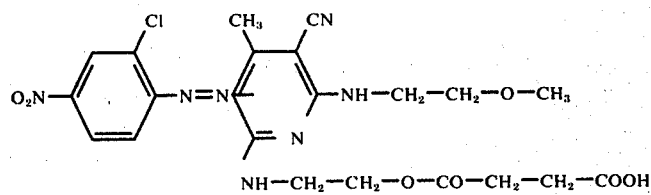 | yellowish red |
| 578 | 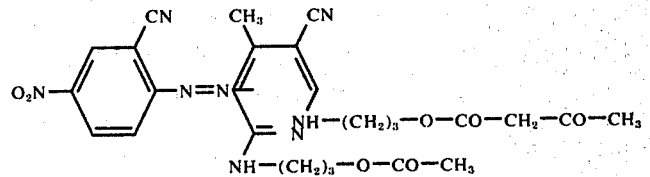 | red |
| 579 | 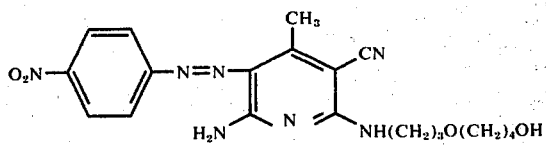 | yellow orange |
| 580 | 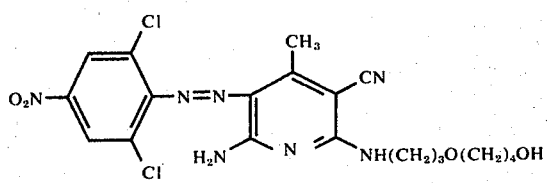 | yellow orange |
| 581 | 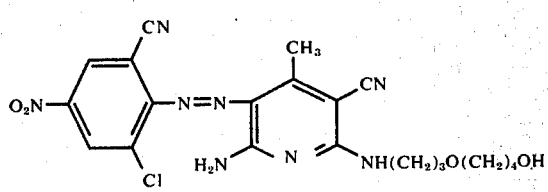 | red |

-continued
| | | |
|---|---|---|
| 582 | 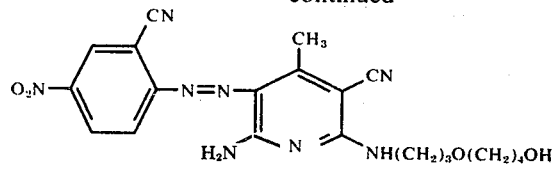 | yellowish red |
| 584 | 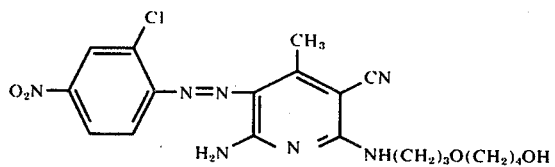 | red orange |
| 585 | 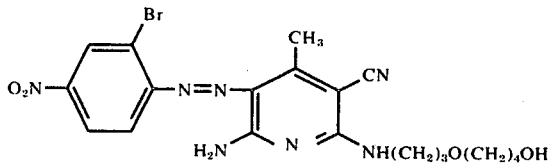 | yellowish orange |
| 586 | 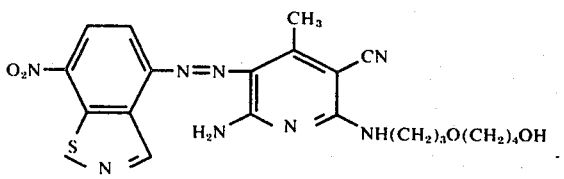 | bluish red |
| 587 | 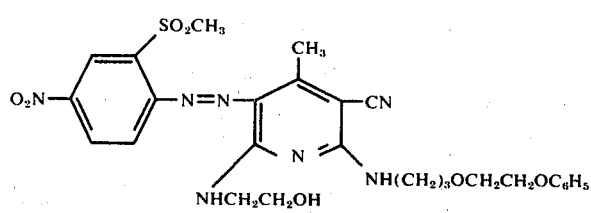 | bluish red |
| 588 | 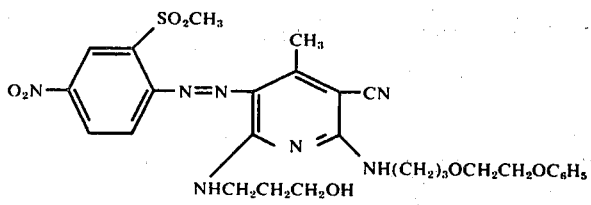 | bluish red |
| 589 | 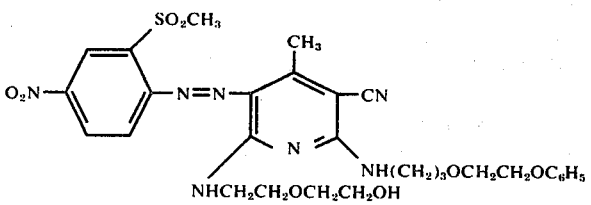 | bluish red |
| 590 | 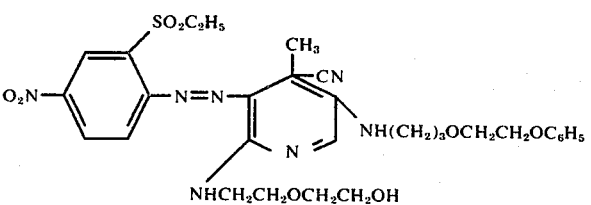 | bluish red |
| 591 | 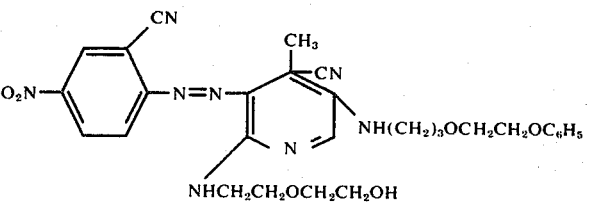 | red |

-continued
592 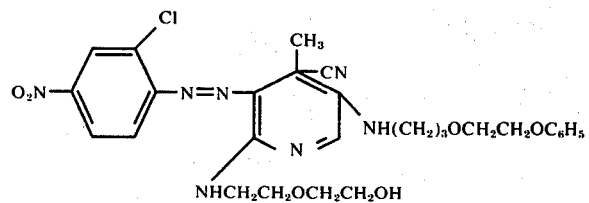 yellowish red
593 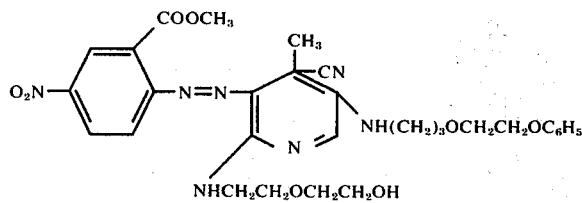 yellowish red
594 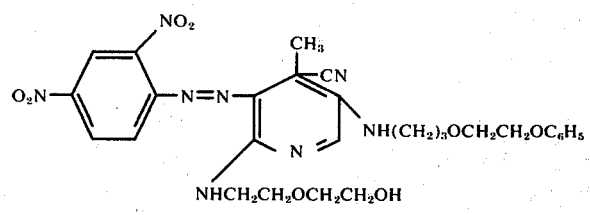 bluish red
595 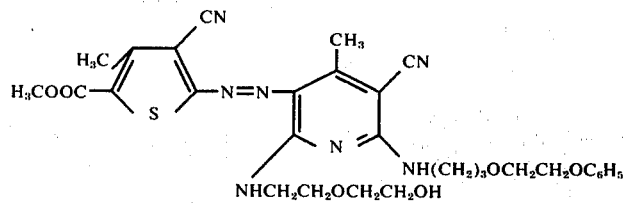 bluish red
596 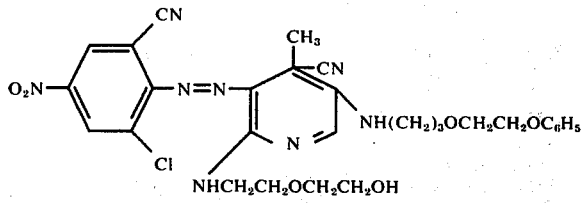 bluish red
597 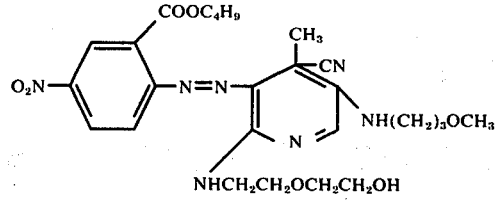 red
598 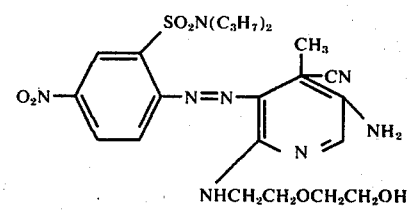 red
599 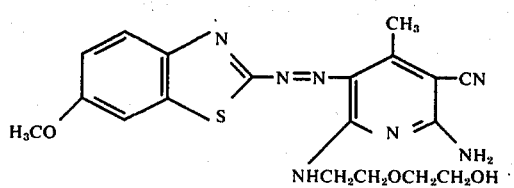 yellowish red -continued
| | | |
|---|---|---|
| 600 | 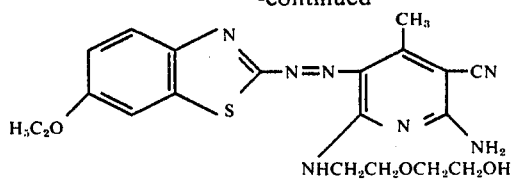 | yellowish red |
| 601 | 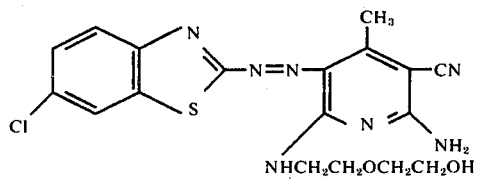 | yellowish red |
| 602 | 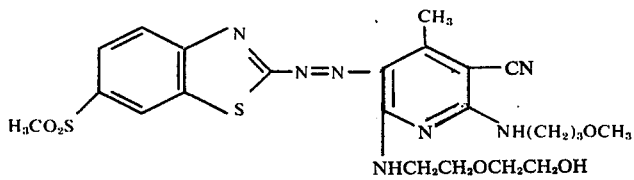 | yellowish red |
| 603 | 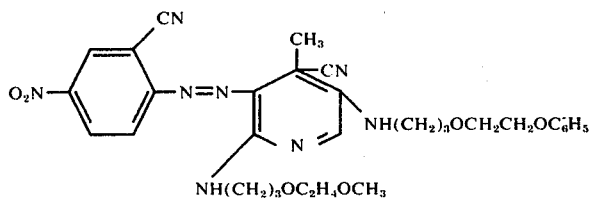 | red |
| 604 | 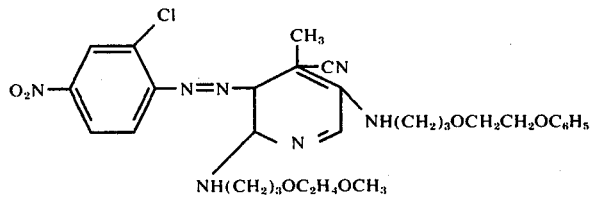 | yellowish red |
| 605 | 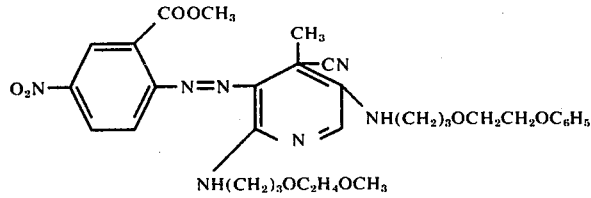 | red |
| 606 | 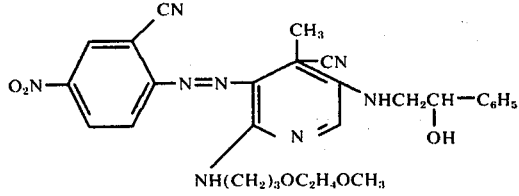 | red |
| 607 | 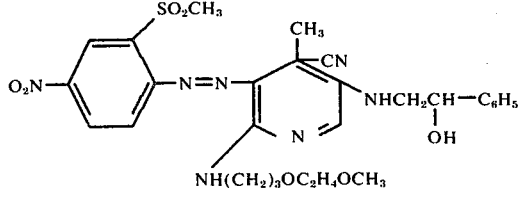 | bluish red |
We claim:
1. A dye of the formula

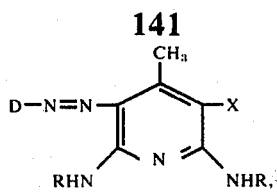

where
D is phenyl substituted by chlorine, bromine, methyl, trifluoromethyl, methoxy, nitro, cyano, methylsulfonyl, ethylsulfonyl, phenylsulfonyl, carbalkoxy of a total of 2 to 5 carbon atoms, carbo-β-alkoxyethoxy, said alkoxy having 1 to 4 carbon atoms, or N,N-dialkyl-substituted sulfamoyl, said alkyl having 1 to 3 carbon atoms; phenylazophenyl; phenylazophenyl substituted by chlorine, bromine or nitro; benzthiazolyl; benzthiazolyl substituted by chlorine, methoxy, ethoxy, nitro, cyano, methylsulfonyl or ethylsulfonyl; benzisothiazolyl substituted by chlorine, bromine, cyano or nitro; thiazolyl substituted by cyano or nitro; thienyl substituted by methyl, cyano, nitro, carbalkoxy of a total of 2 to 5 carbon atoms; or thiadiazolyl substituted by phenyl, ethyl, chlorine, bromine, methylmercapto, ethylmercapto or alkoxycarbonylethylmercapto, said alkoxy having 1 to 4 carbon atoms;

X is cyano or carbamoyl; one
R is allyl; alkyl of 1 to 8 carbon atoms; alkyl of 2 to 6 carbon atoms substituted by hydroxy, alkoxy of 1 to 8 carbon atoms, carboxy, carbalkoxy of a total of 2 to 5 carbon atoms, alkanoyloxy of 1 to 4 carbon atoms, acetoacetoxy, phenoxyacetyl, phenylacetyl, amino, alkylamino or dialkylamino of a total of 1 to 8 carbon atoms; benzyl, phenylethyl phenyl substituted by chlorine, methyl, ethyl, β-hydroxyethyl, β-hydroxyethoxy, methoxy or ethoxy; cyclohexyl; hydroxycyclohexyl; ω-N-pyrrolidonylalkyl, said alkyl having 2 or 3 carbon atoms; CH₂CH₂OCH₂CH₂OH; (CH₂)₃O(CH₂)₄OH; (CH₂)₃OC₂H₄OCH₃; (CH₂)₃OC₂H₄OC₆H₅; or

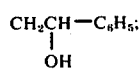

and the other R is hydrogen; alkyl of 1 to 8 carbon atoms; alkyl of 2 to 6 carbon atoms substituted by hydroxy, alkoxy of 1 to 8 carbon atoms, carboxy, carbalkoxy of a total of 2 to 5 carbon atoms, alkanoyloxy of 1 to 4 carbon atoms, amino, alkylamino or dialkylamino of a total of 1 to 8 carbon atoms; CH₂CH₂OCH₂CH₂OH; (CH₂)₃O(CH₂)₄OH; or (CH₂)₃OC₂H₄OCH₃.

2. A dye according to the formula in claim 1, wherein D is phenyl substituted by nitro, cyano, carbomethoxy, methylsulfonyl, ethylsulfonyl, chlorine or bromine.

3. A dye according to the formula in claim 1 wherein D is benzisothiazolyl substituted by nitro, cyano, chlorine or bromine; thiazolyl substituted by nitro; thiadiazolyl substituted by methylmercapto, ethylmercapto or alkoxycarbonylethylmercapto, said alkoxy having 1 or 2 carbon atoms, thienyl substituted by cyano, nitro, methyl or carbomethoxy; benzthiazolyl; or benzthiazolyl substituted by methoxy, ethoxy, chlorine or nitro.

4. A dye according to the formula in claim 1, wherein X is cyano.

5. A dye according to the formula in claim 1, wherein one R is hydrogen, hydroxyalkyl of 2 to 6 carbon atoms or CH₂CH₂OCH₂CH₂OH and the other R is phenylethyl, CH₂CH₂OCH₂CH₂OH,

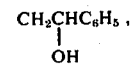

(CH₂)₃O(CH₂)₄OH, (CH₂)₃OC₂H₄OCH₃ or (CH₂)₃OC₂H₄OC₆H₅.

6. The dye having the formula

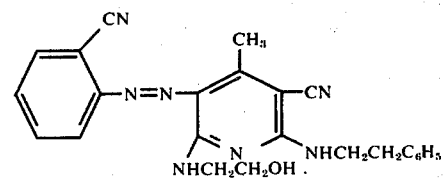

7. The dye having the formula

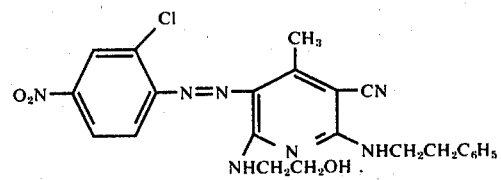

8. The dye having the formula

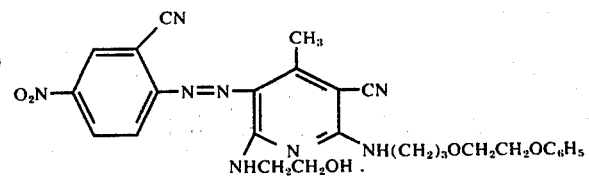

9. The dye having the formula

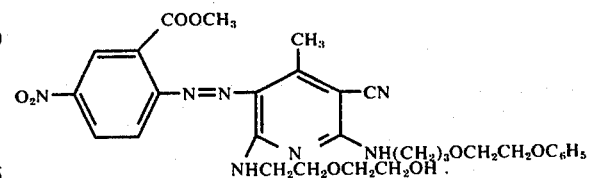

10. The dye having the formula

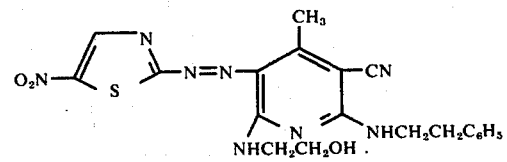

11. The dye having the formula

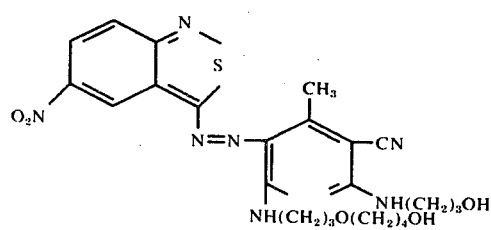
12. The dye having the formula
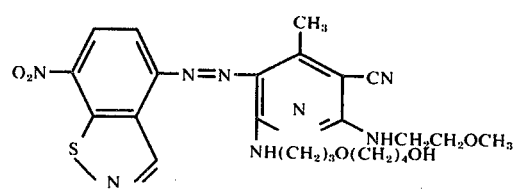
13. The dye having the formula
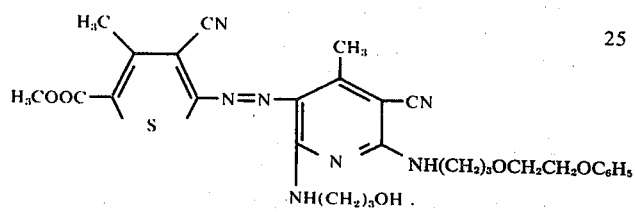
14. The dye having the formula
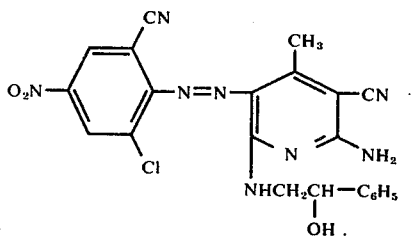
15. The dye having the formula
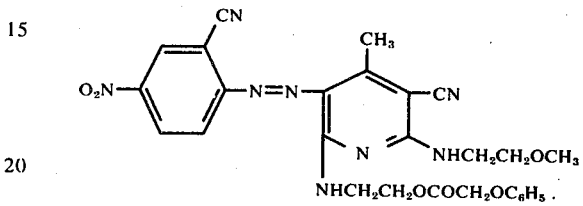
16. The dye having the formula
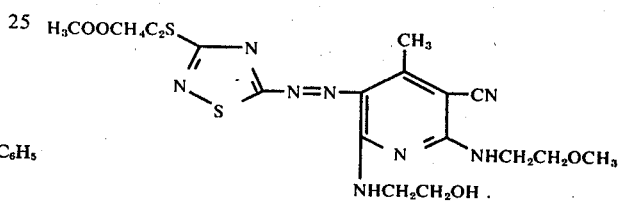
\* \* \* \* \*